US009789157B2

(12) United States Patent
Ellis-Behnke et al.

(10) Patent No.: US 9,789,157 B2
(45) Date of Patent: Oct. 17, 2017

(54) COMPOSITIONS FOR PREVENTION OF ADHESIONS AND OTHER BARRIER APPLICATIONS

(71) Applicant: Arch Biosurgery, Inc., Cambridge, MA (US)

(72) Inventors: Rutledge Ellis-Behnke, Myrtle Beach, SC (US); Terrence W. Norchi, Natick, MA (US); Stephen Richard Kelly, Manchester, MA (US)

(73) Assignee: Arch Biosurgery, Inc., Cambridge, MA (US)

( * ) Notice: Subject to any disclaimer, the term of this patent is extended or adjusted under 35 U.S.C. 154(b) by 0 days.

(21) Appl. No.: 14/885,673

(22) Filed: Oct. 16, 2015

(65) Prior Publication Data
US 2016/0030505 A1 Feb. 4, 2016

Related U.S. Application Data

(60) Division of application No. 11/740,284, filed on Apr. 25, 2007, now Pat. No. 9,162,005, which is a continuation-in-part of application No. 11/411,745, filed on Apr. 25, 2006, now Pat. No. 9,327,010.

(60) Provisional application No. 60/745,601, filed on Apr. 25, 2006, provisional application No. 60/758,827, filed on Jan. 13, 2006, provisional application No. 60/674,612, filed on Apr. 25, 2005.

(51) Int. Cl.
*A61K 38/10* (2006.01)
*A61L 15/42* (2006.01)
*A61L 26/00* (2006.01)

(52) U.S. Cl.
CPC .............. *A61K 38/10* (2013.01); *A61L 15/42* (2013.01); *A61L 26/0061* (2013.01)

(58) Field of Classification Search
CPC ...... A61K 38/10; A61L 15/42; A61L 26/0061
USPC ....................................................... 514/16.5
See application file for complete search history.

(56) References Cited

U.S. PATENT DOCUMENTS

| 4,098,728 A | 7/1978 | Rosenblatt |
| 4,211,227 A | 7/1980 | Anderson et al. |
| 4,272,398 A | 6/1981 | Jaffe |
| 4,636,208 A | 1/1987 | Rath |
| 4,829,000 A | 5/1989 | Kleinman |
| 4,861,627 A | 8/1989 | Mathiowitz et al. |
| 5,019,646 A | 5/1991 | Furcht |
| 5,180,375 A | 1/1993 | Feibus |
| 5,192,302 A | 3/1993 | Kensey et al. |
| 5,222,974 A | 6/1993 | Kensey et al. |
| 5,645,565 A | 7/1997 | Rudd et al. |
| 5,670,483 A | 9/1997 | Zhang et al. |
| 5,762,846 A | 6/1998 | Blankenbeckler |
| 5,955,343 A | 9/1999 | Holmes et al. |
| 6,333,194 B1 | 12/2001 | Levy et al. |
| 6,368,877 B1 | 4/2002 | Zhang et al. |
| 6,548,630 B1 | 4/2003 | Zhang et al. |
| 6,663,655 B2 | 12/2003 | Ginn et al. |
| 6,711,879 B2 | 3/2004 | Korteweg et al. |
| 6,800,116 B2 | 10/2004 | Stevens et al. |
| 6,800,481 B1 | 10/2004 | Holmes et al. |
| 6,844,324 B1 | 1/2005 | Zhang et al. |
| 6,953,656 B2 | 10/2005 | Jacobson et al. |
| 6,953,659 B2 | 10/2005 | Jacobson et al. |
| 7,098,028 B2 | 8/2006 | Holmes et al. |
| 7,179,784 B2 | 2/2007 | Zhang et al. |
| 7,390,526 B2 | 6/2008 | Stupp |
| 7,449,180 B2 | 11/2008 | Kisiday et al. |
| 7,700,721 B2 | 4/2010 | Boden |
| 7,704,740 B2 | 4/2010 | Schindler |
| 8,039,258 B2 | 10/2011 | Harris |
| 8,512,728 B2 | 8/2013 | Ladet |
| 8,568,637 B2 | 10/2013 | Gazit |
| 9,339,476 B2 | 5/2016 | Norchi |
| 9,415,084 B2 | 8/2016 | Ellis-Behnke |
| 2002/0072074 A1 | 6/2002 | Zhang et al. |
| 2002/0160471 A1 | 10/2002 | Kisiday et al. |
| 2003/0176335 A1 | 9/2003 | Zhang et al. |
| 2004/0011201 A1 | 1/2004 | Stevens |
| 2004/0023414 A1 | 2/2004 | Zhang et al. |
| 2004/0087013 A1 | 5/2004 | Holmes |
| 2004/0204561 A1 | 10/2004 | Ellison |

(Continued)

FOREIGN PATENT DOCUMENTS

| WO | WO 95/09659 | 4/1995 |
| WO | WO 98/58967 | 12/1998 |

(Continued)

OTHER PUBLICATIONS

Adler, "Self-assembling gel stops bleeding in seconds", *New Scientist Tech*, 1(3):117 (Oct. 10, 2006).
AlertNet, "Researches Study liquid as tool to stop bleeding", www.alertnet.org, pp. 1, (Oct. 10, 2016).
Ball, "Brain Knitting", materials@nature.com, pp. 1-2 (2006).
Bansal, "Scientists develop liquid that could revolutionize bleeding control", *All Headline News*, pp. 1 (2006).
Barone, "Nanoliquid stops bleeding practically in a nanosecond", *Discover Magazine*, pp. 1 (Feb. 25, 2007), accessed Dec. 22, 2007.
BBC News, "Liquid to seal open wounds fast", www.newsvote. bbc.co.uk, pp. 1-3, (Oct. 14, 2006), accessed Jul. 10, 2009.
Bokhari, et al., "The enhancement of osteoblast growth and differentiation in vitro on a peptide hydrogel-polyHIPE polymer hybrid material", *Biomaterials*, 26(25):5198-208 (2005).

(Continued)

*Primary Examiner* — Julie Ha
(74) *Attorney, Agent, or Firm* — Pabst Patent Group LLP

(57) ABSTRACT

A method has been developed of preventing or limiting formation of adhesions by administering to a site in need thereof, in the absence of or after bleeding or leakage of fluid has been substantially stopped, a self-assembling material which forms a barrier to formation of adhesions. In certain embodiments, the self assembling materials are peptidomimetics, nucleotidomimetics, di- and triblock copolymers, N-alkylacrylamides, or dendimers. These materials are also useful in a method for regeneration or repair of tissue or cells forming tissue.

19 Claims, No Drawings

(56) References Cited

U.S. PATENT DOCUMENTS

| | | |
|---|---|---|
| 2004/0242469 A1 | 12/2004 | Lee et al. |
| 2005/0181973 A1* | 8/2005 | Genove .............. C07K 14/78 514/21.5 |
| 2005/0209145 A1* | 9/2005 | Stupp .............. C07K 14/475 514/8.1 |
| 2005/0287186 A1 | 12/2005 | Ellis-Behnke et al. |
| 2006/0019309 A1 | 1/2006 | Zhang et al. |
| 2006/0025524 A1 | 2/2006 | Schneider et al. |
| 2006/0084607 A1 | 4/2006 | Spirio et al. |
| 2006/0088510 A1 | 4/2006 | Lee et al. |
| 2006/0148703 A1 | 7/2006 | Lee et al. |
| 2006/0199778 A1 | 9/2006 | Ellis-Behnke et al. |
| 2006/0211615 A1 | 9/2006 | Zhang et al. |
| 2007/0099840 A1 | 5/2007 | Ulijn |
| 2007/0203062 A1 | 8/2007 | Ellis-Behnke |
| 2007/0287741 A1 | 12/2007 | Herzberg |
| 2008/0032934 A1 | 2/2008 | Ellis-Behnke |
| 2008/0091233 A1 | 4/2008 | Ellis-Behnke et al. |
| 2008/0274979 A1 | 11/2008 | Ellis-Behnke et al. |
| 2009/0111734 A1 | 4/2009 | Ellis-Behnke et al. |
| 2011/0002880 A1 | 1/2011 | Takamura |
| 2011/0201541 A1 | 8/2011 | Takamura |
| 2013/0095060 A1 | 4/2013 | Hsieh |
| 2014/0093473 A1 | 4/2014 | Hauser |
| 2015/0056263 A1 | 2/2015 | Norchi |
| 2015/0218252 A1 | 8/2015 | Ingber |

FOREIGN PATENT DOCUMENTS

| | | |
|---|---|---|
| WO | 9952574 | 2/1999 |
| WO | WO 99/52574 | 10/1999 |
| WO | WO 02/062969 | 8/2002 |
| WO | WO 03/006043 | 1/2003 |
| WO | WO 03/084980 | 10/2003 |
| WO | WO 03/096972 | 11/2003 |
| WO | 2004007532 | 1/2004 |
| WO | WO 2004/007532 | 1/2004 |
| WO | WO 2005/014615 | 2/2005 |
| WO | 2005123760 | 12/2005 |
| WO | 2006036826 | 1/2006 |
| WO | WO 2006/014570 | 2/2006 |
| WO | WO 2006/116524 | 11/2006 |
| WO | 2007142757 | 2/2007 |
| WO | WO 2007/142757 | 12/2007 |
| WO | WO 2008/113030 | 9/2008 |
| WO | 2008134544 | 11/2008 |

OTHER PUBLICATIONS

Bullis, "Nanohealing", *Technology Review*, pp. 1-3 (Mar./Apr. 2007).
Christie, "The nano-knitters", *Popular Science*, pp. 1, accessed Aug. 11, 2006.
Crowston, et al., "New Optic Nerve? International Glaucoma Review", *The Journal for the Glaucoma Society*, (Meeting) Reports, pp. 1-2, (IGR 9-1 Jun. 2007).
Dahlberg, "Surgical discovery promising", *The Sacremento Bee*, pp. 1-3 (Oct. 10, 2006), accessed (Oct. 10, 2006).
Daily India, "Study: Biodegradable liquids halt bleeding", www.dailyindia.com; pp. 1, accessed on Oct. 10, 2006.
Davis, et al., "Injectable self-assembling peptide nanofibers create intramyocardial microenvironments for endothelial cells", *Circulation*, 111(4):442-50 (2005).
Deutschlandfunk, "Liquid Plaster", www.dradio.de; pp. 1-2, (Oct. 11, 2006), accessed (Oct. 12, 2006).
EJ, "Closing the cns gap", *ACS Chemical Biology*, 1(3):117, (2006).
Ellis-Behnke, et al., "Crystal clear surgery with self-assembling molecules that act as a bio barrier in the brain and intetstine", *Nanomedicine: Nanotechnology Biology and Medicine* 1 (3):269-270 (2005).
Ellis-Behnke, et al., "Molecular repair of the brain using self-assembling peptides", *Chim. Oggi.*, 24(4) 42-45 (2006).
Ellis-Behnke, et al., "Molecular Restorstion of the Body: Nano neuro knitting for brain repair", *JEAAM & BAAMJ*, 4:35-37 (2006).
Ellis-Behnke, et al., "Nano hemostat solution: immediate hemostasis at the nanoscale", *Nanomedicine*, 2(4): 207-15 (2006). Epub Oct. 12, 2006.
Ellis-Behnke, et al., "Nano neuro knitting: peptide nanofiber scaffold for brain repair and axon regeneration with functional return of vision", *Proc. Natl. Sci. U.S.A.* Mar. 28, 2006;103(13):5054-9 (2006). Epub Mar. 20, 2006. Erratum in: *Proc. Natl. Acad. Sci. U.S.A.* May 9, 2006;103(19):7530.
Ellis-Behnke, et al., "Nano neuro knitting: peptide nanofiber scaffold for brain repair and axon regeneration with functional return of vision", *Nature Reviews/Neuroscience, Research Highlights*, (7):1 (2006).
Ellis-Behnke, et al., "Using nanotechnology to design potential therapies for CNS regeneration", *Curr. Pharm. Des.*, 13(24):2519-28 (2007).
Fox News, "New peptide salve could replace adhesive bandages", www.foxnews.com, pp. 1, (Oct. 10, 2006), accessed Oct. 10, 2006.
Genove, et al., "The effect of functionalized self assembling peptide scaffolds on human aortic endothelial cell function", *Biomaterials*, 26(16):3341-51 (2005).
Gibian, "Study: Biodegradable liquids halt bleeding", *United Press International*, Oct. 10, 2006.
Gill, "Pour-on nanotechnology stops bleeding in seconds", *Chemistry World*, pp. 1-2, (2006).
Guo, et al., "Reknitting the injured spinal cord by self-assembling peptide nanofiber scaffold", *Nanomedicine*, 3(4):311-21 (2007).
Hampton, et al., "Healing power found in nano knitting", *JAMA*, 3:297(1):31 (2007).
Hartgerink, et al., "Nanomedicine: New material stops bleeding in a hurry", *Nature Nanomedicine*, 1(3): 166-167 (2006).
Iran Daily, "Brain-healing bridges", www.iran-daily.com, pp. 1-2, accessed Apr. 25, 2006.
Kendhale, et al., "Isotactic N-alkyl acrylamide oligomers assume self-assembled sheet structure: first unequivocal evidence from crystal structure", *Chem Comm. (Camb)*, 26:2756-2758 (2006).
Knudsen, "Nanosolution halts bleeding", *Technology Review*, accessed Oct. 10, 2006.
Marks, "Optic nerve regrown", *New Scientist* on www.stemcellschina.com, (Mar. 15, 2006), updated Jun. 29, 2006, accessed Aug. 11, 2006.
MIT News, "MIT material stops bleeding in seconds", www.web.mit.edu, pp. 1-2, Oct. 10, 2006, accessed Jul. 10, 2009.
Moore, et al., "A field guide to foldamers", *Chem. Rev.*, 101(12), 3893-4012 (2001).
Mumbai Mirror, "New Solution to stop bleeding", www.mumbaimirror.com; pp. 1 accessed Oct. 17, 2006.
Nano China, "Stopping Bleeding", www.nanochina.cn, pp. 1-3, (Oct. 27, 2006), accessed Nov. 11, 2006.
Narmoneva, et al., "Self-assembling short oligopeptides and the promotion of angiogenesis", *Biomaterials*, 26(23):4837-46 (2005).
Newindpress, "New nano-gel that stops bleeding within seconds", www.newindpress.com, pp.1, accessed Oct. 11, 2006.
News in Science, "Liquid stops bleeding during surgery", *Reuters*, pp. 1-2, accessed Oct. 10, 2006.
Palmer, "Peptide soup halts blood loss", *Science NOW Daily News*, pp. 1, Oct. 10, 2006.
Penland, "Recently discovered by researchers, a new liquid that can stop bleeding faster than you can slap on a band-aid", *Discover Magazine*, Oct. 19, 2006.
Schneider, et al., "Behavioral testing and preliminary analysis of the hamster visual system", *Nat. Protoc.*, 1(4):1898-905 (2006).
Science, Engineering and Technology, "Nanomaterial stops bleeding in seconds", www.scenta.co.uk, pp. 1-2, accessed Oct. 10, 2006.
Scientific American, "Protein gel stops bleeding in unknown way", www.sciam.com, pp. 1-2, accessed on Oct. 10, 2006.
Scrivener, "Bleeding? Here's a simple solution", Toronto Star, (Oct. 15, 2006).
Teather, et al., "Differential induction of c-Jun and Fos-like proteins in rat hippocampus and dorsai striatum after training in two water maze tasks", *Neurobiol. Learn Mem.*, 84(2):75-84 (2005).

(56) References Cited

OTHER PUBLICATIONS

Thomas, et al., "Nano neuro knitting repairs injured brain", Lancet. Neurol., 5(5):386 (2006).
Trafton, et al., "New material halts bleeding", *MIT Tech Talk*, 51(5):1-3 (2006).
Tu and Tirrell, "Bottom-up design of biomometic assemblies", *Adv. Drug Deliv. Rev.*, 56(11): 1537-63 (2004).
Whats Next In Science & Technology, "Biodegradable liquids can stop bleeding almost instantly—could significantly impact medicine", (Oct. 10, 2006), accessed Oct. 15, 2006.
Wilson, "Nano neuro-kit", *Drug Discovery & Development*, accessed Sep. 22, 2006.
Yung, et al., "Scientists discover new way to control bleeding", *The Standard*, pp. 1-2, (Oct. 11, 2006), accessed Oct. 10, 2006.
Zhang, et al., "Designer self-assembling peptide nanofiber for 3D tissue cell cultures", *Semin. Cancer Biol.*, 15(5):413-20 (2005).
Benita, et al., "Characterization of drug-loaded poly(d,l-lactide) microspheres", *J. Pharm. Sci.*, 73(12):1721-4 (1984).
Caplan, et al., "Self assembly of a beta-sheet protein governed by relief of electrostatic repulsion relative to van der Waals attraction", *Biomacromolecules*, 1(4):627-31 (2000).
Caplan, et al., "Control of self-assembling oligopeptide matrix formation through systematic variation of amino acid sequence", *Biomaterials*, 23(1):219-27 (2002).
Frechet, "Dendrimers and supramolecular chemistry", *Proc. Natl. Acad. Sci. U.S.A.*, 99(8):4782-7 (2002).
Hill, et al., "A field guide to foldamers", *Chem. Rev.*, 101(12):3893-4012 (2001).
Holmes, et al., "Extensive neurite outgrowth and active synapse formation on self-assembling peptide scaffolds", *Proc. Natl. Acad. Sci. U.S.A.*, 97(12):6728-33 (2000).
Leon, et al., "Mechanical properties of a self-assembling oligopeptide matrix", *J. Biomater. Sci. Polym. Ed.*, 9(3):297-312 (1998).
Ma, et al., "Supramolecular polymer chemistry: self assembling dendrimers using the DDA.AAD (GC-like) hydrogen bonding motif", *J. Am. Chem. Soc.*, 124(46):13757-69 (2002).
Mathiowitz and Langer, "Polyanhydride microspheres as drug carriers I. Hot-melt microencapsulation", *J. Controlled Release*, 5(1):13-22 (1987).
Mathiowitz, et al., "Morphology of polyanhydride microsphere delivery systems", *Scanning Microscopy*, 4(2):328-340 (1990).
Mathiowitz, et al., "Novel microphones for delivery systems", *Reactive Polymers*, 6:275-83 (1987).
Mathiowitz, et al., "Polyhydride microspheres as drug carriers. 2. microencapsulation by solvent removal", *J. Appl. Polymer Sci.*, 35, 755-774 (1988).
Mathiowitz, et al., "Polyanhydride microspheres. IV: Morphology and characterization of systems made by spray drying", *J. Appl. Polymer Sci.*, 45:125-134 (1992).
Sawhney, et al., "Bioerodible hydrogels based on photopolymerized poly(ethylene glycol)-co-poly(α-hydroxy acid) diacrylate macromers", *Macromolecules*, 26(4):581-587 (1993).

Zhang, et al., "Peptide self assembly in functional polymer science and engineering", Reactive & Functional Polymers, 41, 91-102 (1999).
Zhang, et al., "Self-complementary oligopeptide matrices support mammalian cell attachment", *Biomaterials*, 16(18):1385-93 (1995).
Zhang, et al., "Spontaneous assembly of a self-complementary oligopeptide to form a stable macroscopic membrane", *Proc. Natl. Acad. Sci. U.S.A.*, 90(8):3334-8 (1993).
Zimmerman, et al., "Self-assembling dendrimers", *Science*, 271(5252):1095-8 (1996).
Ahmad, et al., "A novel hybrid system for the fabrication of a fibrous mesh with micro-inclusions", Carbohydr Polym., 89(1):222-9 (2012).
Brun, et al., "Electrospun scaffolds of self-assembling peptides with poly (ethylene oxide) for bone tissue engineering", Acta Biomater., 7:2526-32 (2011).
Chen, et al., "A hybrid silk/RADA-Based fibrous scaffold with triple hierarch for ligament regeneration", Tissue Eng, 18(13-14):1399-409 (2012).
Conform, definition from http://www.merriam-webster.com/dictionary/conform, pp. 1-2. accessed 08-0409.
Ellis-Behnke, "Nano neuro knitting: peptide nanofiber scaffold for brain repair and axon regeneration with functional return of vision", Nature Reviews/Neuroscience, Research Highlights, (7):1 (2006).
Endometriosis, Merck Manual Professional, pp. 1-5, www.merck.com accessed Aug. 4, 2009.
Intestinal Obstruction, Merck Manual Professional, pp. 1-4. www.merck.com accessed Aug. 4, 2009.
Keloid and Hypertrophic Scar: Treatment & Medication, from, http://emedicine.medscape.com|article11057599-treatment, pp. 1-16, accessed Aug. 4, 2009.
Keloids, Merc Manual Professional, pp. 1, www.merck.com access Aug. 4, 2009.
Khadka and Hayne, "Protein- and peptide-based electrospun nanofibers in medical biomaterials", Nanomedicine, 8:1242-62 (2012).
Mishra, et al., "Ultrasmall natural peptides self-assemble to strong temperature-resistant helical fibers in scaffolds suitable for tissue engineering", Nano Today, 6(3):232-9 (2011).
Nguyen and Lee, "The effect of cross-linking on the microstructure, mechanical properties and biocompatibility of electrospun polycaprolactone-gelatin/PLGA-gelatin/PLGA-chitosan hybrid composite", Sci. Technol. Adv. Mater., 13:035002 (2012).
Osterman, et al., "Design and characterization of peptides with amphiphilic$^2$-strand structures", J Cellular Biochem., 29:57-72 (1985). vbTab.
Residue, definition from http://dictionary.reference.com|browse|residue, pp. 1-4. accessed Jul. 13, 2009.
Sawhney, "Bioerodible hydrogels based on photopolymerized poly-ethylene glycol)-co-poly(ahydroxy acid) diacrylatemacromers", Macromolecules, 26(4):581-587 (1993).
Tubal Dysfunction and Pelvic Lesions, Merck Manual Professional, pp. 1.2, www.merck.com accessed Aug. 4, 2009.

\* cited by examiner

COMPOSITIONS FOR PREVENTION OF ADHESIONS AND OTHER BARRIER APPLICATIONS

CROSS-REFERENCE TO RELATED APPLICATIONS

This application is a divisional application of U.S. Ser. No. 11/740,284, filed on Apr. 25, 2007, which claims the benefit of and priority to U.S. Ser. No. 60/745,601, filed on Apr. 25, 2006; U.S. Ser. No. 11/740,284 is a continuation-in-part of U.S. Ser. No. 11/411,745, filed on Apr. 25, 2006, which claims the benefit of and priority to U.S. Ser. No. 60/758,827 filed on Jan. 13, 2006 and U.S. Ser. No. 60/674,612 filed on Apr. 25, 2005.

REFERENCE TO SEQUENCE LISTING

The Sequence Listing submitted Sep. 7, 2007 as a text file named "CNS_102_ST25.txt," created on Jul. 6, 2007, and having a size of 91,000 bytes is hereby incorporated by reference pursuant to 37 C.F.R. §1.52(e)(5).

FIELD OF THE INVENTION

The present invention is generally in the field of formulations for application to tissues for prevention of adhesions and other barrier applications.

BACKGROUND OF THE INVENTION

Adhesions may be present at birth (congenital) or may form after abdominal surgery or inflammation. Most form after surgery. Adhesions are more common after procedures on the colon, appendix, or uterus than after surgery on the stomach, gall bladder, or pancreas. The risk of developing adhesions increases with the passage of time after the surgery.

Abdominal adhesions are bands of fibrous scar tissue that form on organs in the abdomen, causing the organs to stick to one another or to the wall of the abdomen. Intestinal adhesions are bands of fibrous tissue that connect the loops of the intestines to each other, or the intestines to other abdominal organs, or the intestines to the abdominal wall. These bands can pull sections of the intestines out of place and may block passage of food. In people living in developed countries, this scar tissue most commonly develops after abdominal surgery, in which organs are handled by the surgical team and are shifted temporarily from their normal positions. It can also form in people who develop peritonitis, an infection that has spread to the membrane that covers the abdominal organs. Peritonitis commonly occurs after appendicitis or other abdominal infections. Another cause of adhesions is endometriosis, an inflammatory condition that affects some women and may involve the abdomen and serious abdominal trauma, including cesarean sections.

Adhesions are a major cause of intestinal obstruction. If the adhesions cause partial or complete obstruction of the intestines, the symptoms exhibited depend on the degree and the location of the obstruction. They include cramps, abdominal pain, vomiting, bloating, an inability to pass gas, and constipation. In a small number of people who have adhesions, however, the fibrous bands of scar tissue block the intestines either completely or partially. This blockage is called a bowel obstruction, and leads to death in about 5% of cases. Sometimes, an area of intestine that is affected by adhesions can become blocked then unblocked, causing symptoms to come and go. In about 10% of small-bowel obstructions, a portion of the bowel twists tightly around a band of adhesions. This cuts off the normal blood supply to the twisted bowel, a disorder known as strangulation, causing that section of bowel to die. When this emergency happens, the person must undergo surgery immediately. The death rate is as high as 37% in people who develop strangulation.

Percutaneous epidural adhesiolysis and spinal endoscopic adhesiolysis are interventional pain management techniques used to treat patients with refractory low back pain due to epidural scarring. Standard epidural steroid injections are often ineffective, especially in patients with prior back surgery. Adhesions in the epidural space can prevent the flow of medicine to the target area; lysis of these adhesions can improve the delivery of medication to the affected areas, potentially improving the therapeutic efficacy of the injected medications. Prevention of such adhesions would be more preferable.

Many different materials have been tried as a means of preventing adhesions. Most of these are hydrogels that are applied as solutions at the time of surgery. Efficacy of these materials has varied due to rapid degradation and/or failure to form a sufficiently thick barrier. Others materials work only in combination with anti-proliferative drugs. None of these materials has been shown to be effective work in a highly fluid environment, which usually is present during surgery due to bleeding and leakage of other bodily fluids.

It is therefore an object of the present invention to provide methods and compositions for preventing or minimizing adhesions and for other barrier applications which can be applied to tissues or cells which are bleeding or in the presence of fluids.

It is another object of the present invention to provide such a composition that can be formulated as a bandage, spray, coating, or powder.

It is a still further object of the present invention to provide a composition that can be used to retain fluids or cells but is sufficiently clear to allow a physician to see and work through the material.

BRIEF SUMMARY OF THE INVENTION

Compositions including materials which self-assemble under physiological conditions are formulated for application to tissues for prevention of adhesions or other barrier applications, such as minimizing contamination or infection, limiting spread of metastasis following cancer surgery, or for delivery of a therapeutic, diagnostic or prophylactic agent in a confined area, after bleeding or fluid leakage has been substantially stopped. In one embodiment, the self-assembling material comprises peptides having a sequence of amino acid residues conforming to one or more of Formulas I-IV: $((Xaa^{o'}\text{-}Xaa+)x(Xaane1\_Xaa-)y)n$ (I); $((Xaa'\_Xaa)x(Xaa°e°\text{-}Xaa+)y)n$ (II); $((Xaa+\text{-}Xaa"e1)x(Xaa\text{-}Xaa")y)n$ (III); and $((Xaa\text{-}XaaQe7)x(Xaa+Xaa1e")\ y)n$ (IV), where Xaan' represents an amino acid residue having a neutral charge; Xaa+ represents an amino acid residue having a positive charge; Xaa represents an amino acid residue having a negative charge; x and y are integers having a value of 1, 2 or 4, independently; and n is an integer having a value of 1-5. In another embodiment, the self assembling materials are peptidomimetics, nucleotidomimetics, di- and triblock copolymers, N-alkylacrylamides, or dendimers. These materials are also useful in a method for regeneration or repair of tissue or cells forming tissue.

The concentration of the self-assembling materials in any given formulation can vary and can be between approximately 0.1% and 99%, inclusive, preferably between 0.1% and 10%. In one embodiment, the concentration of the self-assembling materials (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling materials can be higher in stock solutions and in solid (e.g., powdered) formulations. Solid preparations may have a concentration of self-assembling materials approaching 100% (e.g., the concentration of self-assembling materials can be 95, 96, 97, 98, 99% or more (e.g., 99.99%) of the composition). Whether in liquid or solid form, the materials can be brought to the desired concentration prior to use by addition of a pharmaceutically acceptable diluent (e.g. deionized water), fillers, or oil. The formulations may include a pharmaceutically acceptable carrier or therapeutic, prophylactic or diagnostic agents. These include, but are not limited to, antiinflammatories, vasoactive agents, anti-infectives, anesthetics, growth factors, and/or cells. Metals may be added as chelators or to further decrease adhesion.

The formulation can be administered as appropriate for treatment of one or more disorders or conditions, such as those noted above. For example, the formulation may be applied after repair of an injury or during surgery of the lung, eye or dura, or following an epidural or spinal tap, to prevent or minimize formation of adhesions. The formulation may be administered to a burn or ulcer, after bleeding or fluid loss is stopped.

The formulation may be applied as a hydrogel, laminate including oil, or spray. In one embodiment, the formulation is provided as a dry or lyophilized powder which can be administered directly as a powder or a tablet, disc, or wafer which hydrates at the site of application, or suspended or dissolved in a liquid, most preferably aqueous, and applied as a spray, paint, injection or a hydrogel including a material such as chitin, collagen, alginate, or synthetic polymer. In the preferred embodiment, the material is provided in combination with an oil, and forms a laminate. In yet another embodiment, the formulation is provided in a bandage, foam or matrix, in which the materials may be dispersed or absorbed. The formulation could also be in the form of sutures, tape, or adhesive. The liquid formulations may be provided in a syringe or pipette having a barrel containing a composition including self-assembling materials and a means for expelling the composition from an open tip of the syringe or pipette (e.g., a plunger or bulb). The syringe may consist of one or more compartments, so that mixing of the self-assembling materials with one or more other agents occurs at the time of application. The compartments may also contain excipients such as a material forming a hydrogel or adhesive in one compartment and the self-assembling materials in the other compartment. In another embodiment, one compartment may contain lyophilized or particles of self-assembling materials, and another compartment may contain solution to dissolve or hydrate the materials, or mixed with other powders for dry application. The liquid and powder compositions are stable, preferably for a period greater than one year, more preferably greater than two years and most preferably greater than three years.

One or more of the compositions described herein can be assembled in kits, together with instructions for use. For example, the kits can include a biocompatible composition including self-assembling materials (or a concentrated solution or powdered formulation thereof, together with a diluent) and a vasoconstrictor, a coloring agent, or an analgesic or anesthetic agent and instructions for their combination (if not already combined) and use (e.g., dilution and administration). The kits can further include one or more of the additional agents described herein. These agents can be present within the self assembling composition or packaged separately, and they can include one or more types of biological cells, an antibiotic or other therapeutic, collagen, an anti-inflammatory agent, a growth factor, or a nutrient. The kit may also include one or more of a syringe (e.g., a barrel syringe or a bulb syringe), a needle, a pipette, gauze, sponges, cotton, swabs, a bandage, a disinfectant, surgical thread, scissors, a scalpel, a sterile fluid, a spray canister, including those in which a liquid solution is sprayed through a simple hand pump, a sterile container, or disposable gloves.

DETAILED DESCRIPTION OF THE INVENTION

I. Formulations

"Biocompatible", as used herein, refers to compatibility with living tissue or a living system by not being toxic, injurious, or physiologically reactive and not causing immunological rejection.

"Complementary" means having the capability of forming ionic or hydrogen bonding interactions between hydrophilic residues from adjacent peptides in a structure. Each hydrophilic reside in a peptide either hydrogen bonds or ionically pairs with a hydrophilic residue on an adjacent peptide, or is exposed to solvent. Pairing may also involve van der Waals forces.

"Effective amount", in reference to an active agent such as a self-assembling peptide or biomolecule, pharmaceutical agent, etc. refers to the amount necessary to elicit a desired biological response. As will be appreciated by those of ordinary skill in this art, the effective amount of an agent may vary depending on such factors as the desired biological endpoint, the agent to be delivered, the nature of the site to which the agent is delivered, the nature of the conditions for which the agent is administered, etc. For example, the effective amount of a composition for treatment of diabetic retinopathy may be an amount sufficient to promote recovery to a greater extent than would occur in the absence of the composition.

"Hemostasis" refers to the cessation of bleeding.

"Preventing" refers to causing a condition, state, or disease, or symptom or manifestation of such, or worsening of the severity of such, not to occur. Preventing includes reducing the risk that a condition, state, or disease, or symptom or manifestation of such, or worsening of the severity of such, will Occur.

"Repair", as sued in reference to the repair of tissue in various embodiments of the invention, may include any aspect of anatomical or functional restoration of the condition of the tissue prior to an injury, deterioration, or other damage. For example, it may include restoration of physical continuity between portions of tissue that were separated by injury, deterioration, or other damage. Preferably such restoration of physical continuity includes reposition or reconnection of the portions of tissue without appreciable separation by tissue of a type that was not present prior to the injury, such as scar tissue. Repair may, but need not, include growth or development of new tissue. "Repair" and "Healing" are used interchangeably herein.

II. Self-Assembling Materials

A. Self-Assembling Peptides

In one embodiment, the self-assembling material is a self-assembling peptide. The term "peptide," as used herein includes "polypeptide," "oligopeptide," and "protein," and refers to a chain of at least two α-amino acid residues linked together by covalent bonds (e.g., peptide bonds). Useful peptides can vary in length so long as they retain the ability to self-assemble to an extent useful for one or more of the purposes described herein. The number of amino acid residues in the peptide may range from as few as two α-amino acid residues to about 200 residues. Typically, peptides which self-assemble have from about 6 to about 200 residues, preferably from about 6 to about 64 residues, more preferably from about 8 to about 36 residues, most preferably from about 8 to about 24 residues. The peptides can be at least eight amino acids in length (e.g., eight or 10 amino acids), at least 12 amino acids in length (e.g., 12 or 14 amino acids), or at least 16 amino acids in length (e.g., 16, 18, 20, 22, or 24 amino acids). Peptides that are less than 100 amino acid residues long, more preferably less than approximately 50 amino acids in length, may assemble more readily. In one embodiment, the peptide has from about 8 to about 16 residues. In another embodiment, the peptide has from about 12 to about 20 residues. In yet another embodiment, the peptide has from about 16 to about 20 residues. "Peptide" may refer to an individual peptide or to a collection of peptides having the same or different sequences, any of which may contain naturally occurring α-amino acid residues, non-naturally occurring α-amino acid residues, and combinations thereof α-Amino acid analogs are also known in the art and may alternatively be employed. In particular, D-α-amino acid residues may be used.

In addition, one or more of the amino acid residues in a self-assembling peptide can be altered or derivatized by the addition of one or more chemical entities including, but not limited to, acyl groups, carbohydrate groups, carbohydrate chains, phosphate groups, farnesyl groups, isofarnesyl groups, fatty acid groups, or a linker which allows for conjugation or functionalization of the peptide.

While the sequences of the peptides can vary, useful sequences include those that convey an amphiphilic nature to the peptides (e.g., the peptides can contain approximately equal numbers of hydrophobic and hydrophilic amino acid residues), and the peptides can be complementary and structurally compatible. Complementary peptides have the ability to form ionic or hydrogen bonds between residues (e.g., hydrophilic residues) on adjacent peptides in a structure. For example, one or more hydrophilic residues in a peptide can either hydrogen bond or ionically pair with one or more hydrophilic residues on an adjacent peptide. Unpaired residues can interact (e.g. form hydrogen bonds, etc,) with the solvent. Peptide-peptide interactions may also involve van der Waals forces and/or forces that do not constitute covalent bonds. The peptides are structurally compatible when they are capable of maintaining a sufficiently constant intrapeptide distance to allow self-assembly and structure formation. The intrapeptide distance can vary. "Intrapeptide distance", as used herein, refers to the average of a representative number of distances between adjacent amino acid residues. In one embodiment, the intrapeptide distance is less than about 4 angstroms, preferably less than about 3, more preferably less than about 2 angstroms, and most preferably less than about 1 angstrom. The intrapeptide distance may be larger than this, however. These distances can be calculated based on molecular modeling or based on a simplified procedure described in U.S. Pat. No. 5,670,483 to Zhang et al.

Where self-assembling peptides are used, it is thought that their side chains (or R groups) partition into two faces, a polar face with positively and/or negatively charged ionic side chains, and a nonpolar face with side chains that are considered neutral or uncharged at physiological pH (e.g., the side chain of an alanine residue or residues having other hydrophobic groups). The positively charged and negatively charged amino acid residues on the polar face of one peptide can form complementary ionic pairs with oppositely charged residues of another peptide. These peptides may therefore be called ionic, self-complementary peptides. If the ionic residues alternate with one positively and one negatively charged residue on the polar face (−+−+−+−+), the peptides may be described as "modulus I;" if the ionic residues alternate with two positively and two negatively charged residues (−−++−−++) on the polar face, the peptides are described as "modulus II;" if the ionic residues alternate with three positively and three negatively charged residues (+++−−−+++−−−) on the polar face, the peptides are describe as "modulus III;" if the ionic residues alternate with four positively and four negatively charged residues (++++−−−−++++−−−−) on the polar face, they are described as "modulus IV." A peptide having four repeating units of the sequence EAKA (SEQ ID NO: 2) may be designated EAKA16-I, and peptides having other sequences may be described by the same convention.

Peptide-based structures can be formed of heterogeneous mixtures of peptides (i.e., mixtures containing more than one type of peptide conforming to a given formula or to two or more of the formulas). In some embodiments, each of the types of peptides in the mixture are able to self-assemble alone. In other embodiments, one or more of each type of peptide would not, alone, self-assemble but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides which are complementary and structurally compatible to each other, can be used. The compositions described herein regardless of the precise form (e.g., whether in a liquid form or molded) and regardless of the overall compositions (e.g., whether combined with another agent, contained within a device, or packaged in a kit) can include a mixture of one or more peptide chains.

Either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group ($NH_2$) can be used to neutralize an "extra" negative charge that may otherwise be present at the C-terminus (e.g., a charge not resulting from the side chain of the C-terminal amino acid residue). Where an amine is used, the C-terminus would bear an amide (—$CONH_2$). The neutralization of charges on a terminus may facilitate self-assembly. One of ordinary skill in the art will be able to select other suitable groups.

Useful peptides can also be branched, in which case they will contain at least two amino acid polymers, each of which consists of at least three amino acid residues joined by peptide bonds. The two amino acid polymers may be linked by a bond other than a peptide bond.

The structures described herein can be formed through self-assembly of the peptides described in U.S. Pat. Nos. 5,670,483; 5,955,343; 6,548,630; and 6,800,481 to Zhang et al.; Holmes et al., *Proc. Natl. Acad. Sci. USA*, 97:6728-6733 (2000); Zhang et al., *Proc. Nati. Acad. Sci. USA*, 90:3334-3338 (1993); Zhang et al., *Biomaterials*, 16:1385-1393 (1995); Caplan et al., *Biomaterials*, 23:219-227 (2002); Leon et al., *J. Biomater. Sci. Polym. Ed.*, 9:297-312 (1998); and Caplan et al., *Biomacromolecules*, 1:627-631 (2000).

Self-assembling peptides containing alternating hydrophobic and hydrophilic amino residues can be used. Examples of representative hydrophobic and hydrophilic peptides are listed in Table 1.

TABLE 1

Representative Self-Assembling Peptides

| No. | Sequence (N → C) | |
|---|---|---|
| 1. | n-SGSGSGSGSGSGSGSG-c | (SEQ ID NO: 3) |
| 2. | n-SASASASASASASASA-c | (SEQ ID NO: 4) |
| 3. | n-SVSVSVSVSVSVSVSV-c | (SEQ ID NO: 5) |
| 4. | n-SLSLSLSLSLSLSLSL-c | (SEQ ID NO: 6) |
| 5. | n-SISISISISISISISI-c | (SEQ ID NO: 7) |
| 6. | n-SMSMSMSMSMSMSMSM-c | (SEQ ID NO: 8) |
| 7. | n-SFSFSFSFSFSFSFSF-c | (SEQ ID NO: 9) |
| 8. | n-SWSWSWSWSWSWSWSW-c | (SEQ ID NO: 10) |
| 9. | n-SPSPSPSPSPSPSPSP-c | (SEQ ID NO: 11) |
| 10. | n-TGTGTGTGTGTGTGTG-c | (SEQ ID NO: 12) |
| 11. | n-TATATATATATATATA-c | (SEQ ID NO: 13) |
| 12. | n-TVTVTVTVTVTVTVTV-c | (SEQ ID NO: 14) |
| 13. | n-TLTLTLTLTLTLTLTL-c | (SEQ ID NO: 15) |
| 14. | n-TITITITITITITITI-c | (SEQ ID NO: 16) |
| 15. | n-TMTMTMTMTMTMTMTM-c | (SEQ ID NO: 17) |
| 16. | n-TFTFTFTFTFTFTFTF-c | (SEQ ID NO: 18) |
| 17. | n-TWTWTWTWTWTWTWTW-c | (SEQ ID NO: 19) |
| 18. | n-TPTPTPTPTPTPTPTP-c | (SEQ ID NO: 20) |
| 19. | n-CGCGCGCGCGCGCGCG-c | (SEQ ID NO: 21) |
| 20. | n-CACACACACACACACA-c | (SEQ ID NO: 22) |
| 21. | n-CVCVCVCVCVCVCVCV-c | (SEQ ID NO: 23) |
| 22. | n-CLCLCLCLCLCLCLCL-c | (SEQ ID NO: 24) |
| 23. | n-CICICICICICICICI-c | (SEQ ID NO: 25) |
| 24. | n-CMCMCMCMCMCMCMCM-c | (SEQ ID NO: 26) |
| 25. | n-CFCFCFCFCFCFCFCF-c | (SEQ ID NO: 27) |
| 26. | n-CWCWCWCWCWCWCWCW-c | (SEQ ID NO: 28) |

TABLE 1-continued

Representative Self-Assembling Peptides

| No. | Sequence (N → C) | |
|---|---|---|
| 27. | n-CPCPCPCPCPCPCPCP-c | (SEQ ID NO: 29) |
| 28. | n-YGYGYGYGYGYGYGYG-c | (SEQ ID NO: 30) |
| 29. | n-YAYAYAYAYAYAYAYA-c | (SEQ ID NO: 31) |
| 30. | n-YVYVYVYVYVYVYVYV-c | (SEQ ID NO: 32) |
| 31. | n-YLYLYLYLYLYLYLYL-c | (SEQ ID NO: 33) |
| 32. | n-YIYIYIYIYIYIYIYI-c | (SEQ ID NO: 34) |
| 33. | n-YMYMYMYMYMYMYMYM-c | (SEQ ID NO: 35) |
| 34. | n-YFYFYFYFYFYFYFYF-c | (SEQ ID NO: 36) |
| 35. | n-YWYWYWYWYWYWYWYW-c | (SEQ ID NO: 37) |
| 36. | n-YPYPYPYPYPYPYPYP-c | (SEQ ID NO: 38) |
| 37. | n-NGNGNGNGNGNGNGNG-c | (SEQ ID NO: 39) |
| 38. | n-NANANANANANANANA-c | (SEQ ID NO: 40) |
| 39. | n-NVNVNVNVNVNVNVNV-c | (SEQ ID NO: 41) |
| 40. | n-NLNLNLNLNLNLNLNL-c | (SEQ ID NO: 42) |
| 41. | n-NININININININI-c | (SEQ ID NO: 43) |
| 42. | n-NMNMNMNMNMNMNMNM-c | (SEQ ID NO: 44) |
| 43. | n-NFNFNFNFNFNFNFNF-c | (SEQ ID NO: 45) |
| 44. | n-NWNWNWNWNWNWNWNW-c | (SEQ ID NO: 46) |
| 45. | n-NPNPNPNPNPNPNPNP-c | (SEQ ID NO: 47) |
| 46. | n-QGQGQGQGQGQGQGQG-c | (SEQ ID NO: 48) |
| 47. | n-QAQAQAQAQAQAQAQA-c | (SEQ ID NO: 49) |
| 48. | n-QVQVQVQVQVQVQVQV-c | (SEQ ID NO: 50) |
| 49. | n-QLQLQLQLQLQLQLQL-c | (SEQ ID NO: 51) |
| 50. | n-QIQIQIQIQIQIQIQI-c | (SEQ ID NO: 52) |
| 51. | n-QMQMQMQMQMQMQMQM-c | (SEQ ID NO: 53) |
| 52. | n-QFQFQFQFQFQFQFQF-c | (SEQ ID NO: 54) |
| 53. | n-QWQWQWQWQWQWQWQW-c | (SEQ ID NO: 55) |
| 54. | n-QPQPQPQPQPQPQPQP-c | (SEQ ID NO: 56) |

Other useful self-assembling peptides can be generated, for example, which differ from those exemplified by a single amino acid residue or by multiple amino acid residues (e.g., by inclusion or exclusion of a repeating quartet). For example, one or more cysteine residues may be incorporated into the peptides, and these residues may bond with one another through the formation of disulfide bonds. Structures bonded in this manner may have increased mechanical strength relative to structures made with comparable peptides that do not include cysteine residues and thus are unable to form disulfide bonds.

The amino acid residues in the self-assembling peptides can be naturally occurring or non-naturally occurring amino acid residues. Naturally occurring amino acids can include amino acid residues encoded by the standard genetic code as well as non-standard amino acids (e.g., amino acids having the D-configuration instead of the L-configuration), as well as those amino acids that can be formed by modifications of standard amino acids (e.g. pyrrolysine or selenocysteine). Non-naturally occurring amino acids are not been found in nature, but can be incorporated into a peptide chain. Suitable non-naturally occurring amino acids include, but are not limited to, D-alloisoleucine(2R,3S)-2-amino-3-methylpentanoic acid, L-cyclopentyl glycine (S)-2-amino-2-cyclopentyl acetic acid. Other examples of non-naturally occurring amino acids can be found in textbooks or on the worldwide web (e.g., a site is maintained by the California Institute of Technology which displays structures of non-natural amino acids that have been successfully incorporated into functional proteins). Non-natural amino acid residues and amino acid derivatives described in U.S. Patent Application Publication No. 2004/0204561 to Ellison.

Self-assembling peptides can be chemically synthesized or purified from natural or recombinantly-produced sources by methods well known in the art. For example, peptides can be synthesized using standard f-moc chemistry and purified using high pressure liquid chromatography (HPLC).

Self-complementary peptides such as EAKA16-I, RADA16-I (SEQ ID NO: 1), RAEA16-I, and KADA16-I are described in Zhang, S., et al. ((1999) Peptide self-assembly in functional polymer science and engineering. Reactive & Functional Polymers, 41, 91-102). The self-assembling peptides comprise a sequence of amino acid residues conforming to one or more of Formulas I-IV:

$$((Xaa^{neu}\text{-}Xaa^+)_x(Xaa^{neu}\text{-}Xaa^-)_y)_n \qquad (I)$$

$$((Xaa^{neu}\text{-}Xaa^-)_x(Xaa^{neu}\text{-}Xaa)_y)_n \qquad (II)$$

$$((Xaa^+\text{-}Xaa^{neu})_x(Xaa^-\text{-}Xaa^{neu})_y)_n \qquad (III)$$

$$((Xaa^-\text{-}Xaa^{neu})_x(Xaa^+\text{-}Xaa^{neu})_y)_n \qquad (IV)$$

$Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2, 3, or 4, independently; and n is an integer having a value of 1-5. Peptides with modulus I (i.e., peptides having alternate positively and negatively charged R groups on one side (e.g., the polar face of the β-sheet) are described by each of Formulas I-IV, where x and y are 1. Peptides of modulus II (i.e., peptides having two residues bearing one type of charge (e.g., a positive charge) followed by two residues bearing another type of charge (e.g., a negative charge)) are described by the same formulas where both x and y are 2. Examples of peptides of modulus III (i.e. peptides having three residues bearing one type of charge (e.g., a positive charge) followed by three residues bearing another type of charge (e.g., a negative charge)) include, but are not limited to, RARARADADADA (SEQ ID NO: 57).

Other hydrophilic residues that form hydrogen bonds including, but not limited to, asparagine and glutamine, may be incorporated into the peptides. If the alanine residues in the peptides are changed to more hydrophobic residues, such as leucine, isoleucine, phenylalanine or tyrosine, the resulting peptides have a greater tendency to self-assemble and form peptide matrices with enhanced strength. Some peptides that have similar amino acids compositions and lengths as the peptides described here form alpha-helices and random-coils rather than beta-sheets and do not form macroscopic structures. Thus, in addition to self-complementarity, other factors are likely to be important for the formation of macroscopic structures, such as the peptide length, the degree of intermolecular interaction, and the ability to form staggered arrays.

Self-assembled structures can be formed that have varying degrees of stiffness or elasticity. The structures typically have a low elastic modulus (e.g., a modulus in the range of 1-10 kPa as measured by standard methods, such as in a standard cone-plate rheometer). Low values may be preferable, as they permit structure deformation as a result of movement, in response to pressure, in the event of cell contraction. More specifically, stiffness can be controlled in a variety of ways, including by changing the length, sequence, and/or concentration of the precursor molecules (e.g., self-assembling peptides). Other methods for increasing stiffness can also be employed. For example, one can attach, to the precursors, biotin molecules or any other molecules that can be subsequently cross-linked or otherwise bonded to one another. The molecules (e.g., biotin) can be included at an N- or C-terminus of a peptide or attached to one or more residues between the termini. Where biotin is used, cross-linking can be achieved by subsequent addition of avidin. Biotin-containing peptides or peptides containing other cross-linkable molecules are within the scope of the present invention. For example, amino acid residues with aromatic rings may be incorporated and cross-linked by exposure to UV light. The extent of crosslinking can be precisely controlled by applying the radiation for a predetermined length of time to peptides of known sequence and concentration. The extent of crosslinking can be determined by light scattering, gel filtration, or scanning electron microscopy using standard methods. Furthermore, cross-linking can be examined by HPLC or mass spectrometry analysis of the structure after digestion with a protease, such as matrix metalloproteases. Material strength may be determined before and after cross-linking Regardless of whether cross-linking is achieved by a chemical agent or light energy, the molecules may be cross-linked in the course of creating a mold or when peptide-containing solutions are applied to the body.

The half-life (e.g., the in vivo half-life) of the structures can also be modulated by incorporating protease or peptidase cleavage sites into the precursors that subsequently form a given structure. Proteases or peptidases that occur naturally in vivo or that are introduced (e.g., by a surgeon) can then promote degradation by cleaving their cognate substrates.

Combinations of any of the modifications described here can be made. For example, self-assembling peptides that include a protease cleavage site and a cysteine residue and/or a cross-linking agent, kits and devices containing them, and methods of using them can be utilized.

The peptide structures formed from any self-assembling peptides made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in the peptide structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade. These methods allow one of ordinary skill in the art to determine which of the various alternatives and peptides described herein are most suitable for use in the various methods, and allow optimization of the various processes.

In another embodiment, the self-assembling materials can anchor or interact with the structural extracellular matrix (ECM) at the edges of blood vessels and/or tissues are described herein. These self-assembling materials typically have hydrophobic and/or hydrophilic sections which allow the material to react or interact with the glycoproteins found in the ECM.

Preferably, the self-assembling materials when they break down, do not cause any secondary toxicity. Further, the break down product of the self-assembling materials would be suitable for the growth and repair of the surrounding tissues.

Peptidomimetics

Another class of materials that can self assemble are peptidomimetics. Peptidomimetics, as used herein, refers to molecules which mimic peptide structure. Peptidomimetics have general features analogous to their parent structures, polypeptides, such as amphiphilicity. Examples of such peptidomimetic materials are described in Moore et al., Chem. Rev. 101(12), 3893-4012 (2001).

The peptidomimetic materials can be classified into four categories: α-peptides, β-peptides, γ-peptides, and δ-peptides. Copolymers of these peptides can also be used.

Examples of α-peptide peptidomimetics include, but are not limited to, N,N'-linked oligoureas, oligopyrrolinones, oxazolidin-2-ones, azatides and azapeptides.

Examples of β-peptides include, but are not limited to, β-peptide foldamers, α-aminoxy acids, sulfur-containing β-peptide analogues, and hydrazino peptides.

Examples of γ-peptides include, but are not limited to, γ-peptide foldamers, oligoureas, oligocarbamates, and phosphodiesters.

Examples of δ-peptides include, but are not limited to, alkene-based δ-amino acids and carbopeptoids, such as pyranose-based carbopeptoids and furanose-based carbopeptoids.

Backbones which can Adopt Helical or Sheet Conformations

Another class of compounds that self assemble includes oligomers having backbones which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo(pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as olihothiophenes with chiral p-phenyl-oxazoline side chains, and oligo(m-phenylene-ethynylene)s.

Examples of compound containing backbones utilizing hydrogen bonding interactions include, but are not limited to, aromatic amide backbones such as oligo(acylated 2,2'-bipyridine-3,3'-diamine)s and oligo(2,5-bis[2-aminophenyl] pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-pheylene ethynylene)s containing metal-coordinating cyano groups, and hexapyrrins.

Nucleotidomimetics

Another class of molecules which can self assemble are nucleotidomimetics such as isomeric oligonucleotides, modified carbohydrates, nucleotides with modified nucleotide linkages, and nucleotides with alternative nucleobases.

Examples of isomeric nucleotides include, but are not limited to, iso-RNA and iso-DNA and α-DNA (change in the anomeric configuration from β to α), alt-DNA, and 1-DNA.

Examples of modified carbohydrates include, but are not limited to, backbones with C 1'-bases connectivities such as tetrofuranosyl oligonucleotides, pentopyranosyl oligonucleotides, and hexopyranosyl oligonucleotides; backbones with CT-base connectivities such as isonucleotides (repositioning of the base sugar connection from C 1 to the C2 position), HNAs (insertion of an additional methylene group between the 04' and C 1' position of a furanose), ANAs (incorporation of a C3'-(S)-hydroxyl group), MNAs (inversion of the C3'-OH configuration from (S) in ANAs to (R)), CNAs (replacement of the 0 of the hexose with a methylene group), CeNAs (introduction of a 5'-6' alkene within the analogous ring), as well as other ring systems, torsionally restricted oligonucleotides such as bicyclic oligonucleotides, LNAs (restriction of the pentofaranose backbone to the 3'-endo configuration), torsionally flexible oligonucleotides such as base sugar extensions (insertion of methylene and ethylene groups into both α- and β-deoxynucleotides) and acyclic backbones (glycerol derivatives incorporating phosphodiester linkages).

Examples of nucleotides with modified nucleotide linkages include, but are not limited to, PNAs (peptide nucleic acids), NDPs (nucleo-δ-peptides), fused sugar-base backbones, and cationic linkages.

Examples of alternative nucleobases include, but are not limited to, nucleotides with alternative aromatic nucleobases.

Other Materials

Other materials which can self assemble include N-alkylacrylamide oligomers and di- and triblock co-polymers. N-alkylacrylamides can assume self-assembled into sheet-like structures (see Kendhale et al., Chem Comm.,). Examples of block copolymers include copolypeptides, polypeptide-PEGS, PEO-polybutadienes, PEG-polysaccharides, etc.

Another class of materials which are known to self-assemble are dendrimers. "Dendrimers", as used herein, refers to branched polymers with successive shells of branch units surrounding central core. Dendrimers can self-assemble through a variety of different mechanisms, such as hydrogen bonding, ionic interactions, hydrophobic interactions, solvent interaction, side chain interactions, and the like. Non-limiting examples of self-assembling dendrimers are described in Zimmerman et al., Science, Vol. 271, No. 5252, 1095-1098 (1996); Zimmerman et al., J. Am. Chem. Soc., 124(46), 13757-13769 (2002); and Frechet, Proc. Nat. Acad. Sci., Vol. 99, No. 8, 4782-4787 (2002).

B. Formation of Self-Assembling Materials

Prior to self-assembly, the materials may be contained in (e.g., dissolved in) a solution that is substantially free of ions (e.g., monovalent ions) or that contains a sufficiently low concentration of ions to prevent significant self-assembly (e.g., a concentration of ions less than 10, 5, 1, or 0.1 mM). Self-assembly may be initiated or enhanced at any subsequent time by the addition of an ionic solute or diluent to a solution of the material or by a change in pH. For example, NaCl at a concentration of between approximately 5 mM and 5 M can induce the assembly of macroscopic structures within a short period of time (e.g., within a few minutes). Lower concentrations of NaCl may also induce assembly but at a slower rate. Alternatively, self-assembly may be initiated or enhanced by introducing the materials (whether dry, in a semi-solid gel, or dissolved in a liquid solution that is substantially free of ions) into a fluid (e.g., a physiological fluid such as blood or gastric juice) or an area (e.g., a body cavity such as the nose or mouth or a cavity exposed by a surgical procedure) comprising such ions. The gel does not have to be preformed prior to application to the desired site. Generally, self-assembly is expected to occur upon contacting the materials with such a solution in any manner.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$. The concentration of such ions required to induce or enhance self-assembly is typically at least 5 mM (e.g., at least 10, 20, or 50 mM). Lower concentrations also facilitate assembly, although at a reduced rate. When desired, self-assembling materials can be delivered with a hydrophobic material (e.g. a pharmaceutically acceptable oil) in a concentration that permits self-assembly, but at a reduced rate. When self-assembling materials are mixed with a hydrophobic agent such as an oil or lipid the assembly of the material forms different structures. The structures will appear like ice on a layer of oil. In some cases when another material is added, the material will assemble into various other three dimensional structures that may be suitable for loading of a therapeutic agent. The hydrophilic part of the molecule will assemble in such a way as to minimize hydrophobic-hydrophilic interaction, thereby creating a barrier between the two environments. Several experiments have shown that the self-assembling materials will align on the surface of the oil like ice on water with the hydrophobic part of the molecule toward the surface and the hydrophilic portion of the molecule facing away from the oil, or will form toroidal like structures with the hydrophobic material contained inside. This type of behavior enables the encapsulation of therapeutics or other molecule of interested for delivery in the body.

Alternatively, some of the materials described herein do not require ions to self-assemble but may self assemble due to interactions with a solvent, hydrophobic interactions, side chain interactions, hydrogen bonding, and the like.

Depending on the formulation and desired properties of the macroscopic structure (e.g., the stiffness of the scaffold or the rate of its formation), the concentration of precursors (e.g., self-assembling materials) can vary from approximately 0.01% w/v (0.1 mg/ml) to approximately 99.99% w/v (999.9 mg/ml), inclusive. For example, the concentration prior to scaffold formation can be between approximately 0.1% (1 mg/ml) and 10% (100 mg/ml), inclusive (e.g., about 0.1%-5%; 0.5%-5%; 1.0%; 1.5%; 2.0%; 2.5%; 3.0%; or 4.0% or more). The precursors (e.g., self-assembling materials) can be formulated as powders and administered in a powder form or resuspended. If dry, the materials can then self-assemble following contact with bodily fluids (e.g., at a site of injury).

The materials can be formed within regularly or irregularly-shaped molds, which may include a body cavity or a portion of the body (e.g., the lumen of a blood vessel) or which may be an inert material such as plastic or glass. The structures or scaffolds can be made to conform to a predetermined shape or to have a predetermined volume. To form a structure with a predetermined shape or volume (e.g., a desired geometry or dimension, including thin sheets or films), an aqueous solution of the material is placed in a pre-shaped casting mold, and the materials are induced to self-assemble by the addition of a plurality of ions. Alternately, the ions may be added to the solution shortly before placing the solution into the mold, provided that care is taken to place the solution into the mold before substantial assembly occurs. Where the mold is a tissue (e.g., the lumen of a blood vessel or other compartment, whether in situ or not), the addition of an ionic solution may not be necessary. The resulting material characteristics, the time required for assembly, and the dimensions of the macroscopic structure that forms are governed by the concentration and amount of solution that is applied, the concentration of ions used to induce assembly of the structure, and the dimensions of the casting apparatus. The scaffold can achieve a gel-like or substantially solid form at room temperature, and heat may be applied to facilitate the molding (e.g., one can heat a solution used in the molding process (e.g., a precursor-containing solution) to a temperature ranging up to about body temperature (approximately 378C)). Once the scaffold has reached the desired degree of firmness, it can be removed from the mold and used for a purpose described herein. Alternatively, the materials described herein may be used to anchor host tissue to a tissue matrix or scaffold. For example, the materials described herein can be used as a "glue" to anchor host tissue that is to be regenerated to a tissue matrix or scaffold to ensure that the matrix or scaffold stays in place in the local environment to which it is injected or implanted. Tissue matrices and scaffolds are well known in the art and can be prepared from synthetic, semi-synthetic, and/or natural materials.

Materials that assemble and/or undergo a phase transition (e.g., a transition from a liquid state to a semi-solid, gel, etc.) when they come in contact with the body are useful in preventing the movement of bodily substances. Self-assembly or phase transition is triggered by components found in a subject's body (e.g., ions) or by physiological pH and is assisted by physiological temperatures. Self-assembly or phase transition can begin when the compositions are exposed to or brought into contact with a subject's body and may be facilitated by the local application of heat to the area where the composition has been (or will be) deposited. Based on studies to date, self-assembly occurs rapidly upon contact with internal bodily tissues without the application of additional heat. The time required for effective assembly and/or phase transition can occur in 60 seconds or less following contact with a subject's internal tissues or to conditions similar to those found within the body (e.g., in 50, 40, 30, 20, or 10 seconds or less). In some circumstances, such as where the concentration of self-assembling agents in the composition is low or where the movement of the bodily substance is substantial, self-assembly or phase transition may take longer to achieve the desired effect, for example, up to a minute, 5 minutes, 10 minutes, 30 minutes, an hour, or longer. For example, a solution containing a self-assembling peptide applied to sites of blood vessel transection in the brain, liver, or muscle provided complete hemostasis within times as short as 10 seconds following application. Ion-containing solutions may be preferred when the compositions are used to protect a subject from contamination, as phase transitions do not occur, or do not readily occur, when non-ionic compositions contact intact skin.

The compositions can form structures that are substantially rigid (e.g., solid or nearly solid) or that assume a definite shape and volume (e.g., structures that conform to the shape and volume of the location to which a liquid composition was administered, whether in vivo or ex vivo). The solidified material may be somewhat deformable or compressible after assembly or phase transition, but will not substantially flow from one area to another, as compositions at a different point along the liquid to solid continuum may do, which may be due, at least in part, to their ability to undergo phase transitions. As a result, the compositions can be used to prevent the movement of a bodily substance in a subject in need thereof. Self-assembly can also be achieved ex vivo by exposure to conditions within a certain range of physiological values (e.g., conditions appropriate for cell or tissue culture). While liquid formulations are readily dispensed, the compositions administered may also be in a gel form that may become stiffer upon contact with the subject's body.

The concentration of the self-assembling materials in any given formulation can vary and can be between approximately 0.1% (1 mg/ml) and 10% (100 mg/ml), inclusive. For example, the concentration of the self-assembling peptides (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling materials can be higher in stock solutions and in solid (e.g., powdered) formulations. In solid preparations, the concentration of self-assembling materials can approach 100% (e.g., the concentration of self-assembling peptides can be 95, 96, 97, 98, 99% or more (e.g., 99.99%) of the composition). Whether in liquid or solid form, the materials can be brought to the desired concentration prior to use by addition of a diluent (e.g., deionized water), powder, wetting agent, or a therapeutic, diagnostic or prophylactic agent.

Regardless of the precise nature of the self-assembling materials, upon exposure to conditions such as those described herein, the materials can form membranous two- or three-dimensional structures including a stable macroscopic porous matrix having ordered interwoven nanofibers (e.g., fibers approximately 10-20 nm in diameter, with a pore size of about 50-100 nm in a linear dimension). Three-dimensional macroscopic matrices can have dimensions large enough to be visible under low magnification (e.g., about 10-fold or less), and the membranous structures can be visible to the naked eye, even if transparent. Although three-dimensional, the structures can be exceedingly thin, including a limited number of layers of molecules (e.g., 2, 3, or more layers of molecules). Typically, each dimension of a given structure will be at least 10 µm in size (e.g., two dimensions of at least 100-1000 µm in size (e.g., 1-10 mm, 10-100 mm, or more)). The relevant dimensions may be expressed as length, width, depth, breadth, height, radius, diameter, or circumference in the case of structures that have a substantially regular shape (e.g., where the structure is a sphere, cylinder, cube, or the like) or an approximation of any of the foregoing where the structures do not have a regular shape.

The self-assembling materials can form a hydrated material when contacted with water under conditions such as those described herein (e.g., in the presence of a sufficient concentration (e.g., physiological concentrations) of ions (e.g., monovalent cations)). The materials may have a high water content (e.g., approximately 95% or more (e.g., approximately 97%, 98%, 99% or more)), and the compositions can be hydrated but not substantially self-assembled. A given value may be "approximate" in recognition of the fact that measurements can vary depending, for example, on the circumstances under which they are made and the skill of the person taking the measurement. Generally, a first value is approximately equal to a second when the first falls within 10% of the second (whether greater than or less than) unless it is otherwise clear from the context that a value is not approximate or where, for example, such value would exceed 100% of a possible value.

The properties and mechanical strength of the structures or scaffolds can be controlled as required through manipulation of the components therein. For example, the stiffness of an assembled gel can be increased by increasing the concentration of self-assembling materials therein. The sequences, characteristics, and properties of the materials and the structures formed by them upon self-assembly are discussed further below.

The compositions can be formulated as concentrated stocks or in dry form, and these can be diluted or dissolved to form biocompatible compositions, which are substantially non-toxic to biological cells in vitro or in vivo. For example, the compositions can contain materials in quantities that do not elicit a significant deleterious effect on the recipient's body (e.g., a prohibitively severe immunological or inflammatory reaction, or unacceptable scar tissue formation).

When a solution containing non-assembled materials is laid down on a biological tissue, the materials having sufficient proximity to the tissue assemble, causing the solution to gel. Any solution that remains distant from the tissue remains liquid, as the self-assembling materials have not yet been exposed to conditions that promote their assembly. As the material is disturbed (e.g., by performing a surgical procedure), liquid material appears to gel as it comes into sufficient contact with the body. At times, the compositions can take on characteristics ranging from a liquid to those of a solid, appearing gel- or salve-like or as a slurry).

The self assembling material may further contain a tissue specific component. The tissue specific component can be peptides, polysaccharides, or glycoproteins that are specific for eye, brain, or skin cells. For example, cell surface carbohydrates are major components of the outer surface of mammalian cells and are very often characteristic of cell types. It is assumed that cell type-specific carbohydrates are involved in cell-cell interaction. The tissue specific component can therefore, target these cell specific surface carbohydrates.

```
1 G G G G G D G D G D G D G D (SEQ ID NO: 58)

2 G G G G G E G E G E G E G E (SEQ ID NO: 59)

3 G G G G G K G K G K G K G K (SEQ ID NO: 60)

4 G G G G G R G R G R G R G R (SEQ ID NO: 61)
```

-continued

| 5 | G G G G G H G H G H G H G H | (SEQ ID NO: 62) |
| 6 | A A A A A D A D A D A D A D | (SEQ ID NO: 63) |
| 7 | A A A A A E A E A E A E A E | (SEQ ID NO: 64) |
| 8 | A A A A A K A K A K A K A K | (SEQ ID NO: 65) |
| 9 | A A A A A R A R A R A R A R | (SEQ ID NO: 66) |
| 10 | A A A A A H A H A H A H A H | (SEQ ID NO: 67) |
| 11 | V V V V V D V D V D V D V D | (SEQ ID NO: 68) |
| 12 | V V V V V E V E V E V E V E | (SEQ ID NO: 69) |
| 13 | V V V V V K V K V K V K V K | (SEQ ID NO: 70) |
| 14 | V V V V V R V R V R V R V R | (SEQ ID NO: 71) |
| 15 | V V V V V H V H V H V H V H | (SEQ ID NO: 72) |
| 16 | L L L L L D L D L D L D L D | (SEQ ID NO: 73) |
| 17 | L L L L L E L E L E L E L E | (SEQ ID NO: 74) |
| 18 | L L L L L K L K L K L K L K | (SEQ ID NO: 75) |
| 19 | L L L L L R L R L R L R L R | (SEQ ID NO: 76) |
| 20 | L L L L L H L H L H L H L H | (SEQ ID NO: 77) |
| 21 | I I I I I D I D I D I D I D | (SEQ ID NO: 78) |
| 22 | I I I I I E I E I E I E I E | (SEQ ID NO: 79) |
| 23 | I I I I I K I K I K I K I K | (SEQ ID NO: 80) |
| 24 | I I I I I R I R I R I R I R | (SEQ ID NO: 81) |
| 25 | I I I I I H I H I H I H I H | (SEQ ID NO: 82) |
| 26 | M M M M M D M D M D M D M D | (SEQ ID NO: 83) |
| 27 | M M M M M E M E M E M E M E | (SEQ ID NO: 84) |
| 28 | M M M M M K M K M K M K M K | (SEQ ID NO: 85) |
| 29 | M M M M M R M R M R M R M R | (SEQ ID NO: 86) |
| 30 | M M M M M H M H M H M H M H | (SEQ ID NO: 87) |
| 31 | F F F F F D F D F D F D F D | (SEQ ID NO: 88) |
| 32 | F F F F F E F E F E F E F E | (SEQ ID NO: 89) |
| 33 | F F F F F K F K F K F K F K | (SEQ ID NO: 90) |
| 34 | F F F F F R F R F R F R F R | (SEQ ID NO: 91) |
| 35 | F F F F F H F H F H F H F H | (SEQ ID NO: 92) |
| 36 | W W W W W D W D W D W D W D | (SEQ ID NO: 93) |
| 37 | W W W W W E W E W E W E W E | (SEQ ID NO: 94) |
| 38 | W W W W W K W K W K W K W K | (SEQ ID NO: 95) |
| 39 | W W W W W R W R W R W R W R | (SEQ ID NO: 96) |
| 40 | W W W W W H W H W H W H W H | (SEQ ID NO: 97) |
| 41 | P P P P P D P D P D tD D P D P D | (SEQ ID NO: 98) |
| 42 | P P P P P E P E P E P E P E | (SEQ ID NO: 99) |
| 43 | P P P P P K P K P K P K P K | (SEQ ID NO: 100) |
| 44 | P P P P P R P R P R P R P R | (SEQ ID NO: 101) |
| 45 | P P P P P H P H P H P H P H | (SEQ ID NO: 102) |
| 46 | A A A A R A D A R A D A R A D | (SEQ ID NO: 103) |
| 47 | A A A A R A R A D A D A R A R | (SEQ ID NO: 104) |
| 48 | A A A A E A K A E A K A E A K | (SEQ ID NO: 105) |
| 49 | A A A A E A E A K A K A E A E | (SEQ ID NO: 106) |
| 50 | A A A A R A E A R A E A R A E | (SEQ ID NO: 107) |
| 51 | A A A A R A R A E A E A R A E | (SEQ ID NO: 108) |
| 52 | A A A A K A D A K A D A K A D | (SEQ ID NO: 109) |
| 53 | A A A A E A H A E A H A E A H | (SEQ ID NO: 110) |
| 54 | A A A A E A E A H A H A E A E | (SEQ ID NO: 111) |
| 55 | A A A A R A R A R A R A R A R | (SEQ ID NO: 112) |
| 56 | A A A A R A R A R A R A D A D | (SEQ ID NO: 113) |
| 57 | A A A A R A R A R A D A D A D | (SEQ ID NO: 114) |
| 58 | A A A A H A D A H A D A H A D | (SEQ ID NO: 115) |
| 59 | A A A A H A H A H A H A H A H | (SEQ ID NO: 116) |
| 60 | A A A A H A D A D A H A D A D | (SEQ ID NO: 117) |
| 61 | A A A A H A E A E A H A E A E | (SEQ ID NO: 118) |
| 62 | G G G G G R G D G R G D G R G D | (SEQ ID NO: 119) |
| 63 | G G G G G R G R G D G D G R G R | (SEQ ID NO: 120) |
| 64 | G G G G G E G K G E G K G E G K | (SEQ ID NO: 121) |
| 65 | G G G G G E G E G K G K G E G E | (SEQ ID NO: 122) |
| 66 | G G G G G R G E G R G E G R G E | (SEQ ID NO: 123) |
| 67 | G G G G G R G R G E G E G R G E | (SEQ ID NO: 124) |
| 68 | G G G G G K G D G K G D G K G D | (SEQ ID NO: 125) |
| 69 | G G G G G E G H G E G H G E G H | (SEQ ID NO: 126) |
| 70 | G G G G G E G E G H G H G E G E | (SEQ ID NO: 127) |
| 71 | G G G G G R G R G R G R G R G R | (SEQ ID NO: 128) |
| 72 | G G G G G R G R G R G D G D | (SEQ ID NO: 129) |
| 73 | G G G G G R G R G R G D G D G D | (SEQ ID NO: 130) |
| 74 | G G G G H G D G H G D G H G D | (SEQ ID NO: 131) |
| 75 | G G G G H G H G H G H G H G H | (SEQ ID NO: 132) |
| 76 | G G G G H G D G D G H G D G D | (SEQ ID NO: 133) |
| 77 | G G G G H G E G E G H G E G E | (SEQ ID NO: 134) |
| 78 | V V V V R V D V R V D V R V D | (SEQ ID NO: 135) |
| 79 | V V V V R V R V D V D V R V R | (SEQ ID NO: 136) |
| 80 | V V V V E V K V E V K V E V K | (SEQ ID NO: 137) |
| 81 | V V V V E V E V K V K V E V E | (SEQ ID NO: 138) |
| 82 | V V V V R V E V R V E V R V E | (SEQ ID NO: 139) |
| 83 | V V V V R V R V E V E V R V E | (SEQ ID NO: 140) |
| 84 | V V V V K V D V K V D V K V D | (SEQ ID NO: 141) |

-continued

```
 85 V V V V E V H V E V H V E V H (SEQ ID NO: 142)
 86 V V V V E V E V H V H V E V E (SEQ ID NO: 143)
 87 V V V V R V R V R V R V R V R (SEQ ID NO: 144)
 88 V V V V R V R V R V R V D V D (SEQ ID NO: 145)
 89 V V V V R V R V R V D V D V D (SEQ ID NO: 146)
 90 V V V V H V D V H V D V H V D (SEQ ID NO: 147)
 91 V V V V H V H V H V H V H V H (SEQ ID NO: 148)
 92 V V V V H V D V D V H V D V D (SEQ ID NO: 149)
 93 V V V V H V E V E V H V E V E (SEQ ID NO: 150)
 94 L L L L R L D L R L D L R L D (SEQ ID NO: 151)
 95 L L L L R L R L D L D L R L R (SEQ ID NO: 152)
 96 L L L L E L K L E L K L E L K (SEQ ID NO: 153)
 97 L L L L E L E L K L K L E L E (SEQ ID NO: 154)
 98 L L L L R L E L R L E L R L E (SEQ ID NO: 155)
 99 L L L L R L R L E L E L R L E (SEQ ID NO: 156)
100 L L L L K L D L K L D L K L D (SEQ ID NO: 157)
101 L L L L E L H L E L H L E L H (SEQ ID NO: 158)
102 L L L L E L E L H L H L E L E (SEQ ID NO: 159)
103 L L L L R L R L R L R L R L R (SEQ ID NO: 160)
104 L L L L R L R L R L R L D L D (SEQ ID NO: 161)
105 L L L L R L R L R L D L D L D (SEQ ID NO: 162)
106 L L L L H L D L H L D L H L D (SEQ ID NO: 163)
107 L L L L H L H L H L H L H L H (SEQ ID NO: 164)
108 L L L L H L D L D L H L D L D (SEQ ID NO: 165)
109 L L L L H L E L E L H L E L E (SEQ ID NO: 166)
110 I I I I R I D I R I D I R I D (SEQ ID NO: 167)
111 I I I I R I R I D I D I R I R (SEQ ID NO: 168)
112 I I I I E I K I E I K I E I K (SEQ ID NO: 169)
113 I I I I E I E I K I K I E I E (SEQ ID NO: 170)
114 I I I I R I E I R I E I R I E (SEQ ID NO: 171)
115 I I I I R I R I E I E I R I E (SEQ ID NO: 172)
116 I I I I K I D I K I D I K I D (SEQ ID NO: 173)
117 I I I I E I H I E I H I E I H (SEQ ID NO: 174)
118 I I I I E I E I H I H I E I E (SEQ ID NO: 175)
119 I I I I R I R I R I R I R I R (SEQ ID NO: 176)
120 I I I I R I R I R I R I D I D (SEQ ID NO: 177)
121 I I I I R I R I R I D I D I D (SEQ ID NO: 178)
122 I I I I H I D I H I D I H I D (SEQ ID NO: 179)
123 I I I I H I H I H I H I H I H (SEQ ID NO: 180)
124 I I I I H I D I D I H I D I D (SEQ ID NO: 181)
125 I I I I H I E I E I H I E I E (SEQ ID NO: 182)
126 M M M M R M D M R M D M R M D (SEQ ID NO: 183)
127 M M M M R M R M D M D M R M R (SEQ ID NO: 184)
128 M M M M E M K M E M K M E M K (SEQ ID NO: 185)
129 M M M M E M E M K M K M E M E (SEQ ID NO: 186)
130 M M M M R M E M R M E M R M E (SEQ ID NO: 187)
131 M M M M R M R M E M E M R M E (SEQ ID NO: 188)
132 M M M M K M D M K M D M K M D (SEQ ID NO: 189)
133 M M M M E M H M E M H M E M H (SEQ ID NO: 190)
134 M M M M E M E M H M H M E M E (SEQ ID NO: 191)
135 M M M M R M R M R M R M R M R (SEQ ID NO: 192)
136 M M M M R M R M R M R M D M D (SEQ ID NO: 193)
137 M M M M R M R M R M D M D M D (SEQ ID NO: 194)
138 M M M M H M D M H M D M H M D (SEQ ID NO: 195)
139 M M M M H M H M H M H M H M H (SEQ ID NO: 196)
140 M M M M H M D M D M H M D M D (SEQ ID NO: 197)
141 M M M M H M E M E M H M E M E (SEQ ID NO: 198)
142 F F F F R F D F R F D F R F D (SEQ ID NO: 199)
143 F F F F R F R F D F D F R F R (SEQ ID NO: 200)
144 F F F F E F K F E F K F E F K (SEQ ID NO: 201)
145 F F F F E F E F K F K F E F E (SEQ ID NO: 202)
146 F F F F R F E F R F E F R F E (SEQ ID NO: 203)
147 F F F F R F R F E F E F R F E (SEQ ID NO: 204)
148 F F F F K F D F K F D F K F D (SEQ ID NO: 205)
149 F F F F E F H F E F H F E F H (SEQ ID NO: 206)
150 F F F F E F E F H F H F E F E (SEQ ID NO: 207)
151 F F F F R F R F R F R F R F R (SEQ ID NO: 208)
152 F F F F R F R F R F R F D F D (SEQ ID NO: 209)
153 F F F F R F R F R F D F D F D (SEQ ID NO: 210)
154 F F F F H F D F H F D F H F D (SEQ ID NO: 211)
155 F F F F H F H F H F H F H F H (SEQ ID NO: 212)
156 F F F F H F D F D F H F D F D (SEQ ID NO: 213)
157 F F F F H F E F E F H F E F E (SEQ ID NO: 214)
158 W W W W R W D W R W D W R W D (SEQ ID NO: 215)
159 W W W W R W R W D W D W R W R (SEQ ID NO: 216)
160 W W W W E W K W E W K W E W K (SEQ ID NO: 217)
161 W W W W E W E W K W K W E W E (SEQ ID NO: 218)
162 W W W W R W E W R W E W R W E (SEQ ID NO: 219)
163 W W W W R W R W E W E W R W E (SEQ ID NO: 220)
164 W W W W K W D W K W D W K W D (SEQ ID NO: 221)
165 W W W W E W H W E W H W E W H (SEQ ID NO: 222)
```

```
166 W W W W E W E W H W H W E W E (SEQ ID NO: 223)
167 W W W W R W R W R W R W R (SEQ ID NO: 224)
168 W W W W R W R W R W D W D (SEQ ID NO: 225)
169 W W W W R W R W D W D W D (SEQ ID NO: 226)
170 W W W W H W D W H W D W H W D (SEQ ID NO: 227)
171 W W W W H W H W H W H W H (SEQ ID NO: 228)
172 W W W W H W D W D W H W D W D (SEQ ID NO: 229)
173 W W W W H W E W E W H W E W E (SEQ ID NO: 230)
174 P P P P R P D P R P D P R P D (SEQ ID NO: 231)
175 P P P P R P R P D P D P R P R (SEQ ID NO: 232)
176 P P P P E P K P E P K P E P K (SEQ ID NO: 233)
177 P P P P E P E P K P K P E P E (SEQ ID NO: 234)
178 P P P P R P E P R P E P R P E (SEQ ID NO: 235)
179 P P P P R P R P E P E P R P E (SEQ ID NO: 236)
180 P P P P K P D P K P D P K P D (SEQ ID NO: 237)
181 P P P P E P H P E P H P E P H (SEQ ID NO: 238)
182 P P P P E P E P H P H P E P E (SEQ ID NO: 239)
183 P P P P R P R P R P R P R P R (SEQ ID NO: 240)
184 P P P P R P R P R P R P D P D (SEQ ID NO: 241)
185 P P P P R P R P R P D P D P D (SEQ ID NO: 242)
186 P P P P H P D P H P D P H P D (SEQ ID NO: 243)
187 P P P P H P H P H P H P H P H (SEQ ID NO: 244)
188 P P P P H P D P D P H P D P D (SEQ ID NO: 245)
189 P P P P H P E P E P H P E P E (SEQ ID NO: 246)
190 S S S S R S D S R S D S R S D (SEQ ID NO: 247)
191 S S S S R S R S D S D S R S R (SEQ ID NO: 248)
192 S S S S E S K S E S K S E S K (SEQ ID NO: 249)
193 S S S S E S E S K S K S E S E (SEQ ID NO: 250)
194 S S S S R S E S R S E S R S E (SEQ ID NO: 251)
195 S S S S R S R S E S E S R S E (SEQ ID NO: 252)
196 S S S S K S D S K S D S K S D (SEQ ID NO: 253)
197 S S S S E S H S E S H S E S H (SEQ ID NO: 254)
198 S S S S E S E S H S H S E S E (SEQ ID NO: 255)
199 S S S S R S R S R S R S R S R (SEQ ID NO: 256)
200 S S S S R S R S R S R S D S D (SEQ ID NO: 257)
201 S S S S R S R S R S D S D S D (SEQ ID NO: 258)
202 S S S S H S D S H S D S H S D (SEQ ID NO: 259)
203 S S S S H S H S H S H S H S H (SEQ ID NO: 260)
204 S S S S H S D S D S H S D S D (SEQ ID NO: 261)
205 S S S S H S E S E S H S E S E (SEQ ID NO: 262)
206 T T T T R T D T R T D T R T D (SEQ ID NO: 263)
207 T T T T R T R T D T D T R T R (SEQ ID NO: 264)
208 T T T T E T K T E T K T E T K (SEQ ID NO: 265)
209 T T T T E T E T K T K T E T E (SEQ ID NO: 266)
210 T T T T R T E T R T E T R T E (SEQ ID NO: 267)
211 T T T T R T R T E T E T R T E (SEQ ID NO: 268)
212 T T T T K T D T K T D T K T D (SEQ ID NO: 269)
213 T T T T E T H T E T H T E T H (SEQ ID NO: 270)
214 T T T T E T E T H T H T E T E (SEQ ID NO: 271)
215 T T T T R T R T R T R T R T R (SEQ ID NO: 272)
216 T T T T R T R T R T R T D T D (SEQ ID NO: 273)
217 T T T T R T R T R T D T D T D (SEQ ID NO: 274)
218 T T T T H T D T H T D T H T D (SEQ ID NO: 275)
219 T T T T H T H T H T H T H T H (SEQ ID NO: 276)
220 T T T T H T D T D T H T D T D (SEQ ID NO: 277)
                                    (SEQ ID NO: 2789)
221 T T T T H T E T E T H T E T E
222 C C C C R C D C R C D C R C D (SEQ ID NO: 279)
223 C C C C R C R C D C D C R C R (SEQ ID NO: 280)
224 C C C C E C K C E C K C E C K (SEQ ID NO: 281)
225 C C C C E C E C K C K C E C E (SEQ ID NO: 282)
226 C C C C R C E C R C E C R C E (SEQ ID NO: 283)
227 C C C C R C R C E C E C R C E (SEQ ID NO: 284)
228 C C C C K C D C K C D C K C D (SEQ ID NO: 285)
229 C C C C E C H C E C H C E C H (SEQ ID NO: 286)
230 C C C C E C E C H C H C E C E (SEQ ID NO: 287)
231 C C C C R C R C R C R C R C R (SEQ ID NO: 288)
232 C C C C R C R C R C R C D C D (SEQ ID NO: 289)
233 C C C C R C R C R C D C D C D (SEQ ID NO: 290)
234 C C C C H C D C H C D C H C D (SEQ ID NO: 291)
235 C C C C H C H C H C H C H C H (SEQ ID NO: 292)
236 C C C C H C D C D C H C D C D (SEQ ID NO: 293)
237 C C C C H C E C E C H C E C E (SEQ ID NO: 294)
238 Y Y Y Y R Y D Y R Y D Y R Y D (SEQ ID NO: 295)
239 Y Y Y Y R Y R Y D Y D Y R Y R (SEQ ID NO: 296)
240 Y Y Y Y E Y K Y E Y K Y E Y K (SEQ ID NO: 297)
241 Y Y Y Y E Y E Y K Y K Y E Y E (SEQ ID NO: 298)
242 Y Y Y Y R Y E Y R Y E Y R Y E (SEQ ID NO: 299)
243 Y Y Y Y R Y R Y E Y E Y R Y E (SEQ ID NO: 300)
244 Y Y Y Y K Y D Y K Y D Y K Y D (SEQ ID NO: 301)
245 Y Y Y Y E Y H Y E Y H Y E Y H (SEQ ID NO: 302)
246 Y Y Y Y E Y E Y H Y H Y E Y E (SEQ ID NO: 303)
```

-continued

| | | | | | | | | | | | | | | | |
|---|---|---|---|---|---|---|---|---|---|---|---|---|---|---|---|
|247|Y|Y|Y|Y|Y|R|Y|R|Y|R|Y|R|Y|R|(SEQ ID NO: 304)|
|248|Y|Y|Y|Y|Y|R|Y|R|Y|R|Y|R|Y|D|(SEQ ID NO: 305)|
|249|Y|Y|Y|Y|Y|R|Y|R|Y|D|Y|D|Y|D|(SEQ ID NO: 306)|
|250|Y|Y|Y|Y|H|Y|D|Y|H|Y|D|Y|H|Y|D|(SEQ ID NO: 307)|
|251|Y|Y|Y|Y|H|Y|H|Y|H|Y|H|Y|H|Y|H|(SEQ ID NO: 308)|
|252|Y|Y|Y|Y|H|Y|D|Y|D|Y|H|Y|D|Y|D|(SEQ ID NO: 309)|
|253|Y|Y|Y|Y|H|Y|E|Y|E|Y|H|Y|E|Y|E|(SEQ ID NO: 310)|
|254|N|N|N|N|R|N|D|N|R|N|D|N|R|N|D|(SEQ ID NO: 311)|
|255|N|N|N|N|R|N|R|N|D|N|D|N|R|N|R|(SEQ ID NO: 312)|
|256|N|N|N|N|E|N|K|N|E|N|K|N|E|N|K|(SEQ ID NO: 313)|
|257|N|N|N|N|E|N|E|N|K|N|K|N|E|N|E|(SEQ ID NO: 314)|
|258|N|N|N|N|R|N|E|N|R|N|E|N|R|N|E|(SEQ ID NO: 315)|
|259|N|N|N|N|R|N|R|N|E|N|E|N|R|N|E|(SEQ ID NO: 316)|
|260|N|N|N|N|K|N|D|N|K|N|D|N|K|N|D|(SEQ ID NO: 317)|
|261|N|N|N|N|E|N|H|N|E|N|H|N|E|N|H|(SEQ ID NO: 318)|
|262|N|N|N|N|E|N|E|N|H|N|H|N|E|N|E|(SEQ ID NO: 319)|
|263|N|N|N|N|R|N|R|N|R|N|R|N|R|N|R|(SEQ ID NO: 320)|
|264|N|N|N|N|R|N|R|N|R|N|R|N|D|N|D|(SEQ ID NO: 321)|
|265|N|N|N|N|R|N|R|N|R|N|D|N|D|N|D|(SEQ ID NO: 322)|
|266|N|N|N|N|H|N|D|N|H|N|D|N|H|N|D|(SEQ ID NO: 323)|
|267|N|N|N|N|H|N|H|N|H|N|H|N|H|N|H|(SEQ ID NO: 324)|
|268|N|N|N|N|H|N|D|N|D|N|H|N|D|N|D|(SEQ ID NO: 325)|
|269|N|N|N|N|H|N|E|N|E|N|H|N|E|N|E|(SEQ ID NO: 326)|
|270|Q|Q|Q|Q|R|Q|D|Q|R|Q|D|Q|R|Q|D|(SEQ ID NO: 327)|
|271|Q|Q|Q|Q|R|Q|R|Q|D|Q|D|Q|R|Q|R|(SEQ ID NO: 328)|
|272|Q|Q|Q|Q|E|Q|K|Q|E|Q|K|Q|E|Q|K|(SEQ ID NO: 329)|
|273|Q|Q|Q|Q|E|Q|E|Q|K|Q|K|Q|E|Q|E|(SEQ ID NO: 330)|
|274|Q|Q|Q|Q|R|Q|E|Q|R|Q|E|Q|R|Q|E|(SEQ ID NO: 331)|
|275|Q|Q|Q|Q|R|Q|R|Q|E|Q|E|Q|R|Q|E|(SEQ ID NO: 332)|
|276|Q|Q|Q|Q|K|Q|D|Q|K|Q|D|Q|K|Q|D|(SEQ ID NO: 333)|
|277|Q|Q|Q|Q|E|Q|H|Q|E|Q|H|Q|E|Q|H|(SEQ ID NO: 334)|
|278|Q|Q|Q|Q|E|Q|E|Q|H|Q|H|Q|E|Q|E|(SEQ ID NO: 335)|
|279|Q|Q|Q|Q|R|Q|R|Q|R|Q|R|Q|R|Q|R|(SEQ ID NO: 336)|
|280|Q|Q|Q|Q|R|Q|R|Q|R|Q|R|Q|D|Q|D|(SEQ ID NO: 337)|
|281|Q|Q|Q|Q|R|Q|R|Q|R|Q|D|Q|D|Q|D|(SEQ ID NO: 338)|
|282|Q|Q|Q|Q|H|Q|D|Q|H|Q|D|Q|H|Q|D|(SEQ ID NO: 339)|
|283|Q|Q|Q|Q|H|Q|H|Q|H|Q|H|Q|H|Q|H|(SEQ ID NO: 340)|
|284|Q|Q|Q|Q|H|Q|D|Q|D|Q|H|Q|D|Q|D|(SEQ ID NO: 341)|
|285|Q|Q|Q|Q|H|Q|E|Q|E|Q|H|Q|E|Q|E|(SEQ ID NO: 342)|

B. Therapeutic, Prophylactic and Diagnostic Agents

The formulations may also include other therapeutic, prophylactic or diagnostic agents. In a preferred embodiment, these may be antiinflammatories, vasoactive agents, anti-infectives, anesthetics, growth factors, vitamind, nutrients, and/or cells.

These can be peptides or proteins, polysaccharides or saccharides, nucleic acids nucleotides, proteoglycan, lipid, carbohydrate, or a small molecule, typically an organic compound, having multiple carbon-carbon bonds that may be isolated from nature or prepared via chemical synthesis. Small molecules have relatively low molecular weights (e.g., less than about 1500 g/mol) and are not peptides or nucleic acids. The substance can also be a biomolecule, which is a molecule such as a peptide, protcoglycan, lipid, carbohydrate, or nucleic acid having characteristics typical of molecules found in living organisms. Like small molecules, biomolecules can be naturally occurring or may be artificial (i.e., they may be molecules that have not been found in nature). For example, a protein having a sequence that has not been found in nature (e.g., one that does not occur in a publicly available database of sequences) or that has a known sequence modified in an unnatural way by a human hand (e.g., a sequence modified by altering a post-translational process such as glycosylation) is an artificial biomolecule. Nucleic acid molecules encoding such proteins (e.g., an oligonucleotide, optionally contained within an expression vector) are also biomolecules and can be incorporated into the compositions described herein. For example, a composition can include a plurality of self-assembling materials and cells that express, or that are engineered to express, a protein biomolecule (by virtue of containing a nucleic acid sequence that encodes the protein biomolecule).

Many different therapeutic, prophylactic or diagnostic agents can be incorporated into the formulation. Representative vasoconstrictors include epinephrine and phenylephrine; representative coloring agents include arsenazo III, chlorophosphonazo III, antipyrylazo 111, murexide, Eriochrome Black T, Eriochrome Blue SE, oxyacetazo I, carboxyazo III, tropolone, methylthymol blue, and Mordant Black 32; representative anesthetic agents include benzocaine, bupivacaine, butamben picrate, chloroprocaine, cocaine, curate, dibucaine, dyclonine, etidocaine, lidocaine, mepivacaine, pramoxine, prilocaine, procaine, propoxycaine, ropivacaine, tetracaine, or combinations thereof. Local application of the anesthetic agent may be all that is required in some situations, for example, for a burn or other wound to the skin, including decubitus ulcers; wounds, such as cancer sores; or for minimally invasive surgeries. Combining local anesthetics with the self-assembling materials, whether combined by virtue of being present in the same formulation or by virtue of co-administration, can help contain the anesthetic within the body and reduce the amount entering the circulation.

Vasoconstrictors such as phenylephrine can be included to prolong the effect of local anesthesia (e.g., 0.1-0.5% phenylephrine). Analgesic agents other than a local anesthetic agent, such as steroids, non-steroidal anti-inflammatory agents like indomethacin, platelet activating factor (PAF) inhibitors such as lexipafant, CV 3988, and/or PAF receptor inhibitors such as SRI 63-441. An anti-infective or antimicrobial agent (e.g., an antibiotic, antibacterial, antiviral, or antifungal agent) can be included for either systemic or local administration. Examples include (β-lactam antibiotics such as penicillins and cephalosporins and other inhibitors of cell wall synthesis such as vancomycin, chloramphenicol, tetracyclines, macrolides, clindamyin, streptogramins, aminoglycosides, spectinomycin, sulfonamides, trimethoprim, quinolones, amphotericin B, flucytosine, azoles such as ketoconazole, itraconazole, fluconazole, clotrimazole, and miconazole, griseofulvin, terbinafine, and nystatin. The antimicrobial can be topically administered (e.g., to treat skin infections or burns, or to help prevent infection at a site of catheter insertion (e.g., an intravenous catheter), for example, kanamycin, neomycin, bacitracin, polymixin, topical sulfonamides such as mafenide acetate or silver sulfadiazine, or gentamicin sulfate. The antimicrobial can also be a broad spectrum agent. For example, a second, third, or fourth generation cephalosporin can be used. These agents may be active against a wide range of bacteria including both gram positive and gram negative species. Such antibacterial agents may be particularly appropriate where the present scaffolds are used to inhibit movement of intestinal contents such as during intestinal resection or other surgery that purposefully or accidentally disturbs the integrity of the intestinal wall. One of ordinary skill in the art will be able to select appropriate antimicrobial agents by considering factors such as the patient's history (e.g., any history of an allergic reaction to such agents), the location to which the peptides are to be applied, the type of infectious agent likely to be present, and so forth.

Any of the compositions described herein, whether they contain only self-assembling precursors or precursors and one or more bioactive molecules (and whether in a liquid, semi-solid, or solid farm), can include a coloring agent. Suitable coloring agents include commercially available food colorings, natural and synthetic dyes, and fluorescent molecules. Preferably, the coloring agent is nontoxic or is included at such low concentrations as to minimize any toxic effect. The use of a coloring agent allows for improved visualization of an area that is covered by a structure or scaffold and can facilitate removal, if such removal is desired. The coloring agent can be one that changes color when it comes into contact with a contaminated area (e.g., a color change may be triggered by the contamination itself (e.g., by the blood or bacteria present at a wound site)). For example, a metabolic product of a bacterium may trigger a color change. Conditions such as pH or redox state induced by contaminants may also be detected. Exemplary indicators include arsenzazo III, chlorophosphonazo III, antipyrylazo III, murexide, Eriochrome Black T and Eriochrome Blue SE for $Mg^{2+}$, oxyacetazo I, carboxyazo III, tropolone, methylthymol blue, and Mordant Black 32. AlamarBlue, a redox indicator, and phenol red are also of use in the compositions and methods.

Many other active agents can be included in the compositions. For example, a number of growth factors can be included to accelerate one or more aspects of healing (e.g., angiogenesis, cell migration, process extension, and cell proliferation). These types of compositions can be "included" as others can, by virtue of inclusion in the compositions or by virtue of co-administration in the present methods. Examples include vascular endothelial growth factor (VEGF), a transforming growth factor (TGF) such as transforming growth factor p, a platelet derived growth factor (PDGF), an epidermal growth factor (EGF), a nerve growth factor (NGF), an insulin-like growth factor (e.g., insulin-like growth factor I), a glial growth factor (GGF), a fibroblast growth factor (FGF), etc. It will be appreciated that in many cases these terms refer to a variety of different molecular species. For example, several transforming growth factor R species are known in the art. One of ordinary skill in the art will be guided in the selection of an appropriate growth factor by considering, for example, the site at which the composition is to be administered. For example, an EGF can be included in compositions applied to the skin; an NGF and/or GGF can be included in compositions applied to nerves or the nervous system; and so forth.

The growth factor or another agent can be a chemotactic substance, which has the ability, in vivo or in cell culture, to recruit cells to a site at which the substance is present. The cells recruited may have the potential to contribute to the formation of new tissue or to repair existing, damaged tissue (e.g., by contributing structurally and/or functionally to the tissue (e.g., by providing growth factors or contributing to a desirable immune response)). Certain chemotactic substances can also function as proliferation agents (e.g., neurotropic factors such as NGF or BDNF).

The compositions can also be used in combination with or instead of compounds such as cyanoacrylates, oxidized cellulose, fibrin sealants, collagen gel, thrombin powder, microporous polysaccharide powders, clotting factors (e.g., Factor V, Factor VIII, fibrinogen, or prothrombin) and zeolite powders.

In one embodiment, vitamins may be added to the material such as vitamin K after liver surgery. In addition, other vitamins can be added to facilitate the reconstruction of tissue or skin when applied topically in combination with the material. This could be after injury or in the normal course of topical hydration.

The one or more therapeutic, diagnostic and/or prophylactic agents can be administered simultaneously with the self-assembling materials in the same formulation, administered simultaneously in separate formulations, or sequentially. Alternatively, the active agent(s) can be covalently coupled to the self-assembling material.

It will be understood that therapeutic molecules are generally administered in an effective amount in order to achieve a clinically significant result, and effective dosages and concentrations are known in the art. These dosages and concentrations can guide the selection of dosages and concentrations in the present context. Bioactive molecules can be provided at a variety of suitable concentrations and in suitable amounts (e.g., in the microgram or milligram range, or greater). For guidance, one can consult texts such as Goodman and Gilman's *The Pharmacological Basis of Therapeutics,* 10th Ed., and Katzung, *Basic and Clinical Pharmacology.*

Cells

Where cells are delivered to a patient (e.g., to promote tissue healing), utologous cells can be used. In one embodiment, the cells could be hematopoietic cells from the patient, dispersed in the material and implanted. In another embodiment, the cells can be cord red blood cells.

Molded scaffolds as described above, liquid compositions, gels, solids (e.g. powders) or other semi-solid embodiments may include one or more additional substances such as bioactive molecules or cells. In some instances, the cell may secrete the bioactive molecule either naturally or following genetic engineering (e.g., to express and/or secrete a recombinant protein). The structures described herein are able to support cell attachment, viability, and growth; these have been observed when cells are cultured on the surface of the material or when cells grow within the material (e.g., when encapsulated). In addition, the structures are able to serve as substrates for neurite growth and synapse formation when neurons are grown on or within them. Thus, bioactive molecules and cells can be encapsulated within the peptide structures and maintain substantial function and viability when so encapsulated (see, e.g., U.S. Ser. Nos. 09/778,200 and 10/196,942).

C. Formulations

In the preferred embodiment, the formulation is a liquid or reconstitutable powder, applied topically. In one embodiment, the formulation is provided as a dry or lyophilized powder which can be administered directly as a powder which hydrates at the site of application, or suspended or dissolved in a liquid, most preferably aqueous, and applied as a spray, paint, or injection or a hydrogel such as chitin, collagen, alginate, or synthetic polymer. In another embodiment, the formulation is administered as a compressed wafer, disc, or tablet. In still another embodiment, the formulation is provided as a coating on a device, for example a stent or a catheter, which may be dissolved in an aqueous solution and dried on the device, or mixed with a polymeric carrier and applied to the device. In yet another embodiment, the formulation is provided in a bandage, foam or matrix, in which the peptides may be dispersed or absorbed. The formulation could also be in the form of sutures, tape, or adhesive.

Conventionally, local anesthetics are delivered by topical administration (e.g., formulated as an ointment, cream, or solution) or injected into an area where the nerve fibers one wishes to block reside. The formulation may be administered to a burn or ulcer, especially when formulated with anesthetics, antiinflammatories, growth factors, and antiinfectives, in the form of a foam, matrix or bandage, to stop bleeding or loss of interstitial fluid.

One or more of the compositions described herein can be assembled in kits, together with instructions for use. For example, the kits can include a biocompatible composition including self-assembling peptides (or a concentrated solution or powdered formulation thereof, together with a diluent) and a vasoconstrictor, a coloring agent, or an analgesic or anesthetic agent and instructions for their combination (if not already combined) and use (e.g., dilution and administration). The kits can further include one or more of the additional agents described herein. These agents can be present within a peptide-based composition or packaged separately, and they can include one or more types of biological cells, an antibiotic or other therapeutic, collagen, an anti-inflammatory agent, a growth factor, or a nutrient. The kit may also include one or more of a syringe (e.g., a barrel syringe or a bulb syringe), a needle, a pipette, gauze, sponges, or cotton, swabs, a bandage, a nosebleed plug, a disinfectant, surgical thread, scissors, a scalpel, a sterile fluid, a spray canister, including those in which a liquid solution is sprayed through a simple hand pump, a sterile container, or disposable gloves.

The formulation can be administered as appropriate for treatment of one or more disorders. For example, the formulation may be applied to repair an injury or dealing surgery of the lung or dura, or following an epidural or spinal tap, to stop leakage of cerebrospinal fluid. The formulation may be dispersed in a suture or adhesive for administration at the time of or as released following suturing or gluing of a wound, thereby limiting bleeding, loss of tissue fluids, or other fluids such as those produced by parenchymal tissues such as the liver, pancreas, and gastrointestinal tract. The formulation may be applied to any site of bleeding, in a bandage, gauze, sponge, or other material, for immediate control of bleeding, or released later to control bleeding if the initial treatment such as suturing or pressure is insufficient. Dried fabric, dehydrated foams or hydrogels, or bandages containing the formulation may be part of first aid kids for treatment of injuries, for example, in war, at accident sites, or clinics where rapid treatment may be required and storage space is limited.

In some embodiments, compositions including self-assembling materials can be associated with surgical sponges. For example, liquid compositions can be drawn into commercially available sponges prior to or during their use. Studies indicate that hemostasis can be satisfactorily achieved without traditional sponges, but there may be instances where including compositions containing a self-assembling material may be beneficial (e.g., where a patient is experiencing profound bleeding or where the goal of treatment is temporary stabilization). The compositions employed can include any of the non-fibrous agents described herein. The sponges can be any known in the art, including woven and non-woven sponges and those designed specifically for dental or ophthalmic surgeries. See, e.g., U.S. Pat. Nos. 4,098,728; 4,211,227; 4,636,208; 5,180,375; and 6,711,879.

In embodiments featuring bandages or dressings, the bandage or dressing can include a first layer of sufficient shape and size to cover a wound or a substantial portion thereof (e.g., the most injured portion of the tissue or the area bleeding most profusely). The first layer can have a top surface, a bottom surface, and a perimeter that is, optionally, wholly or partially covered with an adhesive. A second layer of the bandage or dressing can be detachably affixed to the bottom surface of the first layer, optionally excluding the perimeter or any part of the perimeter bearing adhesive, and can include a liquid or non-liquid composition (e.g., a gel, paste, foam, cream, ointment, or powdered composition) including self-assembling peptides. The composition will come in contact with the wound upon application of the bandage or dressing and is transferable from the bandage or dressing to the wound site upon removal of the first layer or the first and second layers. In simpler configurations, the composition comprising self-assembling materials can be associated with the bottom of the first layer (e.g., interior to the adhesive perimeter), and the second layer can be omitted. In either case, either the first and/or second layers can include a transparent window, through which some or all of the underlying wound can be viewed. The composition including the self-assembling materials can be added to the bandage before it is packaged or just before use. In another embodiment, the formulation may include a further physical barrier, such as a layer of silicon film, to prevent loss of fluid by drying, after the active flow of fluids has been stopped by application of the formulation.

The formulations may also be administered as immediate or controlled release formulations. A delayed release dosage form is one that releases a drug (or drugs) at a time other than promptly after administration. An extended release dosage form is one that allows at least a twofold reduction in dosing frequency as compared to the drug presented as a conventional dosage form (e.g. as a solution or prompt drug-releasing, conventional solid dosage form). A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Matrix forming materials are materials which form strong, viscous gels upon hydration and provide control of drug diffusion and release. In hydrophilic matrix systems, matrix forming materials are uniformly incorporated throughout the tablet. Upon contact with water, the outer tablet layer is partially hydrated, forming a gel layer. The rate of diffusion of the drug(s) out of the gel layer and the rate of erosion of the gel layer determine overall tablet dissolution and drug delivery rates. Examples of matrix forming materials include cellulose ethers that are water-soluble such as methylcellulose, ethyl cellulose and hydroxypropyl methylcellulose.

Formulations are prepared using a pharmaceutically acceptable "barrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, matrix-forming compositions and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995) which provides information on carriers, materials, equipment and processes for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit™ (Roth Pharma, Westerstadt, Germany), Zein, shellac, and polysaccharides. Additionally, the coating material may contain conventional carriers such as plasticizers, pigments, colorants, glidants, stabilization agents, pore formers and surfactants. Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pre-gelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pre-gelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Some of the materials which are suitable as binders can also be used as matrix-forming materials such as hydroxypropyl methyl cellulose, ethyl cellulose, and microcrystalline cellulose.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pre-gelatinized starch, clays, cellulose, alginine, gums or cross linked polymers, such as cross-linked PVP (Polyplasdone™ XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium salts of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer™ 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

If desired, the tablets, beads, granules or particles may also contain minor amount of nontoxic auxiliary substances such as wetting or emulsifying agents, dyes, pH buffering agents, and preservatives.

In one type of formulation, the material can be utilized as a shaving cream or hand lotion additive, to form a barrier for loss of fluids and as a barrier to adhesions and contamination.

Extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include methyl acrylate-methyl methacrylate, polyvinyl chloride, and polyethylene. Hydrophilic polymers include cellulosic polymers such as methyl and ethyl cellulose, hydroxyalkylcelluloses such as hydroxypropyl-cellulose, hydroxypropylmethylcellulose, sodium carboxymethylcellulose, and Carbopol™ 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof. In certain embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

An immediate release portion can be added to the extended release system by means of either applying an immediate release layer on top of the extended release core using a coating or compression process or in a multiple unit system such as a capsule containing extended and immediate release beads. Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including *acacia*, alginates, methyleellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils. Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies. The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerolmonostearates may also be used. Pigments such as titanium dioxide may also be used. Small quantities of an anti-foaming agent, such as a silicone (e.g., simethicone), may also be added to the coating composition.

Polymeric Matrices

Both non-biodegradable and biodegradable matrices can be used for delivery of the self-assembling peptides, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provided more effective results. The polymer may be in the form of a hydrogel (typically in absorbing up to about 90% by weight of water), and can optionally be crosslinked with multivalent ions or polymers.

Representative synthetic polymers that can be used for delivery include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof. Examples of biodegradable polymers include synthetic polymers such as polymers of lactic acid and glycolic acid, polyanhydrides, poly(ortho) esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, polyhyaluronic acids, casein, gelatin, glutin, polyanhydrides, polyacrylic acid, alginate, chitosan, poly(methyl methacrylates), poly(ethyl methacrylates), poly(butylmethaerylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel. The polymer can also be in the form of a coating or part of a stent or catheter, vascular graft, or other prosthetic device.

The matrices can be formed by solvent evaporation, spray drying, solvent extraction and other methods known to those skilled in the art.

Bioerodible microspheres can be prepared using any of the methods developed for making microspheres for drug delivery, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988). The selection of the method depends on the polymer selection, the size, external morphology, and crystallinity that is desired, as described, for example, by Mathiowitz, et al., Scanning Microscopy 4, 329-340 (1990); Mathiowitz, et al., J. Appl. Polymer Sci. 45, 125-134 (1992); and Benita, et al., J. Pharm. Sci. 73, 1721-1724 (1984). In solvent evaporation, described for example, in Mathiowitz, et al., (1990), Benita, and U.S. Pat. No. 4,272,398 to Jaffe, the polymer is dissolved in a volatile organic solvent. The peptide either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres. In general, the polymer can be dissolved in methylene chloride. Microspheres with different sizes (1-1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of peptides. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000. Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used. In spray drying, the polymer is dissolved in methylene chloride (0.04 g/ml). A known amount of active drug is suspended (if insoluble) or co-dissolved (if soluble) in the polymer solution. The solution or the dispersion is then spray-dried. Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., Pharmazeutische Industrie 40-11A, 1230 (1978). Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethylene imide (PEI) can be prepared to reduce the amount of carboxyl groups on the alginate microcapsules.

Other delivery systems including films, coatings, pellets, slabs, and devices can be fabricated using solvent or melt casting, and extrusion, as well as standard methods for making composites. The polymer can be produced by first mixing monomers and peptides as described by Sawhney, et al., and polymerizing the monomers with UV light. The polymerization can be carried out in vitro as well as in vivo.

D. Devices for Administration

The liquid formulations may be provided in a syringe or pipette having a barrel containing a composition including self-assembling peptides and a means for expelling the composition from an open tip of the syringe or pipette (e.g., a plunger or bulb). The syringe may consist of one or more compartments, so that mixing of the self-assembling materials with one or more other agents occurs at the time of application. The compartments may also contain an excipient such as a material forming a hydrogel or adhesive in one compartment and the self-assembling materials in the other compartment. In another embodiment, one compartment may contain lyophilized powder or particles of self-assembling peptides, and another compartment may contain solution to dissolve or hydrate the peptides, or other powders to mix with the self assembling materials for dry application. The composition within the barrel can further include any of the non-fibrous agents described herein (e.g., one or more of a vasoconstrictor, a coloring agent, an anesthetic or analgesic agent, an antibiotic or other therapeutic, collagen, an anti-inflammatory agent, a growth factor, or a nutrient).

The self-assembling material can be applied as a coating by spraying or dipping the device into the material, the material can be impregnated into a bandage, gauze or other absorbent material, the material can be mixed with a polymeric material. The material can also be formulated as a pharmaceutical foam. Pharmaceutical foams are pressurized dosage forms that, upon valve actuation, emit a fine dispersion of liquid and/or solid materials in a gaseous medium. In one embodiment, the foam contains the self-assembling material, in liquid or solid form, optionally in combination with one or more active agents. Suitable propellants include, but are not limited to, hydrofluoroalkanes (HFAs), such as 1,1,1,2-tetrafluoroethane (HFA 134a) and 1,1,1,2,3,3,3-heptafluoropropane (HFA 227), hydrocarbons, and carbon dioxide.

II. Methods of Administration

A. Sites of Administration

The material can be applied to a variety of different surfaces to prevent or control fluid passage or to function as a barrier. The amount of self-assembling agent is determined in part by the function of the material in controlling fluid flow, as well as the properties of any other materials or structures associated with the self-assembling material, alone or in combination with other bioactive materials. The self-assembling materials can be used to stop the movement of fluids in or out of tissues/organs.

In a first embodiment, the material is used to prevent or control bleeding. The material may be applied as a powder, liquid, a gel, or as part of a substrate such as a bandage or membrane. This may be applied to a blood vessel, either within the lumen, for example at the time of angioplasty, administered by or as a coating on a stent or catheter, or exterior to the vessel, typically at the site of anastomosis. The material may be applied to tissues before, during or after surgery, to prevent bleeding, which is especially problematic with tissue such as liver, kidney or spleen, or other surgeries where there is a high risk of transfusion, or to seal and protect a tissue, for example, which is for transplantation or reattachment. In another embodiment, the self-assembling materials can be used as a shaving cream additive where they can act as hemostatic agents to stop bleeding due to razor cuts, a barrier to prevent contamination of razor cuts and/or a lubricant.

The material can be used to stop the flow of fluids other than blood. The material can be applied to burns to stop leakage of interstitial fluid. The material can be applied to the dura or lung as a dural or lung sealant. In one embodiment the material can be used to repair a lung after a puncture wound, thereby restoring its ability to function.

The material can also be utilized in general oral surgery, periodontistry, and general dentistry, as a barrier.

The use of the material in individuals with impaired coagulation (hemophilia, von Willebrands, vitamin K, protein S or protein C deficiency, 10 fulminant hepatitis, disseminated intravascular coagulation ("DIC"), hemolytic-uremic syndrome ("HUS")) is also an important utility since the mechanism of action is independent of the normal coagulation pathway. In another embodiment, the material is applied, typically by spraying or injection, to the exterior of a tissue such as a tumor, to prevent breakage or metastasis at the time of surgery. The material controls bleeding during tumor resection, as well as limits metastatis. This also minimizes the immune response that can be caused by a laser during tumor resection. The material is also useful in holding loose tumors together so that nothing is left behind when they are resected. There are several types of tumors that are notoriously hard to resect because they are not held together tightly (i.e. they are not solid masses). The material is expected to be particularly useful in tumor resection in the brain, and may be useful in a dose-response manner for subcutaneous tumor resection. This may make it easier to resect melanomas in the skin because it appears that the material also facilitates skin healing. The material can also include a marker reactive with certain types of antigens on the tumor cell surface, producing a colorimetric change to show that all of the cells have been removed or there are more that need to be resected. The addition of an indicator to the material as well as the ability of the material to act like a bio-barrier could reduce the need for second and third operations as well as complications due to outside contamination into the surgical field. The material can also be used to deliver materials such as DNA to the site of injury for an extended period of time in vitro and for multiple treatments in vivo. Another advantage of the material is that it can be injected and gel in place, so that the material can be applied and reapplied during surgery, as necessary.

In still another embodiment, the material is particularly well suited to functioning as a barrier to prevent contamination, either to the tissue or from the tissue, for example, during intestinal surgery. The material may be applied to prepare an internal site prior to surgery, especially sites such as the sinus cavities, and for surgeries such as transurethral and transvaginal surgery. The material should also be particularly useful in cardiovascular surgery, where both barrier and hemostasis properties can be of value, for example, for heart valve patients who are prone to adverse consequences such as valve ring abcesses (coat valve, add antibiotic), endocarditis (coat valve), aortic root dissection (provide immediate hemostasis).

The material in combination with a metal such as silver has anti-adhesive properties and can inhibit angiogenesis. Accordingly, it may be useful in decreasing scarring and adhesions. The material is applied after surgery, or to an injury such as a burn, to decrease scarring, fluid loss, and limit infection. This has further application in plastic surgery, especially for protection of areas cleaned and debrided prior to closure or skin transplant, for example, in abdominoplasty, face lifts, flap donor sites, latissimus dorsi for breast reconstruction.

In still another embodiment, the material is administered as a slurry that can be drunk by a patient to reduce stomach bleeding, for example, from an ulcer, or decrease acidity. Alternatively, the material could be provided as an enema or suppository to treat hemorrhoids or to fill in diverticula. In yet another embodiment, the material can be used to prevent infertility due to adhesions in the fallopian tubes or vas deferens.

An assembly is not irreversible, contained substances can be released. For example, the molecules or cells can be released from the structures in vivo (e.g., small molecules can diffuse away and larger molecules and cells can be released as the structures degrade).

In still another embodiment, the material is used as a neuroprotective to minimize damage and scarring following neural injury. Peptide-based structures promote repair and regeneration of neural tissue (e.g., when self-assembling peptides are applied to a lesion in the brain as described in U.S. Ser. No. 10/968,790). The small size of the fibers within the scaffolds and/or the open "weave" structure of the materials permits extension of cell processes and allows adequate diffusion of nutrients and waste products in a manner that provides unique advantages for neural tissue regeneration.

In the course of promoting wound repair, the compositions may not only improve the final outcome (e.g., reduced scar formation resulting in an outcome that more closely resembles the original tissue), but also reduce the time required for healing. These results could not have been predicted on the basis of the results achieved following application to the injured central nervous system, given the substantial differences between neural and non-neural tissues.

Finally, the materials could be used as "nanodrapes" to prevent cross contamination. For example, the materials could be applied as a coating to the outside of the body and then induced to self assemble. The self-assembled material may stop the movement of liquids into the body, the reducing the possibility of cross contamination.

B. Effective Dosages

In general, the amount of material required will vary depending on various factors such as the size or extent of an injury (which can, in turn, be expressed in terms of the length of an incision, the caliber or number of damaged blood vessels, the degree of a burn, the size and depth of an ulcer, abrasion, or other injury). The amount may vary, for example, from a few microliters to several milliliters or more, e.g., tens or hundreds of milliliters. The device used to deliver the material will vary in accordance with the amount. For example, a syringe can be conveniently used to deliver smaller amounts, whereas a tube or squeezable bottle would be more suitable for larger amounts. An effective amount (whether in reference to a scaffold, precursors thereof, or another bioactive molecule present in the formulation), means the amount necessary to elicit an improved or desired biological response.

As will be appreciated by those of ordinary skill in this art, the effective amount of an agent may vary depending on such factors as the desired biological endpoint, the agent to be delivered, the nature of the site to which the agent is delivered, and the nature of the condition for which the agent is administered. For example, an effective amount of a composition for accelerating hemostasis may be an amount sufficient to decrease the amount of blood lost between the time that bleeding begins and the time when bleeding ends by at least 25% relative to the amount of blood lost following treatment with cold saline or no treatment. An effective amount of a composition for accelerating hemostasis may also be an amount sufficient to decrease the time required to achieve cessation of visible bleeding by at least 25% relative to the time required following treatment with cold saline or no treatment. An effective amount of a composition for promoting wound healing may be an amount sufficient to decrease the time required to achieve a predetermined percent reduction in the size of a lesion by at least 25% relative to the time required in the absence of such treatment.

The amount of the composition provided can vary depending on the severity of the subject's condition and should be sufficient to inhibit the unwanted movement to an extent that benefits the subject. The bodily substance can be blood, cerebrospinal fluid, pus, serous exudate, bile, pancreatic juice, or a substance normally contained within the gastrointestinal tract (e.g., the stomach or intestine), or urinary tract.

C. How Administered

The composition can be provided on the surface of the subject's body and/or provided within a cavity generated by force (e.g., by unexpected trauma or a surgical procedure). In this way the unwanted movement of bodily substances can be inhibited in the context of a wide range of situations, including traumatic injury, a medical condition (e.g., a chronic or prolonged medical condition associated with bleeding), or surgical procedures (e.g., orthopedic surgery, dental surgery, cardiac surgery, ophthalmic surgery, or plastic or reconstructive surgery). For example, where the unwanted movement of the bodily substance is the result of trauma, the subject may have a partly or completely severed body part, a laceration, abrasion, puncture wound, or a burn. Where the compositions are applied to a surface of the body, they may not only inhibit the unwanted movement of a bodily substance, but also help protect the subject from contamination. For example, applying a self-assembling agent to the skin will impede the movement of an unwanted foreign substance on the skin or hair into a wound. When the unwanted movement of the bodily substance results from a chronic medical condition, the subject may experience recurrent bleeding. For example, the subject may be experiencing bleeding in connection with varicose veins, including telangiectases, hemorrhoids, bleeding in the lungs (due, for example, to lung cancer, bronchitis, or a bacterial or viral disease, including pneumonia or influenza), or esophageal varices. Medical conditions associated with recurrent bleeding can be treated with the compositions described herein, including those that contain self-assembling peptides and a vasoconstrictor (e.g., phenylephrine, which can constitute about 0.25-0.5% of the composition). Where bleeding occurs in the orophamyx or lungs, the compositions can be administered through a metered dose inhaler. If the patient's condition has deteriorated to the point where artificial ventilation is required, the compositions may be administered through a respirator or by lavage.

The unwanted movement of the bodily substance can also take place during a surgical procedure, and that procedure can involve an incision within the subject's nervous system, eye, ear, nose, mouth, pharynx, respiratory system, cardiovascular system, digestive system, urinary system, reproductive system, musculoskeletal system, liver, or integument. The methods can be carried out regardless of whether or not the movement of the bodily substance was intentional. The compositions described herein can be applied before or after the unwanted movement occurs (e.g., during a surgical procedure before the intentional transection of a blood vessel or after an unintentional transection of a blood vessel). For example, the surgical procedure can be carried out with the intent to repair an aneurysm, impede bleeding within the brain, to treat esophageal varices, to treat an ulcer or to inhibit the loss of gastric contents or intestinal contents (e.g., from a swollen or ruptured appendix). The surgical procedure can involve resecting a portion of the subject's intestine. Other procedures that can be carried out with the assistance of compositions including self-assembling agents include arteriography, cardiac catheterization, insertion of a stent, assistance with a natural birth or birth by Caesarean section, hysterectomy, organ transplant, joint replacement, or excision of an intervertebral disk. These procedures are representative. The surgical procedure can be performed with the assistance of an endoscope or laparoscope, and the compositions can be delivered independently or from a chamber situated within these devices and connected to a distal end by a passage for release onto the subject's tissues. Where the patient has an ulcer, that ulcer can be an esophageal, gastric, duodenal, diabetic, or decubitus ulcer. More generally, the compositions can be applied to any disrupted area of the skin, and any of the methods described herein can include a step of identifying a patient in need of treatment.

A self-assembling peptide nanofiber scaffold (SAPNS) can provide a transparent environment for the surgical field, while also creating an optically clear liquid that allows operation through the resultant liquid and gel mix. The surgical field is often obscured with blood and debris during an operation. In addition, clearing debris from the surgical field usually requires irrigating the site with saline. Saline is only a temporary solution and needs to be continuously applied to maintain a clear surgical field. This poses several issues: any contamination in existence will easily spread; a small opening will require alternating between irrigation and operating; and during intestinal operations use of saline can result in a massive infection leading to post-operative complications. Using the SAPNS for biological confinement will reduce post operative complications in endoscopic and open surgical procedures. Efficacy has been demonstrated on brain, spinal cord, gastrointestinal tract, liver, muscle, arteries and veins.

For example, a partial resection is currently performed as follows. The surgeon performs a partial resection of the intestine to remove a precancerous area. The incision is made and the intestines are gently lifted out of the intraperitoneal cavity and placed on the table next to the patient. The offending area is resected and the two ends of the intestine are then ligated together. Before the intestines are put back in the body there is a colostomy bag connected to the upper end of the intestine and the area of the operation is disinfected. The intestines are replaced in the abdomen and are sewn back up. A drain is placed in the abdomen to make sure there is no leakage or bleeding. In contrast, using the self-assembling peptide material, a partial resection is performed as follows. The doctor opens the abdomen and finds the offending part of the intestine. It is isolated with additional liquid that is poured into the intraperitoneal cavity to isolate it from the rest of intraperineal cavity. The surgeon reaches through the gel that was formed by the liquid and resects the intestine. The two ends are ligated together and the area is checked for any changes in color. Because the gel also has an indicator die that changes to blue if there is any leakage of gastric fluids or bacteria. All of the blue is removed with suction. A little more material is sprayed around the area of the repair and the abdomen is sewn up.

Scar Treatment: Experiments have demonstrated that application of the self-assembling material can be used to block formation of scarring in the central nervous system (CNS). Administration of the materials at the site of lesion blocks the stable formation of a scar, which can permit regeneration through that site. Removing the scar that develops in the central nervous system (CNS) permits axons to grow across the injury site.

Chelation Enhanced Wound Healing: The material can be used for the delivery of a chelator such as iron to a site so it can be used by the body in the local environment to rebuild basement membrane. In tissues that do not contain enough iron, the delivery of iron in a stable form will help healing and the rebuilding of tissue. Metals with a cystine or cystine like residue can be incorporated in the nanomaterial so there is little or no steric hinderance with the assembly of the matrix in-vivo or in-vitro.

In summary, the self-assembling peptide material can be used to create a clean local environment to perform surgery; isolate structures and migration of contaminates; inflate structures for surgical procedures, i.e. intestine; surround structures that are being removed that may leak, i.e. appendix, patch holes in body; allow for surgery in dirty environments; used with scope procedures to surround the organ before the operation to contain any leakage; used to create a barrier to prevent adhesions while performing abdominal surgery; and used for form a gasket between the scope and the insertion point of the scope. Benefits during surgery are that the material is optically clear, has a long shelf life at room temperature, can be operated through it, shortens prep time, eliminates counting sponges, isolates each structure in the surgical field, shortens clean up time of the operating room, shortens surgical time, reduces or eliminates cross contamination caused by other irrigants, the material is biocompatible, the breakdown products are natural and are absorbed by the body. The material is easy to manipulate, can be injected at the location needed, should eliminate Staphylococcal infections, may be able to reduce the cost of surgical theater disposables paper, reduce biohazard bags since the material can be boiled to sterilize after the procedure to yield steam. Since the material is clear it should enable the surgeon to operate faster because the operating field is clear of blood. The elimination of wound packing to control bleeding could reduce the operating time as much as 50% in a complicated case. Post-op infection, due to secondary infection, may be reduced by the use of the material since it can coat the wound during and after surgery, thus reducing contamination from foreign bodies. Post-op care may be able to use the material to reduce infection due to drainage by slowing the spread of particulate material in the abdomen or chest cavity.

While the compositions can be removed from a site of application (e.g., a bleeding vessel) at any time, a physician may wish to allow them to remain in place even after the initial goal of promoting hemostasis has been achieved in order to promote wound healing.

Where the compositions include self-assembling peptides, those peptides can include amino acid residues that are naturally occurring and that can be absorbed by the body. The compositions are not difficult to manipulate, and they can be easily dispensed on an as-needed basis. Their features (e.g., stiffness) can be altered readily by altering the concentrations of components therein (e.g., by altering the concentration of self-assembling peptides in a given composition). As the resulting, assembled structure does not significantly impair one's view of an underlying tissue, and does not have to be removed before a procedure can be carried out. For example, a physician can assess a burn or other surface trauma that has been treated in the field with a composition described herein. In the operating room, a surgeon can make an initial incision through the material and can continue to operate with standard equipment, such as scalpels and clamps, or more modern means, such as lasers, in an internal field to which the compositions may also have been applied. Another advantage may be realized in time, as use of the compositions can decrease the time required to prepare a patient for surgery. As the compositions can be applied around the site of an incision and form a coating to protect against infectious agents, there is less need to shave a patient's skin, apply drapes, and apply disinfectants.

Given the structural integrity of the assembled scaffolds, they can be removed from an area in which they have formed if desired. Thus, an assembled scaffold can be removed by, for example, suction, or by lifting it away with an instrument such as forceps, or wiping it away with a swab or gauze. For example, the scaffold can be removed after hemostasis is achieved or in the course of cleaning a wound. Based on studies to date, the scaffold or a majority thereof can be removed without damaging the underlying tissue. Where the assembled scaffolds are formed ex vivo, they can be removed from a mold and used subsequently (e.g., implanted in a tissue or tissue void). The compositions should reduce the amount of material that requires disposal or cleaning afterward (e.g., surgical drapes, sponges, and other biohazards).

"Nanodrapes" can be used to replace traditional paper or cloth drapes, by limiting infection following application directly to the patient, for example, by spraying or otherwise coating the patient or the area around the surgical incision. Currently a patient is prepared for surgery by shaving, scrubbing, disinfecting and draping after positioning on the surgical table. Then bactericide and tape is applied to the area where the surgery is to be performed. The self-assembling composition can be applied in place of drapes by spraying the warm liquid onto the body where it self-assembles into a thin second skin. This material has a pore size that is smaller than any bacteria can fit through, so it protects from any airborne contaminants, and because the one millimeter thick material can contain a mild antibactericide, that clings to the body like a second skin. The material can also have a hydrating component for the skin so it does not dry out. There is no worry about getting the material into the wound site because it will be broken down by the body. Color can be added to it so it is easier to determine if it is all washed off after the operation.

A scaffold (e.g., a nanoscale structured material) can be provided by introducing, to a subject, a precursor of the scaffold at a location, or in the vicinity of a location, where the scaffold is desired (e.g., to control movement or leakage of a bodily substance, to protect a wound, or to promote tissue repair). Precursors (e.g., self-assembling peptides) are provided in the vicinity of a location when they are provided at a position that is close enough to the targeted area (e.g., a bleeding vessel, a diseased section of the digestive tract, or an area of burned skin) that they reach the targeted area in an effective amount. The precursors, which may be homogenous or heterogeneous (e.g., one may apply a single type of self-assembling peptide or a mixture of two or more different such peptides), can be contained within a composition and, upon contact with physiological conditions, assemble to form the scaffold (e.g., a nanoscale structured material). Thus, the precursors can assemble in situ (i.e., within the body of a subject at or in the vicinity of administration).

The nanoscale structured material may include, or its assembly may involve, additional components present in situ, (e.g., ions). Thus, precursors such as self-assembling peptides can be applied in a solution that is substantially free of ions (e.g., substantially free of monovalent cations) and self-assemble to form a macroscopic structure when they come in contact with such ions in the body (e.g., in a bodily substance such as blood, gastrointestinal contents, and the like). For example, a solution containing precursors can be applied at, or in the vicinity of, a site of gastric or intestinal perforation or a site where a surgical incision has been or will be made.

The scaffold can also be provided in the form of a gel, as the precursors (e.g., self-assembling peptides) can be assembled prior to introducing a composition to a targeted area (e.g., the site at which an incision will be made for a surgical procedure). The assembled structure may assume any convenient shape.

The scaffold can also be provided by providing precursors in the form of a dry powder. A "dry" powder will have a relatively low liquid content (e.g., sufficiently low that the particles therein are readily dispersible). Self-assembling peptides provided in the form of a dry powder will assemble when they come into contact with a bodily fluid containing monovalent cations, and a solution containing such ions may be added if desired to alter the rate at which the scaffold forms or its stiffness. Self-assembling peptides may be provided as emulsions or, as described above, molded into preformed shapes that can be inserted into a body cavity or wound site in a manner similar to the manner that surgical sponges are currently used. If desired, a binder can be added to a dry powder which is then formed into a desired shape. Regardless of the precise manner in which the scaffold is assembled (e.g., whether by bringing a liquid formulation containing precursors into contact with the body or a dry powder into contact with an ion-containing solution ex vivo), the formed scaffolds can assume a desired shape. Where the size and shape is such that the scaffold fills the lumen of a blood vessel, the scaffold can be used a vascular plug.

A preventative measure can be carried out before a subject experiences an unwanted event (e.g., before an injury occurs or before bleeding begins). Thus, the site of administration can be a site of potential movement or potential leakage, and the application can be made to prevent or minimize such movement or leakage should it occur. When used in the context of a therapeutic procedure or treatment, the compositions can reverse, alleviate, or inhibit the progress of a condition (e.g., a state, syndrome, disease, or a sign, symptom, or manifestation of such). Methods of treating a subject are generally carried out once the subject is recognized as having a condition amenable to treatment, and any of the methods described herein, whether best described as prophylactic or therapeutic, can include a step of identifying an amenable subject.

As the compositions described here can be used to inhibit movement of a bodily substance in a subject, including movement within or from the epidermis, the compositions can be employed in the context of performing surgery and may be described as new methods for performing surgery or generating a surgical field. The methods, whether performed in the context of surgery or not, can include a step of identifying a subject in need of treatment and a step of providing a nanoscale structured material, or a precursor thereof, at or in the vicinity of a site where unwanted movement has occurred or is expected to occur. For example, one can identify a patient who is about to undergo a surgical procedure and provide a biocompatible composition comprising self-assembling peptides and a vasoconstrictor, a coloring agent, or a local anesthetic agent to a site at which an incision or other invasive maneuver will be made or has been made. The bodily substance that is affected may be a fluid such as blood or a blood product, serous exudate (an inflammation-associated exudate composed largely of plasma, which typically appears as a clear or amber-colored fluid), pus, gastric juice, urine, bile, cerebrospinal fluid (CSF), pancreatic juice, and the like. The bodily substance may be viscous, sludge-like or semi-solid but will generally exhibit an ability to flow or move. Substances of this nature include the contents of the gastrointestinal tract. The composition may be removed after application (e.g., after hemostasis is achieved or an operation on the bowel is complete) or may be left in place. For example, the compositions can be applied to accelerate hemostasis or inhibit movement of intestinal contents during surgery and some or all of the scaffold may be left in place when the operation is complete. This provides a substantial advantage relative to the use of sponges and other materials that must be removed prior to closure. The compositions can be removed in a variety of ways (e.g., by wiping or by suction).

The compositions can also be applied to shield an underlying area (e.g., an area of burned or otherwise injured skin or other tissue) and can, therefore, help to prevent contaminants (e.g., foreign substances) from coming into contact with the area (i.e., the compositions can be used as a barrier or shield). A physician or other health-care provider can examine a wound through the material, and a surgeon can operate through it, while it is in place. Contaminating substances that have landed on the material during the procedure could then be removed by virtue of removing the material.

The compositions can be administered to stabilize a wound prior to definitive treatment (e.g., while the victim is awaiting transport to a hospital or during transit). The compositions are similarly useful where operations are conducted under conditions of less than optimal sterility (e.g., in field hospitals or in areas of the world where access to sterile operating rooms is limited). The compositions and methods have the potential to significantly reduce the likelihood of contamination in instances such as these.

The self-assembling peptide material can also be locally applied in combination with anesthetic in the local area where a procedure is to take place and can be applied at a higher concentration to reduce organ movement during surgery. This may reduce cognitive deficits to older patients by reducing the general anesthetic load. A thin layer can be sprayed on the tissue or skin where the surgeon is operating. It can be applied separately or together, administering specific anesthetic for specific organs. Skin has different receptors than intestines and the need for a specific anesthetic is needed for each of the organs. Intestines need to stop moving during surgery while the blood and blood vessel contraction need to remain constant.

Treatment and Prevention of Bleeding: Any individual who has an increased risk of suffering undesirable bleeding, which may or may not be excessive or immediately life-threatening, can be treated with the compositions described herein. These individuals include those with blood clotting disorders such as hemophilia, patients who are receiving anticoagulant therapy, patients who suffer recurrent nosebleeds, and individuals undergoing surgery, particularly major surgery or procedures that involve accessing an artery. Without limitation, the surgery or procedure can be an operation on the nervous system, eye, ear, nose, mouth, pharynx, respiratory system, cardiovascular system, digestive system, urinary system, musculoskeletal system, integumentary (skin) system, or reproductive system. Specific examples of surgeries and procedures in which the compositions can be used include arteriography, angiocardiography, cardiac catheterization, repair of obstetric laceration, removal of coronary artery obstruction, insertion of stent, Caesarean section, hysterectomy, reduction of fracture, coronary artery bypass graft, cholecystectomy, organ transplant, total joint (e.g., knee, hip, ankle, shoulder) replacement, appendectomy, excision or destruction of intervertebral disk, partial excision of the large intestine, mastectomy, or prostatectomy.

Accident victims, individuals engaged in combat, and women giving birth are also at risk of experiencing significant blood loss. The compositions can be applied to a site of obstetric bleeding (e.g., within the uterus, vagina, or neighboring tissue) in order to accelerate hemostasis. For example, the compositions can be applied to a placental tear or used to pack the uterus to control bleeding. As with other indications, compositions applied to the reproductive tract can be removed or left in place. Spontaneous hemorrhage, aneurysm rupture, esophageal varices, gastric ulcers, ulcers of the upper portion of the intestine (e.g., duodenal ulcers) are also medical conditions in which considerable bleeding can occur, and these individuals can also be treated as described here.

The precise source of the bleeding can vary and can be from any blood vessel in the arterial or venous system (e.g., an artery, arteriole, capillary or capillary bed, venule, or vein). The size of the vessel may range from large (e.g., the compositions can inhibit bleeding from the aorta, the iliac or femoral artery, or a portal vein) to small (e.g., a capillary), and the vessel may be located anywhere in the body (e.g., in a solid organ such as liver, the stomach, intestine, skin, muscle, bone, the lungs, or the reproductive system).

The time normally required for blood clotting can be prolonged when plasma levels of clotting factors and/or platelets are low or in cases in which an individual has received an anticoagulant (e.g., warfarin or heparin). Bleeding frequently persists for considerably longer than the average clotting time when there is more than minimal damage to blood vessel integrity. Based on the studies, it is expected that the compositions will cause hemostasis in a period of time that is less than, and in at least some cases much less than, the average blood clotting time. Although the compositions are not limited to those that achieve hemostasis in any given time (and uses such as protecting an area from contamination or promoting tissue healing are independent of this function), the compositions may confer a benefit to a bleeding subject in as little as five seconds following application. Other compositions can exert an effect in about 10, 15, or 20 seconds following application. The effective period can be characterized in a manner other than absolute time. For example, compositions may reduce the time required to achieve hemostasis by between 25% and 50%; between 50% and 75%; or between 75% and 100% relative to the time required when iced saline is applied. The time required to achieve hemostasis can be reduced by approximately 2-, 3-, 4-, or 5-fold relative to the time required when iced saline is applied.

The peptide concentration may be selected with reference to variables such as the caliber of the vessel, the extent to which it has been injured, and the force with which blood is exiting (or would exit upon injury). Higher peptide concentrations will be desirable to promote hemostasis from a major vessel (e.g., the aorta, brachiocephalic, carotid, subclavian, celiac, superior mesenteric, renal, iliac, femoral, or popliteal arteries). Useful concentrations can range from between approximately 0.1-10% (e.g., 1-10%; 0.5-5%; 14%; 0.1-2%; 0.1-3%; 0.1-4%; 0.1-5%; and 1-8% (e.g., about 1, 1.5, 2, 2.5, 3, 4, 5, 6, or 7%). Any subrange, or any specific value within any of the aforesaid ranges, can be used. Any of the aforementioned concentrations may also be used for the other indications described herein.

As noted, bleeding can be due to any of a large number of different causes and can be internal or external. The compositions can be applied regardless of the cause or the nature of the cause (e.g. whether caused by a disease process or intentional or accidental trauma). The compositions can be used to achieve hemostasis in a confined space (e.g., inside a hollow organ) or at or near the body's surface. For example, the compositions can be applied to a partly or completely severed body part such as a limb or digit. In that event, the compositions may be serving multiple functions; they may not only promote hemostasis, but also protect the wounded tissue from contaminants and promote tissue healing. More specifically, the compositions can be applied to a wound, left in place for a period of time sufficient to achieve hemostasis and for blood clotting to occur, and then removed. Contaminating material such as particulates and infectious agents adhered to the peptide gel would be removed with it. A sterile dressing may then be applied. Of course the compositions can be applied for purposes of cleaning a wound, preventing contamination, or promoting tissue healing even after hemostasis has been achieved or in situations in which acceleration of hemostasis is not needed.

When used to treat a nosebleed, the compositions are inserted into the appropriate nostril and can be left in place until the bleeding has subsided. The compositions can be easily removed by suction (e.g., using an eyedropper or syringe) or may be removed by other physical means, including simply blowing the nose.

The compositions can also be left in place on a wound, and a dressing can be applied over the composition. Since the composition itself is easily removed, its presence under the dressing can help prevent the dressing from sticking to the damaged tissue. If desired, a bandage having a transparent portion may be used so the injured site can be viewed through the transparent portion of the bandage and the peptide structure below. This would allow a physician to monitor the progress of the healing without removing the dressing. Modified bandages are described further below and are within the scope of the present invention.

Many medical procedures involve vascular puncture, which can be followed by significant bleeding. A self-assembling peptide composition can be applied to the wall of a punctured vessel, e.g., during withdrawal of an instrument used to puncture the vessel. A vascular plug formed from self-assembling peptides provides an alternative to existing vascular plugs and devices such as those described in U.S. Pat. Nos. 5,192,302; 5,222,974; 5,645,565; and 6,663,655. The vascular plug can be formed in situ (e.g., at a site of vascular puncture), or can be preformed and applied to the site.

More generally, compositions comprising nanostructured materials or precursors thereof (e.g., self-assembling peptides) can be used for sealing any passage through tissue. The present methods therefore include methods of sealing a passage through tissue by applying a composition comprising a nanoscale structured material (e.g., self-assembling amphiphilic peptides) to one or both ends of the passage or to its interior. The tissue can be, for example, the wall of a blood vessel, the wall of an organ, subcutaneous tissue, or adipose tissue. Sealing the passage can result in hemostasis. The passage can also be a fistula (i.e., an abnormal connection between two organs or body structures or between an organ or structure and the external world). If desired, a surgeon can apply the compositions to the interior of a tubular structure such as the intestine or a blood vessel, resect and ligate the intestine or blood vessel in the gel, and evacuate the gel from the interior of the structure to restore continuity of the structure and allow reperfusion of the area with blood or other body substances. The materials may also be used to limit reperfusion injury. For example, the self-assembling materials can be administered post ischemia, such as to patients who have been treated with a thrombolytic agent. The materials may also be used to limit reperfusion injury through the re-establishment of blood tissue barriers prior to, during, and/or after reperfusion. For example, the self-assembling material may be used to re-establish blood tissue barrier through the internal coating of portions of the circulatory system. This may be beneficial in diseases such as ischemic infarction, hemorrhagic stroke, or reperfusion injury. Finally, the self-assembling materials may be used to limit reperfusion injury through the re-establishment of the integrity of the vascular structure prior to, during, and/or after reperfusion.

For surgical applications, the wound or any part of the surgical field can be packed with a composition comprising self-assembling peptides. This approach can be used instead of wound packing as it is conventionally performed during surgery. As the compositions contain biocompatible and biodegradable material, they can be left in place, thereby avoiding the need for removal at the end of the procedure and avoiding the need for a subsequent operation for this purpose. Biodegradable materials can be broken down physically and/or chemically within cells or within the body of a subject (e.g., by hydrolysis under physiological conditions or by natural biological processes such as the action of enzymes present within cells or within the body) to form smaller chemical species which can be metabolized and, optionally, reused, and/or excreted or otherwise disposed of. Preferably, the biodegradable compounds are biocompatible.

Gastrointestinal bleeding, which can occur as a consequence of ulcers or angiodysplasia, is a relatively common and serious condition that can be fatal if left untreated. Bleeding esophageal varices, and bleeding gastric or duodenal ulcers can be particularly severe. A number of endoscopic therapeutic approaches have been developed to achieve hemostasis, such as the injection of sclerosing agents, the attachment of mechanical hemostatic devices, and contact electrocautery techniques. The compositions can be administered at, or in the vicinity of, an ulcer or a site of bleeding in the esophagus, stomach, small intestine, or large intestine. Bleeding in the distal portion of the large intestine, rectum, or anus (e.g., hemorrhoids) can also be treated in this manner.

Rupture of an aneurysm can represent a catastrophic event with rapidly fatal consequences. Ruptured aortic aneurysms can rapidly result in exsanguination despite prompt medical attention. Ruptured intracranial aneurysms frequently have devastating consequences. The compositions and methods of the invention can be used to treat bleeding from a ruptured aneurysm in an essentially similar manner to the way in which they are used to treat bleeding due to other causes (e.g., by application of self-assembling precursors or a preformed structure to the site of bleeding). Given the often severe consequences of aneurysm rupture, surgical repair is often attempted. The compositions can be applied in the context of any attempted repair (e.g., during open surgery or endovascular repair (e.g., with placement of a graft and/or stent)). More specifically, the present methods include treating an aneurysm by introducing a composition comprising a nanoscale structured material or precursor thereof (e.g., a composition comprising self-assembling peptides) into the aneurysm (e.g., into the aneurysm sac). Once any bleeding is under better control, the aneurysm may then be repaired using any suitable technique. Presence of the peptide structure within the aneurysm sac reduces the chance of leakage or rupture prior to or during these other procedures. The scaffold can be left in place.

Inhibiting Movement or Leakage of Cerebrospinal Fluid (CSF): The dura mater is the tough, outermost, fibrous membrane that covers the brain and spinal cord, and lines the inner surface of the skull. Leakage of CSF is a significant complication following injury, surgery, or other procedures in which the dura mater is penetrated, including inadvertent penetration in the course of administering an anesthetic to the epidural space. Such leakage can lead to serious sequelae, such as severe headaches, infection, and meningitis. The composition can inhibit movement or leakage of CSF in a subject in need thereof after application at, or in the vicinity of, a site of unwanted movement or leakage of CSF. The compositions can be applied over sutures following dura mater surgery to help prevent CSF from leaking out of the incision site. The compositions can also be used to inhibit movement or leakage of fluid from the ear drum.

Inhibiting Leakage of Contents of the Gastrointestinal Tract: The compositions can inhibit the movement of gastrointestinal contents. For example, the structures can prevent leakage of gastrointestinal contents following gastric or intestinal perforation or during surgery (see Example 4). The structures can be used to isolate such bodily substances and prevent their spread within the peritoneal cavity, thereby minimizing contamination and the risk of subsequent chemical peritonitis and/or infection. Gastric contents, which contain digestive secretions of the stomach glands consisting chiefly of hydrochloric acid, mucin, and enzymes such as pepsin and lipase, can cause injury and/or infection if released into the peritoneal cavity. Release of intestinal contents into the peritoneal cavity represents a frequent event during surgery on the intestine and can also occur in cases of intestinal perforation or a ruptured appendix. The composition can be used to inhibit leakage of gastrointestinal contents into the peritoneal cavity. The site of movement can be a site of gastric or intestinal damage caused by a disease process or a surgical incision. The compositions can be applied to the exterior of any organ in the digestive system (e.g., the stomach, or small or large intestine) or can be injected or otherwise introduced into their interior. The compositions can be administered in the course of resecting a segment of the intestine. For example, one can fill a segment of intestine that extends from a first point to a second point with a present composition and resect a portion of the intestine that lies between the first and second points. In one embodiment, the self-assembling material may be used to treat heartburn. For example, the self-assembling materials can be formulated as a solution, suspension, or emulsion (such as a drink or shake), gel, tablet, wafer, capsule, etc. that is administered orally in order to coat portions of the gastrointestinal tract. The formulations can be used to: stop the movement of bodily fluids including, gastric juices and blood; coat the GI tract, and/or stop the progression of ulcers, erosion, and inflammation. The formulations may be used to prevent damage to the esophagus from acid reflux disease. The formulations may also used to help the repair of cells in the esophagus that were damaged by acid reflux, other diseases or disorders, and/or therapeutic interventions. The formulations may be used to help the repair of primary and secondary ulcers and erosions to the mucosa. The formulations may be used to deliver therapeutic, prophylactic, and/or diagnostic agents to portions of the GI tract as needed. For example, the self-assembling materials may be used to deliver agents to re-establish the flora and fauna of the GI tract which have been deleted to radiation treatment and/or disease or trauma.

In a related method, one can use the compositions to remove intestinal contents that have been released into the peritoneal cavity. The method includes applying a liquid composition to the released intestinal contents, allowing the liquid composition to undergo a phase transition, and then removing the gel-like or semi-solid composition. These steps can be repeated once or more until the surgeon is satisfied with the amount of intestinal contents that have been removed from the peritoneal cavity.

One can similarly inhibit movement of the contents of other internal organs (e.g., organs in the biliary or urinary systems). For example, one can inhibit movement of bile, pancreatic juice (i.e., secretions of the exocrineportion of the pancreas that contain digestive enzymes), or urine and/or decontaminate or clean an area into which bile, pancreatic juice, or urine have been released by application and subsequent removal of the compositions to the site. The methods thus have broad application to surgeries for repairing or otherwise treating intestinal, biliary, and/or urinary system defects.

Wound Healing: Studies also indicate that the compositions have the ability to enhance healing, particularly of an epithelial layer or muscle, and can therefore be administered to treat a site of tissue damage. For example, one can apply a composition including self-assembling peptides to the site of tissue damage. The compositions appear to both increase the rate of tissue repair and inhibit formation of scar tissue. The compositions can be used for either acute or chronic wound care. For example, they can be applied to skin wounded in any manner (e.g., lacerated or burned) and to lesions such as diabetic ulcers and pressure sores.

These materials can be used to maintain hydration and nutrition to patients that have had burns or in cases the outer skin has been breached due to abrasion or burn.

In another case the material can be used to maintain body temperature when the patient is covered with the material by means of external heat or cooling source.

Tissue Regeneration

Drug Delivery Vehicle to the Intrathecal Space: The materials described herein may be used to deliver therapeutic and/or imaging agents to the intrathecal space. Examples of therapeutic agents include, but are not limited to, anti-inflammatory agents and agents to stimulate nerve/spinal cord regeneration. Hydrogel material have been used to attempt to delivery of one or more active agents to the intrathecal space. However, these materials can be limited by their slow polymerization times, which allows for the material to diffuse away before the material polymerizes to form the gel. The materials described herein can be designed to self-assembly quickly so that the material does not diffuse away.

Cartilage Repair: The materials described herein may be used for cartilage repair. The materials would typically be injected into the site where cartilage repair is needed. The material can used alone or in combination with cells and/or growth factors.

Bone Regeneration: The materials described herein may be used to prepare composite materials for bone regeneration. For example, the self-assembling materials can act as a carrier for inorganic materials, such as calcium phosphate or hydroxyapatite, organic materials, such as growth factors, and/or bone grafts. Inorganic materials such as calcium phosphate can be remodeled by the osteoclast resorption mechanism to regenerate bone. The materials may also be injected under the periosteum to stimulate bone growth as a means for creating bone grafts in vivo. Alternatively, the materials described may be used for guided bone regeneration therapies which limit fibrous in growth. For example, the materials described herein may be used in dental procedures as molds which are placed over the tooth socket to prevent fibrous tissues from growing into the socket space.

Oxygen Delivery: The self-assembling materials described herein may also be used to deliver oxygen to the lungs and/or other organs. For example, the materials can be superoxygenated to provide oxygen support/perfusion for patients suffering from pulmonary hemorrhage and other lung diseases.

Delivery Methods, Devices, and Kits: A variety of devices can be used to introduce the compositions to a target area of the body. The devices can be simple, such as a syringe, and such devices can be provided together with the compositions in kits. The composition can be locally delivered at or near a target area in the body by injection (e.g., using a needle and syringe), or with a catheter, cannula, or by dispensing (e.g., pouring) from any suitably-sized vessel. The compositions can be delivered with the assistance of imaging guidance (e.g., stereotactic guidance) if necessary. Alternately, a material can be wetted with the composition and then used to apply a composition to an area of tissue.

For storage and shipping, self-assembling materials can be dissolved in a suitable solvent (e.g., an aqueous medium such as sterile water, and stored for long periods of time prior to use). Peptide-containing solutions have been stored for up to two years without substantial loss of activity. If partial self-assembly occurs after a prolonged period of time, physical agitation (e.g., sonication) can be used to restore the material to a more liquid state prior to administration. Alternatively, the material can be applied as a gel. If desired, a small amount of ions (e.g., monovalent cations) can be added to a solution prior to application. This may speed the process of gel formation. Alternately, monovalent cations can be applied after the solution has been administered.

Kits containing syringes of various capacities or vessels with deformable sides (e.g., plastic vessels or plastic-sided vessels) that can be squeezed to force a liquid composition out of an orifice are provided. In one embodiment, the syringe or vessel contains multiple compartments, one containing monovalent ions, and the other self-assembling peptides, which are mixed at the time of administration, through a common needle. An endoscope can be used to deliver the compositions for treatment of a hollow organ (e.g., the esophagus, stomach, intestine, etc.) or body cavity (e.g., during minimally invasive surgery). Minimally invasive surgery refers to an approach to surgery whereby operations are performed with specialized instruments designed to be inserted through small incisions or natural body openings, often performed with endoscopic visualization. Examples include laparoscopic surgery, arthroscopic surgery, and endovascular surgery. An endoscope is typically a long, flexible tube-like device. In addition to allowing visualization of internal structures, many endoscopes have additional diagnostic (e.g. biopsy) and therapeutic capabilities (e.g. delivery of therapeutic agents) through special channels. Colonoscopes, sigmoidoscopes, bronchoscopes, cystoscopes, and laparoscopes, are variants of an endoscope having features making them particularly well suited for viewing certain organs, structures, or cavities. Any of these devices can be used to deliver the compositions. Kits may be packaged including an endoscope and a vessel containing a solution comprising self-assembling peptides. Suitable endoscopes are known in the art and are widely available. Endoscopes are currently in use to deliver sclerosing agents to sites of esophageal bleeding.

Kits can include self-assembling peptides and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. The peptides can be in solution or dry (e.g., as a drypowder). Components of the kit may be packaged individually and are sterile. The kits are generally provided in a container, e.g., a plastic, cardboard, or metal container suitable for commercial sale. The kit may be styled as a "first aid kit," in which case it will typically have a symbol such as a red cross on the exterior. Any of the kits can include instructions for use.

EXAMPLES

Example 1

Self-Assembling Peptide Material Accelerates Hemostasis in the Brain

Complete transection of a branch of the superior sagittal sinus in the brains of rats and hamsters was performed after removing a portion of the skull overlying the transected tissue. Animals were anesthetized with an i.p. injection of ketamine (80 mg/kg) and xylazine (8 mg/kg). All surgical procedures were conducted under an operating microscope. Twenty-two animals, including 10 adult hamsters and 12 young adult female Sprague-Dawley rats (200-250 g), were treated with either iced saline or 20 µl of a 1% peptide solution at the site of the sinus branch transection. The material was prepared by dissolving RADA 16-1 (n-RADARADARADARADA-c; SEQ ID NO: 1) peptide in sterile water, and the peptide-containing solution was applied to the injured tissue with a 31 gauge needle attached to a 2 cc syringe.

The experiment was videotaped with a time stamp and was replayed one frame at a time to evaluate the length of time required for the peptide solution to form a gel, which effectively impeded bleeding. Hemostasis was assessed visually, and "complete hemostasis" was defined as the complete lack of movement of blood from the wound site. Complete hemostasis was achieved within 10 seconds of the application of the peptide solution in all cases.

A series of pictures was taken of an adult rat in which a portion of the overlying skull was removed and one of the veins of the superior sagittal sinus was transected and then treated with a peptide-containing solution. The initial picture shows the exposed brain and veins of the superior sagittal sinus; the next picture shows the cutting of the vein; the next picture shows bleeding from the ruptured vein; and the final picture shows the same area five seconds after the peptide solution was applied. Complete hemostasis was achieved.

Durations were measured from the start of application of peptide solution to the completion of hemostasis after transection of the veins leading to the sinus in the brains of adult rats. Complete hemostasis was achieved in an average of 8.3 seconds. In the saline controls, cessation of bleeding was never achieved. The saline control experiment was terminated at the same time point in order to prevent the animals from bleeding to death.

Similar results have been obtained following complete transection of the superior sagittal sinus. A higher concentration of peptide (e.g., approximately 3%-4%) was used in the latter experiment in order to achieve hemostasis. The three saline control cases continued to bleed after 20 seconds. In the control animals, the iced saline was removed and the peptide solution was applied, resulting in complete hemostasis almost immediately.

A total of 22 rats and 64 hamsters have been subjected to experiments in which peptide-containing solutions effectively achieved hemostasis within 10 seconds following application to a site intracranial bleeding.

Example 2

Self-Assembling Peptide Material Accelerates Hemostasis Following Femoral Artery Transection The sciatic nerve and the adjacent femoral artery were exposed in adult rats, and the femoral artery was transected. Twelve rats were treated by application of 20 µl of a 1% solution of RADA 16-I (SEQ ID NO: 1) peptide to the site of transection using a glass pipette attached to a syringe body, while controls were treated by applying cold saline to the site of transection. In all treated cases, hemostasis was achieved in less than 10 seconds. The saline control cases continued to bleed until the experiment was terminated at 110 seconds. In these control animals, subsequent replacement of the cold saline with the peptide solution resulted in almost immediate achievement of complete hemostasis.

A series of pictures was taken in an adult rat in which the femoral artery was transected. In the picture taken first, the sciatic nerve and the femoral artery are exposed. The next picture shows the cutting of the artery, and the next picture shows bleeding. After about five seconds, complete hemostasis was observed in the area of a clear gel formed by the assembled peptides in the presence of blood and plasma. The assembled material can be suctioned off the site easily if desired. Complete hemostasis was maintained for the duration of the test (1 hour).

Complete hemostasis was achieved in less than 10 seconds. In the saline controls, hemostasis was never reached.

Muscle trauma experiments showed immediate hemostasis after 1-2 cm incisions were made in the muscle on the back of a rat. The spinotrapezius muscles on the back of the rats were exposed and a deep cut was made in the muscle, after which 1% peptide solution (RADA16-I) (SEQ ID NO: 1) was applied in the cut. Within 10 seconds, all bleeding had stopped. With the application of iced saline alone, control animals continued to bleed after 20 seconds.

This procedure was duplicated in the muscle of the hind limb (porteocaudalis and musculus tibialis cranialis) and similar results were obtained. Between 1% to 100% peptide (RADA 16-1) (SEQ ID NO: 1) was applied to limb wounds, and hemostasis was achieved in all cases. However when an artery or vein was transected 2% or higher material was needed to bring about hemostasis. With the application of iced saline alone, control animals continued to bleed after 20 seconds.

Example 3

Self-Assembling Peptide Material Accelerates Hemostasis in Liver

To further demonstrate the ability of peptide-containing structures to halt bleeding of a vessel having relatively low pressure, the intraperitoneal cavity of an adult rat was opened, the liver was exposed, and the lobus sinister lateralis received a rostral to caudal cut completely transecting a portion of the liver. Profuse bleeding ensued. A 1% peptide solution (RADA16-1) (SEQ ID NO: 1) was applied to the cut and in its vicinity using a 27 gauge needle and 4 cc syringe. All bleeding stopped within 10 seconds. A series of pictures was obtained. The first shows exposure of the liver; in the second, the liver is separated, and profuse bleeding is evident; and in the third, the two portions of the liver are allowed to come back together, and the bleeding continues. After treating the site with 1% peptide solution (applied topically and in the cut), all bleeding stopped within 10 seconds. A clear area was observed between the two halves of the lobus sinister lateralis. This procedure was repeated several times with the same result.

A similar experiment demonstrated the ability of the peptide structures to halt bleeding of a vessel in the liver having a higher pressure. A series of pictures illustrate the experiment. The first depicts the opened intraperitoneal cavity and exposed liver; in the second, the lobus sinister lateralis received a transverse cut completely transecting a portion of the liver and a major branch of the portal vein; and the third shows profuse bleeding from the site of injury. The cut was treated with 4% peptide solution applied topically and in the cut. All bleeding stopped within 10 seconds. The lower part of the lobus sinister lateralis was pulled downward to show that the peptide structure is in the cut. The site did not bleed even when subjected to this physical stress. Ten minutes later, there was still no bleeding. Thus, application of 4% peptide solution brings about complete hemostasis in a high pressure bleeding environment in less than 10 seconds.

Treatment with a 2% or 3% peptide solution was tested in the same type of experiment and complete hemostasis was also achieved. Treatment with a 1% solution resulted in partial cessation of bleeding. In addition, 30 seconds after treatment the excess peptide structure was wiped away from the injury site and hemostasis was maintained. This procedure was repeated several times with the same result.

In other experiments ¼ of the lobe in the lower right quadrant of the lobus sinistras laterialis was removed, and the margin was treated with a topical application of 2% peptide (RADA16-I) (SEQ ID NO: 1) to the site of injury. Bleeding stopped in less than 10 seconds. One minute later the peptide was removed, and complete hemostasis was achieved at the margin of the liver.

Example 4

Self-Assembling Peptide Material to Prevent Adhesions

The liver of 18 adult rats was exposed under deep anesthesia, the upper right lobe was punched by a 4 mm punch, then the wound was treated with 3% NHS-1. Animals were allowed to survive 2 d, 7 d, 14 d, 6 w, and 8 w respectively, then the animals were anesthetized again and the punched lobe of liver was dissected and processed for H&E staining. In addition a set of controls were treated with either saline or cautery.

4 mm liver punch biopsy experiment with control and filling of punch with 3% RADA. All of the controls had adhesions on both surfaces while the treated had no adhesions. In the 2 week, 6 week and 8 week controls adhesions were cut away on the upper and lower surfaces. On all the 3% RADA treated cases there were no adhesions on with the upper or lower surface of the liver.

Example 5

Self-Assembling Peptide Material

The intestine of an adult rat was perforated with a small cut at the level of the duodenum that resulted in the leakage of gastric fluid into the intraperitoneal cavity. When the site was treated with 2% peptide (RADA16-I) (SEQ ID NO: 1)

solution all leakage of gastric fluids from the intestine stopped. An additional volume of 2% peptide solution was injected into the duodenum at the level of the injury. This prevented all leakage from the intestine for one hour, the duration of the procedure. In the control cut at the level of the duodenum, the wall of the intestine inverted and gastric fluids continued to leak from the site of injury when left untreated. When the site was treated with peptide solution 15 minutes after the injury, the peptide treatment also stopped all leakage from this injury site. In addition, the treatment stopped the progression of the intestinal wall inversion.

Example 6

Self-Assembling Peptide Material Accelerates Healing of Skin Wounds

To demonstrate the ability of the self-assembling peptides to enhance wound healing, animals were subjected to punch biopsies of the skin and subcutaneous tissue. The regions from which the biopsies were taken were either treated by a single application of self-assembling peptide (RADA16-I) (SEQ ID NO: 1) solution or were left untreated. The wounds were left unbandaged. A series of pictures of a 4 mm punch biopsy healing test in which injured animals were treated with the self assembling peptide and compared to matching cases with no treatment illustrates the results. The wounds were photographed on day 0, day 1, day 4, and day 7. The treated wounds healed much faster as evidenced by the contraction of the wound site in all three punches as early as day 1. Treatment with the peptide appeared to speed healing by as much as 5 days in some cases. In all cases, shrinkage of the wound site happened faster in the treated cases.

Example 7

Compositions containing Lidocaine

RADA 16 (SEQ ID NO: 1) mixed with lidocaine and the mixture was applied to the skin of adult rats before applying a pin prick. It is a 5% mix of lidocaine and RADA1-16 (SEQ ID NO: 1). Applied on the skin and left for the duration of the testing. When mixed with a self-assembling peptide, the response to pin prick was muted four times longer than the response was muted using lidocaine alone. In addition, we applied solutions of self-assembling peptides and lidocaine to the intestines of two rats while performing intestinal surgery. The solution reduced peristalsis for the duration of the surgery with no apparent side effects to the animals.

The foregoing description is to be understood as being representative only and is not intended to be limiting. Alternative systems and techniques for making and using the compositions and devices of the invention and for practicing the inventive methods will be apparent to one of skill in the art and are intended to be included within the accompanying claims.

We claim:

1. A method of preventing or limiting formation of scar tissue at a wound or surgery site or a site of inflammation comprising
   topically administering to diseased or damaged skin or epithelial tissue a formulation comprising self-assembling peptides which form a barrier to contamination and loss of fluid from the diseased or damaged skin or epithelial tissue,
   wherein the formulation does not include cells, and
   wherein the barrier is effective to reduce or prevent the formation of scar tissue at the site of administration relative to an untreated control.

2. The method of claim 1, wherein the self-assembling peptides comprise a sequence of amino acid residues conforming to one or more of Formulas I-IV:

$$((Xaa^{neu}\text{-}Xaa^{+})x(Xaa^{neu}\text{-}Xaa^{-})y)n \qquad (I)$$

$$((Xaa^{neu}\text{-}Xaa^{-})x(Xaa^{neu}\text{-}Xaa^{+})y)n \qquad (II)$$

$$((Xaa^{+}\text{-}Xaa^{neu})x(Xaa^{-}\text{-}Xaa^{neu})y)n \qquad (III)$$

$$((Xaa^{-}\text{-}Xaa^{neu})x(Xaa^{+}\text{-}Xaa^{neu})y)n \qquad (IV)$$

wherein: $Xaa^{neu}$ is an amino acid residue having a neutral charge; $Xaa^{+}$ is an amino acid residue having a positive charge; $Xaa_{31}$ is an amino acid residue having a negative charge; x and y are integers having a value of 1, 2 or 4, independently; and n is an integer having a value of 1-5.

3. The method of claim 2, wherein the self-assembling peptides comprise a sequence of amino acid residues conforming to Formula III or Formula IV.

4. The method of claim 3, wherein $Xaa^{neu}$ is alanine, or leucine, or isoleucine; $Xaa^{+}$ is arginine or lysine; and $Xaa^{31}$ is aspartic acid or glutamic acid.

5. The method of claim 2, wherein the self-assembling peptides comprise the amino acid sequence RADARADARADARADA (SEQ ID NO: 1).

6. The method of claim 1, wherein the self-assembling peptides are administered to damaged skin or mucosal tissue that is not bleeding.

7. The method of claim 1, further comprising providing one or more therapeutic, prophylactic, or diagnostic agents.

8. The method of claim 1, wherein the formulation further comprises a pharmaceutically acceptable material for administration to diseased or damaged skin or mucosa.

9. The method of claim 8 wherein the formulation is in a form selected from the group consisting of a dry powder, wafer, disk, tablet, capsule, liquid, gel, cream, foam, ointment, emulsion, suspension, solution, a coating on a medical device, microparticles, polymeric matrices, hydrogels, textile, suture, and a sponge.

10. The method of claim 9, wherein the self-assembling peptides are applied in the form of a solution.

11. The method of claim 10, further comprising the step of forming the solution by dissolving a powder of the self-assembling peptides with water or oil.

12. The method of claim 11, wherein the concentration of self-assembling peptides in the solution is between 2% wt/vol and 3% wt/vol, inclusive.

13. The method of claim 1, wherein the self-assembling peptides are administered to the site of a surgical procedure at a time point selected from group consisting of before the initiation of the surgical procedure; during the surgical procedure; after commencement of the surgical procedure; and combinations thereof.

14. The method of claim 1, wherein the self-assembling peptides are administered to the surface of skin at the site of a burn.

15. The method of claim 1, wherein the self-assembling peptides are administered to the surface of skin at the site of a laceration.

16. The method of claim 1, wherein the self-assembling peptides are administered to the surface of skin at the site of an ulcer.

17. The method of claim 1, wherein the formulation of self-assembling peptides comprises a concentration of Li+, Na+, K+, and Cs+ ions less than 5 mM.

18. The method of claim 1, wherein the self-assembling peptides are in a solution having a concentration of self-assembling peptides between 1.0% and 10.0%, inclusive.

19. The method of claim 1, wherein the self-assembling peptides are administered to damaged skin or mucosal tissue that is bleeding, and
wherein the self-assembled barrier structure is maintained in contact with the tissue following the cessation of bleeding.

* * * * *

SEQUENCE LISTING

```
<160> NUMBER OF SEQ ID NOS: 342

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Glu Ala Lys Ala
1

<210> SEQ ID NO 3
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 3

Ser Gly Ser Gly Ser Gly Ser Gly Ser Gly Ser Gly Ser Gly Ser Gly
1               5                   10                  15

<210> SEQ ID NO 4
```

```
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 4

Ser Ala Ser Ala Ser Ala Ser Ala Ser Ala Ser Ala Ser Ala Ser Ala
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic self assemling peptide

<400> SEQUENCE: 5

Ser Val Ser Val Ser Val Ser Val Ser Val Ser Val Ser Val Ser Val
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 6

Ser Leu Ser Leu Ser Leu Ser Leu Ser Leu Ser Leu Ser Leu Ser Leu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 7

Ser Ile Ser Ile Ser Ile Ser Ile Ser Ile Ser Ile Ser Ile Ser Ile
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 8

Ser Met Ser Met Ser Met Ser Met Ser Met Ser Met Ser Met Ser Met
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 9

Ser Phe Ser Phe Ser Phe Ser Phe Ser Phe Ser Phe Ser Phe Ser Phe
1               5                   10                  15

<210> SEQ ID NO 10
<211> LENGTH: 16
```

-continued

```
<212> TYPE: PRT
<213> ORGANISM: Artificial Sequence
<220> FEATURE:
<223> OTHER INFORMATION: Synthetic self-assembling peptide

<400> SEQUENCE: 10

Ser Trp Ser Trp Ser Trp Ser Trp Ser Trp Ser Trp Ser Trp Ser Trp
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 11

Ser Pro Ser Pro Ser Pro Ser Pro Ser Pro Ser Pro Ser Pro Ser Pro
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 12

Thr Gly Thr Gly Thr Gly Thr Gly Thr Gly Thr Gly Thr Gly Thr Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 13

Thr Ala Thr Ala Thr Ala Thr Ala Thr Ala Thr Ala Thr Ala Thr Ala
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 14

Thr Val Thr Val Thr Val Thr Val Thr Val Thr Val Thr Val Thr Val
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic self-assembling peptide

<400> SEQUENCE: 15

Thr Leu Thr Leu Thr Leu Thr Leu Thr Leu Thr Leu Thr Leu Thr
1               5                   10                  15

<210> SEQ ID NO 16
<211> LENGTH: 16
<212> TYPE: PRT
```

```
<213> ORGANISM: Artificial Sequence
<220> FEATURE:
<223> OTHER INFORMATION: Synthetic self-assembling peptide

<400> SEQUENCE: 16

Thr Ile Thr Ile Thr Ile Thr Ile Thr Ile Thr Ile Thr Ile Thr Ile
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 17

Thr Met Thr Met Thr Met Thr Met Thr Met Thr Met Thr Met Thr Met
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 18

Thr Phe Thr Phe Thr Phe Thr Phe Thr Phe Thr Phe Thr Phe Thr Phe
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 19

Thr Trp Thr Trp Thr Trp Thr Trp Thr Trp Thr Trp Thr Trp Thr Trp
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 20

Thr Pro Thr Pro Thr Pro Thr Pro Thr Pro Thr Pro Thr Pro Thr Pro
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 21

Cys Gly Cys Gly Cys Gly Cys Gly Cys Gly Cys Gly Cys Gly Cys Gly
1               5                   10                  15

<210> SEQ ID NO 22
<211> LENGTH: 16
<212> TYPE: PRT
<213> ORGANISM: Artificial Sequence
```

```
<220> FEATURE:
<223> OTHER INFORMATION: Synthetic self-assembling peptide

<400> SEQUENCE: 22

Cys Ala Cys Ala Cys Ala Cys Ala Cys Ala Cys Ala Cys Ala Cys Ala
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 23

Cys Val Cys Val Cys Val Cys Val Cys Val Cys Val Cys Val Cys Val
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 24

Cys Leu Cys Leu Cys Leu Cys Leu Cys Leu Cys Leu Cys Leu Cys Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 25

Cys Ile Cys Ile Cys Ile Cys Ile Cys Ile Cys Ile Cys Ile Cys Ile
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 26

Cys Met Cys Met Cys Met Cys Met Cys Met Cys Met Cys Met Cys Met
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 27

Cys Phe Cys Phe Cys Phe Cys Phe Cys Phe Cys Phe Cys Phe Cys Phe
1               5                   10                  15

<210> SEQ ID NO 28
<211> LENGTH: 15
<212> TYPE: PRT
<213> ORGANISM: Artificial Sequence
<220> FEATURE:
```

<223> OTHER INFORMATION: Synthetic self-assembling peptide

<400> SEQUENCE: 28

Cys Trp Cys Trp Cys Trp Cys Trp Cys Trp Cys Trp Cys Trp Cys
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 29

Cys Pro Cys Pro Cys Pro Cys Pro Cys Pro Cys Pro Cys Pro Cys Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 30

Tyr Gly Tyr Gly Tyr Gly Tyr Gly Tyr Gly Tyr Gly Tyr Gly Tyr Gly
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 31

Tyr Ala Tyr Ala Tyr Ala Tyr Ala Tyr Ala Tyr Ala Tyr Ala Tyr Ala
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 32

Tyr Val Tyr Val Tyr Val Tyr Val Tyr Val Tyr Val Tyr Val Tyr Val
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 33

Tyr Leu Tyr Leu Tyr Leu Tyr Leu Tyr Leu Tyr Leu Tyr Leu Tyr Leu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 34

Tyr Ile Tyr Ile Tyr Ile Tyr Ile Tyr Ile Tyr Ile Tyr Ile Tyr Ile
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 35

Tyr Met Tyr Met Tyr Met Tyr Met Tyr Met Tyr Met Tyr Met Tyr Met
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 36

Tyr Phe Tyr Phe Tyr Phe Tyr Phe Tyr Phe Tyr Phe Tyr Phe Tyr Phe
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 37

Tyr Trp Tyr Trp Tyr Trp Tyr Trp Tyr Trp Tyr Trp Tyr Trp Tyr Trp
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 38

Tyr Pro Tyr Pro Tyr Pro Tyr Pro Tyr Pro Tyr Pro Tyr Pro Tyr Pro
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 39

Asn Gly Asn Gly Asn Gly Asn Gly Asn Gly Asn Gly Asn Gly Asn Gly
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic self-assembling peptide

```
<400> SEQUENCE: 40

Asn Ala Asn Ala Asn Ala Asn Ala Asn Ala Asn Ala Asn Ala Asn Ala
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 41

Asn Val Asn Val Asn Val Asn Val Asn Val Asn Val Asn Val Asn Val
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 42

Asn Leu Asn Leu Asn Leu Asn Leu Asn Leu Asn Leu Asn Leu Asn Leu
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 43

Asn Ile Asn Ile Asn Ile Asn Ile Asn Ile Asn Ile Asn Ile Asn Ile
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 44

Asn Met Asn Met Asn Met Asn Met Asn Met Asn Met Asn Met Asn Met
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 45

Asn Phe Asn Phe Asn Phe Asn Phe Asn Phe Asn Phe Asn Phe Asn Phe
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 46
```

```
Asn Trp Asn Trp Asn Trp Asn Trp Asn Trp Asn Trp Asn Trp Asn Trp
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 47

Asn Pro Asn Pro Asn Pro Asn Pro Asn Pro Asn Pro Asn Pro Asn Pro
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 48

Gln Gly Gln Gly Gln Gly Gln Gly Gln Gly Gln Gly Gln Gly Gln Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 49

Gln Ala Gln Ala Gln Ala Gln Ala Gln Ala Gln Ala Gln Ala Gln Ala
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 50

Gln Val Gln Val Gln Val Gln Val Gln Val Gln Val Gln Val Gln Val
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 51

Gln Leu Gln Leu Gln Leu Gln Leu Gln Leu Gln Leu Gln Leu Gln Leu
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 52
```

```
Gln Ile Gln Ile Gln Ile Gln Ile Gln Ile Gln Ile Gln Ile Gln Ile
1               5                   10                  15
```

<210> SEQ ID NO 53
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 53

```
Gln Met Gln Met Gln Met Gln Met Gln Met Gln Met Gln Met Gln Met
1               5                   10                  15
```

<210> SEQ ID NO 54
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 54

```
Gln Phe Gln Phe Gln Phe Gln Phe Gln Phe Gln Phe Gln Phe Gln Phe
1               5                   10                  15
```

<210> SEQ ID NO 55
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 55

```
Gln Trp Gln Trp Gln Trp Gln Trp Gln Trp Gln Trp Gln Trp Gln Trp
1               5                   10                  15
```

<210> SEQ ID NO 56
<211> LENGTH: 16
<212> TYPE: PRT
<213> ORGANISM: Artificial Sequence
<220> FEATURE:
<223> OTHER INFORMATION: Synthetic self-assembling peptide

<400> SEQUENCE: 56

```
Gln Pro Gln Pro Gln Pro Gln Pro Gln Pro Gln Pro Gln Pro Gln Pro
1               5                   10                  15
```

<210> SEQ ID NO 57
<211> LENGTH: 12
<212> TYPE: PRT
<213> ORGANISM: Artificial Sequence
<220> FEATURE:
<223> OTHER INFORMATION: Synthetic self-assembling peptide

<400> SEQUENCE: 57

```
Arg Ala Arg Ala Arg Ala Asp Ala Asp Ala Asp Ala
1               5                   10
```

<210> SEQ ID NO 58
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 58

```
Gly Gly Gly Gly Gly Asp Gly Asp Gly Asp Gly Asp Gly Asp Gly Asp
```

```
<210> SEQ ID NO 59
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 59

Gly Gly Gly Gly Gly Glu Gly Glu Gly Glu Gly Glu Gly Glu Gly Glu
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 60

Gly Gly Gly Gly Gly Lys Gly Lys Gly Lys Gly Lys Gly Lys Gly Lys
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 61

Gly Gly Gly Gly Gly Arg Gly Arg Gly Arg Gly Arg Gly Arg Gly Arg
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 62

Gly Gly Gly Gly Gly His Gly His Gly His Gly His Gly His Gly His
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 63

Ala Ala Ala Ala Ala Asp Ala Asp Ala Asp Ala Asp Ala Asp Ala Asp
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 64

Ala Ala Ala Ala Ala Glu Ala Glu Ala Glu Ala Glu Ala Glu Ala Glu
1               5                   10                  15
```

```
<210> SEQ ID NO 65
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 65

Ala Ala Ala Ala Ala Lys Ala Lys Ala Lys Ala Lys Ala Lys Ala Lys
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 66

Ala Ala Ala Ala Ala Arg Ala Arg Ala Arg Ala Arg Ala Arg Ala Arg
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 67

Ala Ala Ala Ala Ala His Ala His Ala His Ala His Ala His Ala His
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 68

Val Val Val Val Val Asp Val Asp Val Asp Val Asp Val Asp Val Asp
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 69

Val Val Val Val Val Glu Val Glu Val Glu Val Glu Val Glu Val Glu
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 70

Val Val Val Val Val Lys Val Lys Val Lys Val Lys Val Lys Val Lys
1               5                   10                  15
```

<210> SEQ ID NO 71
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 71

Val Val Val Val Val Arg Val Arg Val Arg Val Arg Val Arg Val Arg
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 72

Val Val Val Val Val His Val His Val His Val His Val His Val His
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 73

Leu Leu Leu Leu Leu Asp Leu Asp Leu Asp Leu Asp Leu Asp Leu Asp
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 74

Leu Leu Leu Leu Leu Glu Leu Glu Leu Glu Leu Glu Leu Glu Leu Glu
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 75

Leu Leu Leu Leu Leu Lys Leu Lys Leu Lys Leu Lys Leu Lys Leu Lys
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 76

Leu Leu Leu Leu Leu Arg Leu Arg Leu Arg Leu Arg Leu Arg Leu Arg
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 77

```
Leu Leu Leu Leu Leu His Leu His Leu His Leu His Leu His Leu His
1               5                   10                  15
```

<210> SEQ ID NO 78
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 78

```
Ile Ile Ile Ile Ile Asp Ile Asp Ile Asp Ile Asp Ile Asp Ile Asp
1               5                   10                  15
```

<210> SEQ ID NO 79
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 79

```
Ile Ile Ile Ile Ile Glu Ile Glu Ile Glu Ile Glu Ile Glu Ile Glu
1               5                   10                  15
```

<210> SEQ ID NO 80
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 80

```
Ile Ile Ile Ile Ile Lys Ile Lys Ile Lys Ile Lys Ile Lys Ile Lys
1               5                   10                  15
```

<210> SEQ ID NO 81
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 81

```
Ile Ile Ile Ile Ile Arg Ile Arg Ile Arg Ile Arg Ile Arg Ile Arg
1               5                   10                  15
```

<210> SEQ ID NO 82
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 82

```
Ile Ile Ile Ile Ile His Ile His Ile His Ile His Ile His Ile His
1               5                   10                  15
```

<210> SEQ ID NO 83

<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 83

Met Met Met Met Met Asp Met Asp Met Asp Met Asp Met Asp Met Asp
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 84

Met Met Met Met Met Glu Met Glu Met Glu Met Glu Met Glu Met Glu
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 85

Met Met Met Met Met Lys Met Lys Met Lys Met Lys Met Lys Met Lys
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 86

Met Met Met Met Met Arg Met Arg Met Arg Met Arg Met Arg Met Arg
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 87

Met Met Met Met Met His Met His Met His Met His Met His Met His
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 88

Phe Phe Phe Phe Phe Asp Phe Asp Phe Asp Phe Asp Phe Asp Phe Asp
1               5                   10                  15

<210> SEQ ID NO 89
<211> LENGTH: 16

```
<212> TYPE: PRT
<213> ORGANISM: Artificial Sequence
<220> FEATURE:
<223> OTHER INFORMATION: Synthetic peptide with hydrophobic tail

<400> SEQUENCE: 89

Phe Phe Phe Phe Phe Glu Phe Glu Phe Glu Phe Glu Phe Glu Phe Glu
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 90

Phe Phe Phe Phe Phe Lys Phe Lys Phe Lys Phe Lys Phe Lys Phe Lys
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 91

Phe Phe Phe Phe Phe Arg Phe Arg Phe Arg Phe Arg Phe Arg Phe Arg
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 92

Phe Phe Phe Phe Phe His Phe His Phe His Phe His Phe His Phe His
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 93

Trp Trp Trp Trp Trp Asp Trp Asp Trp Asp Trp Asp Trp Asp Trp Asp
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 94

Trp Trp Trp Trp Trp Glu Trp Glu Trp Glu Trp Glu Trp Glu Trp Glu
1               5                   10                  15

<210> SEQ ID NO 95
<211> LENGTH: 16
<212> TYPE: PRT
```

<213> ORGANISM: Artificial Sequence
<220> FEATURE:
<223> OTHER INFORMATION: Synthetic peptide with hydrophobic tail

<400> SEQUENCE: 95

Trp Trp Trp Trp Trp Lys Trp Lys Trp Lys Trp Lys Trp Lys Trp Lys
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 96

Trp Trp Trp Trp Trp Arg Trp Arg Trp Arg Trp Arg Trp Arg Trp Arg
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 97

Trp Trp Trp Trp Trp His Trp His Trp His Trp His Trp His Trp His
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 98

Pro Pro Pro Pro Pro Asp Pro Asp Pro Asp Pro Asp Pro Asp Pro Asp
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 99

Pro Pro Pro Pro Pro Glu Pro Glu Pro Glu Pro Glu Pro Glu Pro Glu
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 100

Pro Pro Pro Pro Pro Lys Pro Lys Pro Lys Pro Lys Pro Lys Pro Lys
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 101

Pro Pro Pro Pro Pro Arg Pro Arg Pro Arg Pro Arg Pro Arg Pro Arg
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 102

Pro Pro Pro Pro Pro His Pro His Pro His Pro His Pro His Pro His
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 103

Ala Ala Ala Ala Ala Arg Ala Asp Ala Arg Ala Asp Ala Arg Ala Asp
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 104

Ala Ala Ala Ala Ala Arg Ala Arg Ala Asp Ala Asp Ala Arg Ala Arg
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 105

Ala Ala Ala Ala Ala Glu Ala Lys Ala Glu Ala Lys Ala Glu Ala Lys
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 106

Ala Ala Ala Ala Ala Glu Ala Glu Ala Lys Ala Lys Ala Glu Ala Glu
1               5                   10                  15

<210> SEQ ID NO 107
<211> LENGTH: 16
<212> TYPE: PRT
<213> ORGANISM: Artificial Sequence
<220> FEATURE:

```
<223> OTHER INFORMATION: Synthetic peptide with hydrophobic tail

<400> SEQUENCE: 107

Ala Ala Ala Ala Ala Arg Ala Glu Ala Arg Ala Glu Ala Arg Ala Glu
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 108

Ala Ala Ala Ala Ala Arg Ala Arg Ala Glu Ala Glu Ala Arg Ala Glu
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 109

Ala Ala Ala Ala Ala Lys Ala Asp Ala Lys Ala Asp Ala Lys Ala Asp
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 110

Ala Ala Ala Ala Ala Glu Ala His Ala Glu Ala His Ala Glu Ala His
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 111

Ala Ala Ala Ala Ala Glu Ala Glu Ala His Ala His Ala Glu Ala Glu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 112

Ala Ala Ala Ala Ala Arg Ala Arg Ala Arg Ala Arg Ala Arg Ala Arg
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic peptide with hydrophobic tail
```

<400> SEQUENCE: 113

Ala Ala Ala Ala Ala Arg Ala Arg Ala Arg Ala Arg Ala Asp Ala Asp
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 114

Ala Ala Ala Ala Ala Arg Ala Arg Ala Arg Ala Asp Ala Asp Ala Asp
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 115

Ala Ala Ala Ala Ala His Ala Asp Ala His Ala Asp Ala His Ala Asp
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 116

Ala Ala Ala Ala Ala His Ala His Ala His Ala His Ala His Ala His
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 117

Ala Ala Ala Ala Ala His Ala Asp Ala Asp Ala His Ala Asp Ala Asp
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 118

Ala Ala Ala Ala Ala His Ala Glu Ala Glu Ala His Ala Glu Ala Glu
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic peptide with hydrophobic tail -continued

<400> SEQUENCE: 119

Gly Gly Gly Gly Gly Arg Gly Asp Gly Arg Gly Asp Gly Arg Gly Asp
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 120

Gly Gly Gly Gly Gly Arg Gly Arg Gly Asp Gly Asp Gly Arg Gly Arg
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 121

Gly Gly Gly Gly Gly Glu Gly Lys Gly Glu Gly Lys Gly Glu Gly Lys
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 122

Gly Gly Gly Gly Gly Glu Gly Glu Gly Lys Gly Lys Gly Glu Gly Glu
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 123

Gly Gly Gly Gly Gly Arg Gly Glu Gly Arg Gly Glu Gly Arg Gly Glu
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 124

Gly Gly Gly Gly Gly Arg Gly Arg Gly Glu Gly Glu Gly Arg Gly Glu
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 125

```
Gly Gly Gly Gly Gly Lys Gly Asp Gly Lys Gly Asp Gly Lys Gly Asp
1               5                   10                  15
```

<210> SEQ ID NO 126
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 126

```
Gly Gly Gly Gly Gly Glu Gly His Gly Glu Gly His Gly Glu Gly His
1               5                   10                  15
```

<210> SEQ ID NO 127
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 127

```
Gly Gly Gly Gly Gly Glu Gly Glu Gly His Gly His Gly Glu Gly Glu
1               5                   10                  15
```

<210> SEQ ID NO 128
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 128

```
Gly Gly Gly Gly Gly Arg Gly Arg Gly Arg Gly Arg Gly Arg Gly Arg
1               5                   10                  15
```

<210> SEQ ID NO 129
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 129

```
Gly Gly Gly Gly Gly Arg Gly Arg Gly Arg Gly Arg Gly Asp Gly Asp
1               5                   10                  15
```

<210> SEQ ID NO 130
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 130

```
Gly Gly Gly Gly Gly Arg Gly Arg Gly Arg Gly Asp Gly Asp Gly Asp
1               5                   10                  15
```

<210> SEQ ID NO 131
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 131

```
Gly Gly Gly Gly Gly His Gly Asp Gly His Gly Asp Gly His Gly Asp
1               5                   10                  15
```

<210> SEQ ID NO 132
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 132

```
Gly Gly Gly Gly Gly His Gly His Gly His Gly His Gly His Gly His
1               5                   10                  15
```

<210> SEQ ID NO 133
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 133

```
Gly Gly Gly Gly Gly His Gly Asp Gly Asp Gly His Gly Asp Gly Asp
1               5                   10                  15
```

<210> SEQ ID NO 134
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 134

```
Gly Gly Gly Gly Gly His Gly Glu Gly Glu Gly His Gly Glu Gly Glu
1               5                   10                  15
```

<210> SEQ ID NO 135
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 135

```
Val Val Val Val Val Arg Val Asp Val Arg Val Asp Val Arg Val Asp
1               5                   10                  15
```

<210> SEQ ID NO 136
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 136

```
Val Val Val Val Val Arg Val Arg Val Asp Val Asp Val Arg Val Arg
1               5                   10                  15
```

<210> SEQ ID NO 137
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 137

```
Val Val Val Val Val Glu Val Lys Val Glu Val Lys Val Glu Val Lys
```

```
1               5                   10                  15
```

<210> SEQ ID NO 138
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 138

```
Val Val Val Val Val Glu Val Glu Val Lys Val Lys Val Glu Val Glu
1               5                   10                  15
```

<210> SEQ ID NO 139
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 139

```
Val Val Val Val Val Arg Val Glu Val Arg Val Glu Val Arg Val Glu
1               5                   10                  15
```

<210> SEQ ID NO 140
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 140

```
Val Val Val Val Val Arg Val Arg Val Glu Val Glu Val Arg Val Glu
1               5                   10                  15
```

<210> SEQ ID NO 141
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 141

```
Val Val Val Val Val Lys Val Asp Val Lys Val Asp Val Lys Val Asp
1               5                   10                  15
```

<210> SEQ ID NO 142
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 142

```
Val Val Val Val Val Glu Val His Val Glu Val His Val Glu Val His
1               5                   10                  15
```

<210> SEQ ID NO 143
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 143

```
Val Val Val Val Val Glu Val Glu Val His Val His Val Glu Val Glu
1               5                   10                  15
```

<210> SEQ ID NO 144
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 144

Val Val Val Val Val Arg Val Arg Val Arg Val Arg Val Arg Val Arg
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 145

Val Val Val Val Val Arg Val Arg Val Arg Val Arg Val Asp Val Asp
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 146

Val Val Val Val Val Arg Val Arg Val Arg Val Asp Val Asp Val Asp
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 147

Val Val Val Val Val His Val Asp Val His Val Asp Val His Val Asp
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 148

Val Val Val Val Val His Val His Val His Val His Val His Val His
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 149

Val Val Val Val Val His Val Asp Val Asp Val His Val Asp Val Asp
1               5                   10                  15

```
<210> SEQ ID NO 150
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 150

Val Val Val Val His Val Glu Val Glu Val His Val Glu Val Glu
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 151

Leu Leu Leu Leu Leu Arg Leu Asp Leu Arg Leu Asp Leu Arg Leu Asp
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 152

Leu Leu Leu Leu Leu Arg Leu Arg Leu Asp Leu Asp Leu Arg Leu Arg
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 153

Leu Leu Leu Leu Leu Glu Leu Lys Leu Glu Leu Lys Leu Glu Leu Lys
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 154

Leu Leu Leu Leu Leu Glu Leu Glu Leu Lys Leu Lys Leu Glu Leu Glu
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 155

Leu Leu Leu Leu Leu Arg Leu Glu Leu Arg Leu Glu Leu Arg Leu Glu
1               5                   10                  15
```

```
<210> SEQ ID NO 156
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 156

Leu Leu Leu Leu Leu Arg Leu Arg Leu Glu Leu Glu Leu Arg Leu Glu
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 157

Leu Leu Leu Leu Leu Lys Leu Asp Leu Lys Leu Asp Leu Lys Leu Asp
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 158

Leu Leu Leu Leu Leu Glu Leu His Leu Glu Leu His Leu Glu Leu His
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 159

Leu Leu Leu Leu Leu Glu Leu Glu Leu His Leu His Leu Glu Leu Glu
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 160

Leu Leu Leu Leu Leu Arg Leu Arg Leu Arg Leu Arg Leu Arg Leu Arg
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 161

Leu Leu Leu Leu Leu Arg Leu Arg Leu Arg Leu Arg Leu Asp Leu Asp
1               5                   10                  15

<210> SEQ ID NO 162
```

```
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 162

Leu Leu Leu Leu Leu Arg Leu Arg Leu Arg Leu Asp Leu Asp Leu Asp
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 163

Leu Leu Leu Leu Leu His Leu Asp Leu His Leu Asp Leu His Leu Asp
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 164

Leu Leu Leu Leu Leu His Leu His Leu His Leu His Leu His Leu His
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 165

Leu Leu Leu Leu Leu His Leu Asp Leu Asp Leu His Leu Asp Leu Asp
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 166

Leu Leu Leu Leu Leu His Leu Glu Leu Glu Leu His Leu Glu Leu Glu
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 167

Ile Ile Ile Ile Ile Arg Ile Asp Ile Arg Ile Asp Ile Arg Ile Asp
1               5                   10                  15

<210> SEQ ID NO 168
<211> LENGTH: 16
```

```
<212> TYPE: PRT
<213> ORGANISM: Artificial Sequence
<220> FEATURE:
<223> OTHER INFORMATION: Synthetic peptide with hydrophobic tail

<400> SEQUENCE: 168

Ile Ile Ile Ile Ile Arg Ile Arg Ile Asp Ile Asp Ile Arg Ile Arg
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 169

Ile Ile Ile Ile Ile Glu Ile Lys Ile Glu Ile Lys Ile Glu Ile Lys
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 170

Ile Ile Ile Ile Ile Glu Ile Glu Ile Lys Ile Lys Ile Glu Ile Glu
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 171

Ile Ile Ile Ile Ile Arg Ile Glu Ile Arg Ile Glu Ile Arg Ile Glu
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 172

Ile Ile Ile Ile Ile Arg Ile Arg Ile Glu Ile Glu Ile Arg Ile Glu
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 173

Ile Ile Ile Ile Ile Lys Ile Asp Ile Lys Ile Asp Ile Lys Ile Asp
1               5                   10                  15

<210> SEQ ID NO 174
<211> LENGTH: 16
<212> TYPE: PRT
```

```
<213> ORGANISM: Artificial Sequence
<220> FEATURE:
<223> OTHER INFORMATION: Synthetic peptide with hydrophobic tail

<400> SEQUENCE: 174

Ile Ile Ile Ile Ile Glu Ile His Ile Glu Ile His Ile Glu Ile His
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 175

Ile Ile Ile Ile Ile Glu Ile Glu Ile His Ile His Ile Glu Ile Glu
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 176

Ile Ile Ile Ile Ile Arg Ile Arg Ile Arg Ile Arg Ile Arg Ile Arg
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 177

Ile Ile Ile Ile Ile Arg Ile Arg Ile Arg Ile Arg Ile Asp Ile Asp
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 178

Ile Ile Ile Ile Ile Arg Ile Arg Ile Arg Ile Asp Ile Asp Ile Asp
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 179

Ile Ile Ile Ile Ile His Ile Asp Ile His Ile Asp Ile His Ile Asp
1               5                   10                  15

<210> SEQ ID NO 180
<211> LENGTH: 16
<212> TYPE: PRT
<213> ORGANISM: Artificial Sequence
```

<220> FEATURE:
<223> OTHER INFORMATION: Synthetic peptide with hydrophobic tail

<400> SEQUENCE: 180

Ile Ile Ile Ile Ile His Ile His Ile His Ile His Ile His Ile His
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 181

Ile Ile Ile Ile Ile His Ile Asp Ile Asp Ile His Ile Asp Ile Asp
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 182

Ile Ile Ile Ile Ile His Ile Glu Ile Glu Ile His Ile Glu Ile Glu
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 183

Met Met Met Met Met Arg Met Asp Met Arg Met Asp Met Arg Met Asp
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 184

Met Met Met Met Met Arg Met Arg Met Asp Met Asp Met Arg Met Arg
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 185

Met Met Met Met Met Glu Met Lys Met Glu Met Lys Met Glu Met Lys
1               5                   10                  15

<210> SEQ ID NO 186
<211> LENGTH: 16
<212> TYPE: PRT
<213> ORGANISM: Artificial Sequence
<220> FEATURE:

<223> OTHER INFORMATION: Synthetic peptide with hydrophobic tail

<400> SEQUENCE: 186

Met Met Met Met Met Glu Met Glu Met Lys Met Lys Met Glu Met Glu
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 187

Met Met Met Met Met Arg Met Glu Met Arg Met Glu Met Arg Met Glu
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 188

Met Met Met Met Met Arg Met Arg Met Glu Met Glu Met Arg Met Glu
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 189

Met Met Met Met Met Lys Met Asp Met Lys Met Asp Met Lys Met Asp
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 190

Met Met Met Met Met Glu Met His Met Glu Met His Met Glu Met His
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 191

Met Met Met Met Met Glu Met Glu Met His Met His Met Glu Met Glu
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 192

Met Met Met Met Met Arg Met Arg Met Arg Met Arg Met Arg
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 193

Met Met Met Met Met Arg Met Arg Met Arg Met Arg Met Asp Met Asp
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 194

Met Met Met Met Met Arg Met Arg Met Arg Met Asp Met Asp Met Asp
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 195

Met Met Met Met Met His Met Asp Met His Met Asp Met His Met Asp
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 196

Met Met Met Met Met His Met His Met His Met His Met His Met His
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 197

Met Met Met Met Met His Met Asp Met Asp Met His Met Asp Met Asp
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 198

Met Met Met Met Met His Met Glu Met Glu Met His Met Glu Met Glu
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 199

Phe Phe Phe Phe Phe Arg Phe Asp Phe Arg Phe Asp Phe Arg Phe Asp
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 200

Phe Phe Phe Phe Phe Arg Phe Arg Phe Asp Phe Asp Phe Arg Phe Arg
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 201

Phe Phe Phe Phe Phe Glu Phe Lys Phe Glu Phe Lys Phe Glu Phe Lys
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 202

Phe Phe Phe Phe Phe Glu Phe Glu Phe Lys Phe Lys Phe Glu Phe Glu
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 203

Phe Phe Phe Phe Phe Arg Phe Glu Phe Arg Phe Glu Phe Arg Phe Glu
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 204

```
Phe Phe Phe Phe Phe Arg Phe Arg Phe Glu Phe Glu Phe Arg Phe Glu
1               5                   10                  15
```

<210> SEQ ID NO 205
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 205

```
Phe Phe Phe Phe Phe Lys Phe Asp Phe Lys Phe Asp Phe Lys Phe Asp
1               5                   10                  15
```

<210> SEQ ID NO 206
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 206

```
Phe Phe Phe Phe Phe Glu Phe His Phe Glu Phe His Phe Glu Phe His
1               5                   10                  15
```

<210> SEQ ID NO 207
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 207

```
Phe Phe Phe Phe Phe Glu Phe Glu Phe His Phe His Phe Glu Phe Glu
1               5                   10                  15
```

<210> SEQ ID NO 208
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 208

```
Phe Phe Phe Phe Phe Arg Phe Arg Phe Arg Phe Arg Phe Arg Phe Arg
1               5                   10                  15
```

<210> SEQ ID NO 209
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 209

```
Phe Phe Phe Phe Phe Arg Phe Arg Phe Arg Phe Arg Phe Asp Phe Asp
1               5                   10                  15
```

<210> SEQ ID NO 210
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 210

Phe Phe Phe Phe Phe Arg Phe Arg Phe Arg Phe Asp Phe Asp Phe Asp
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 211

Phe Phe Phe Phe Phe His Phe Asp Phe His Phe Asp Phe His Phe Asp
1               5                   10                  15

<210> SEQ ID NO 212
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 212

Phe Phe Phe Phe Phe His Phe His Phe His Phe His Phe His Phe His
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 213

Phe Phe Phe Phe Phe His Phe Asp Phe Asp Phe His Phe Asp Phe Asp
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 214

Phe Phe Phe Phe Phe His Phe Glu Phe Glu Phe His Phe Glu Phe Glu
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 215

Trp Trp Trp Trp Trp Arg Trp Asp Trp Arg Trp Asp Trp Arg Trp Asp
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 216

Trp Trp Trp Trp Trp Arg Trp Arg Trp Asp Trp Asp Trp Arg Trp Arg

```
1               5                  10                  15
```

<210> SEQ ID NO 217
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 217

```
Trp Trp Trp Trp Trp Glu Trp Lys Trp Glu Trp Lys Trp Glu Trp Lys
1               5                  10                  15
```

<210> SEQ ID NO 218
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 218

```
Trp Trp Trp Trp Trp Glu Trp Glu Trp Lys Trp Lys Trp Glu Trp Glu
1               5                  10                  15
```

<210> SEQ ID NO 219
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 219

```
Trp Trp Trp Trp Trp Arg Trp Glu Trp Arg Trp Glu Trp Arg Trp Glu
1               5                  10                  15
```

<210> SEQ ID NO 220
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 220

```
Trp Trp Trp Trp Trp Arg Trp Arg Trp Glu Trp Glu Trp Arg Trp Glu
1               5                  10                  15
```

<210> SEQ ID NO 221
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 221

```
Trp Trp Trp Trp Trp Lys Trp Asp Trp Lys Trp Asp Trp Lys Trp Asp
1               5                  10                  15
```

<210> SEQ ID NO 222
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 222

```
Trp Trp Trp Trp Trp Glu Trp His Trp Glu Trp His Trp Glu Trp His
1               5                  10                  15
```

<210> SEQ ID NO 223
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 223

Trp Trp Trp Trp Trp Glu Trp Glu Trp His Trp His Trp Glu Trp Glu
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 224

Trp Trp Trp Trp Trp Arg Trp Arg Trp Arg Trp Arg Trp Arg Trp Arg
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 225

Trp Trp Trp Trp Trp Arg Trp Arg Trp Arg Trp Arg Trp Asp Trp Asp
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 226

Trp Trp Trp Trp Trp Arg Trp Arg Trp Arg Trp Asp Trp Asp Trp Asp
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 227

Trp Trp Trp Trp Trp His Trp Asp Trp His Trp Asp Trp His Trp Asp
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 228

Trp Trp Trp Trp Trp His Trp His Trp His Trp His Trp His Trp His
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 229

Trp Trp Trp Trp Trp His Trp Asp Trp Asp Trp His Trp Asp Trp Asp
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 230

Trp Trp Trp Trp Trp His Trp Glu Trp Glu Trp His Trp Glu Trp Glu
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 231

Pro Pro Pro Pro Pro Arg Pro Asp Pro Arg Pro Asp Pro Arg Pro Asp
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 232

Pro Pro Pro Pro Pro Arg Pro Arg Pro Asp Pro Asp Pro Arg Pro Arg
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 233

Pro Pro Pro Pro Pro Glu Pro Lys Pro Glu Pro Lys Pro Glu Pro Lys
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 234

Pro Pro Pro Pro Pro Glu Pro Glu Pro Lys Pro Lys Pro Glu Pro Glu
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 235

Pro Pro Pro Pro Pro Arg Pro Glu Pro Arg Pro Glu Pro Arg Pro Glu
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 236

Pro Pro Pro Pro Pro Arg Pro Arg Pro Glu Pro Glu Pro Arg Pro Glu
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 237

Pro Pro Pro Pro Pro Lys Pro Asp Pro Lys Pro Asp Pro Lys Pro Asp
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 238

Pro Pro Pro Pro Pro Glu Pro His Pro Glu Pro His Pro Glu Pro His
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 239

Pro Pro Pro Pro Pro Glu Pro Glu Pro His Pro His Pro Glu Pro Glu
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 240

Pro Pro Pro Pro Pro Arg Pro Arg Pro Arg Pro Arg Pro Arg Pro Arg
1               5                   10                  15

<210> SEQ ID NO 241

```
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 241

Pro Pro Pro Pro Pro Arg Pro Arg Pro Arg Pro Arg Pro Asp Pro Asp
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 242

Pro Pro Pro Pro Pro Arg Pro Arg Pro Arg Pro Asp Pro Asp Pro Asp
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 243

Pro Pro Pro Pro Pro His Pro Asp Pro His Pro Asp Pro His Pro Asp
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 244

Pro Pro Pro Pro Pro His Pro His Pro His Pro His Pro His Pro His
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 245

Pro Pro Pro Pro Pro His Pro Asp Pro Asp Pro His Pro Asp Pro Asp
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 246

Pro Pro Pro Pro Pro His Pro Glu Pro Glu Pro His Pro Glu Pro Glu
1               5                   10                  15

<210> SEQ ID NO 247
<211> LENGTH: 16
```

```
<212> TYPE: PRT
<213> ORGANISM: Artificial Sequence
<220> FEATURE:
<223> OTHER INFORMATION: Synthetic peptide with hydrophobic tail

<400> SEQUENCE: 247

Ser Ser Ser Ser Ser Arg Ser Asp Ser Arg Ser Asp Ser Arg Ser Asp
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 248

Ser Ser Ser Ser Ser Arg Ser Arg Ser Asp Ser Asp Ser Arg Ser Arg
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 249

Phe Phe Phe Phe Phe Arg Phe Arg Phe Arg Phe Arg Phe Asp Phe Asp
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 250

Ser Ser Ser Ser Ser Glu Ser Glu Ser Lys Ser Lys Ser Glu Ser Glu
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 251

Ser Ser Ser Ser Ser Arg Ser Glu Ser Arg Ser Glu Ser Arg Ser Glu
1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 252

Ser Ser Ser Ser Ser Arg Ser Arg Ser Glu Ser Glu Ser Arg Ser Glu
1               5                   10                  15

<210> SEQ ID NO 253
<211> LENGTH: 16
<212> TYPE: PRT
```

<213> ORGANISM: Artificial Sequence
<220> FEATURE:
<223> OTHER INFORMATION: Synthetic peptide with hydrophobic tail

<400> SEQUENCE: 253

Ser Ser Ser Ser Ser Lys Ser Asp Ser Lys Ser Asp Ser Lys Ser Asp
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 254

Ser Ser Ser Ser Ser Glu Ser His Ser Glu Ser His Ser Glu Ser His
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 255

Ser Ser Ser Ser Ser Glu Ser Glu Ser His Ser His Ser Glu Ser Glu
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 256

Ser Ser Ser Ser Ser Arg Ser Arg Ser Arg Ser Arg Ser Arg Ser Arg
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 257

Ser Ser Ser Ser Ser Arg Ser Arg Ser Arg Ser Arg Ser Asp Ser Asp
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 258

Ser Ser Ser Ser Ser Arg Ser Arg Ser Arg Ser Asp Ser Asp Ser Asp
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 259

Ser Ser Ser Ser Ser His Ser Asp Ser His Ser Asp Ser His Ser Asp
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 260

Ser Ser Ser Ser Ser His Ser His Ser His Ser His Ser His Ser His
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 261

Ser Ser Ser Ser Ser His Ser Asp Ser Asp Ser His Ser Asp Ser Asp
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 262

Ser Ser Ser Ser Ser His Ser Glu Ser Glu Ser His Ser Glu Ser Glu
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 263

Thr Thr Thr Thr Thr Arg Thr Asp Thr Arg Thr Asp Thr Arg Thr Asp
1               5                   10                  15

<210> SEQ ID NO 264
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 264

Thr Thr Thr Thr Thr Arg Thr Arg Thr Asp Thr Asp Thr Arg Thr Arg
1               5                   10                  15

<210> SEQ ID NO 265
<211> LENGTH: 16
<212> TYPE: PRT
<213> ORGANISM: Artificial Sequence
<220> FEATURE:

-continued

<223> OTHER INFORMATION: Synthetic peptide with hydrophobic tail

<400> SEQUENCE: 265

Thr Thr Thr Thr Thr Glu Thr Lys Thr Glu Thr Lys Thr Glu Thr Lys
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 266

Thr Thr Thr Thr Thr Glu Thr Glu Thr Lys Thr Lys Thr Glu Thr Glu
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 267

Thr Thr Thr Thr Thr Arg Thr Glu Thr Arg Thr Glu Thr Arg Thr Glu
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 268

Thr Thr Thr Thr Thr Arg Thr Arg Thr Glu Thr Glu Thr Arg Thr Glu
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 269

Thr Thr Thr Thr Thr Lys Thr Asp Thr Lys Thr Asp Thr Lys Thr Asp
1               5                   10                  15

<210> SEQ ID NO 270
<211> LENGTH: 32
<212> TYPE: PRT
<213> ORGANISM: Artificial Sequence
<220> FEATURE:
<223> OTHER INFORMATION: Synthetic peptide with hydrophobic tail

<400> SEQUENCE: 270

Thr Thr Thr Thr Thr Glu Thr Glu Thr His Thr His Thr Glu Thr Glu
1               5                   10                  15

Thr Thr Thr Thr Thr Glu Thr His Thr Glu Thr His Thr Glu Thr His
                20                  25                  30

<210> SEQ ID NO 271
<211> LENGTH: 16
<212> TYPE: PRT

-continued

```
<213> ORGANISM: Artificial Sequence
<220> FEATURE:
<223> OTHER INFORMATION: Synthetic peptide with hydrophobic tail

<400> SEQUENCE: 271

Thr Thr Thr Thr Thr Glu Thr Glu Thr His Thr His Thr Glu Thr Glu
1               5                   10                  15

<210> SEQ ID NO 272
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 272

Thr Thr Thr Thr Thr Arg Thr Arg Thr Arg Thr Arg Thr Arg Thr Arg
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 273

Thr Thr Thr Thr Thr Arg Thr Arg Thr Arg Thr Arg Thr Asp Thr Asp
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 274

Thr Thr Thr Thr Thr Arg Thr Arg Thr Arg Thr Asp Thr Asp Thr Asp
1               5                   10                  15

<210> SEQ ID NO 275
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 275

Thr Thr Thr Thr Thr His Thr Asp Thr His Thr Asp Thr His Thr Asp
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 276

Thr Thr Thr Thr Thr His Thr His Thr His Thr His Thr His Thr His
1               5                   10                  15

<210> SEQ ID NO 277
<211> LENGTH: 16
<212> TYPE: PRT
<213> ORGANISM: Artificial Sequence
```

```
<220> FEATURE:
<223> OTHER INFORMATION: Synthetic peptide with hydrophobic tail

<400> SEQUENCE: 277

Thr Thr Thr Thr Thr His Thr Asp Thr Asp Thr His Thr Asp Thr Asp
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 278

Thr Thr Thr Thr Thr His Thr Glu Thr Glu Thr His Thr Glu Thr Glu
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 279

Cys Cys Cys Cys Cys Arg Cys Asp Cys Arg Cys Asp Cys Arg Cys Asp
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 280

Cys Cys Cys Cys Cys Arg Cys Arg Cys Asp Cys Asp Cys Arg Cys Arg
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 281

Cys Cys Cys Cys Cys Glu Cys Lys Cys Glu Cys Lys Cys Glu Cys Lys
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 282

Cys Cys Cys Cys Cys Glu Cys Glu Cys Lys Cys Lys Cys Glu Cys Glu
1               5                   10                  15

<210> SEQ ID NO 283
<211> LENGTH: 16
<212> TYPE: PRT
<213> ORGANISM: Artificial Sequence
<220> FEATURE:
```

<223> OTHER INFORMATION: Synthetic peptide with hydrophobic tail

<400> SEQUENCE: 283

Cys Cys Cys Cys Cys Arg Cys Glu Cys Arg Cys Glu Cys Arg Cys Glu
1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 284

Cys Cys Cys Cys Cys Arg Cys Arg Cys Glu Cys Glu Cys Arg Cys Glu
1               5                   10                  15

<210> SEQ ID NO 285
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 285

Cys Cys Cys Cys Cys Lys Cys Asp Cys Lys Cys Asp Cys Lys Cys Asp
1               5                   10                  15

<210> SEQ ID NO 286
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 286

Cys Cys Cys Cys Cys Glu Cys His Cys Glu Cys His Cys Glu Cys His
1               5                   10                  15

<210> SEQ ID NO 287
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 287

Cys Cys Cys Cys Cys Glu Cys Glu Cys His Cys His Cys Glu Cys Glu
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 288

Cys Cys Cys Cys Cys Arg Cys Arg Cys Arg Cys Arg Cys Arg Cys Arg
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 289

Cys Cys Cys Cys Cys Arg Cys Arg Cys Arg Cys Asp Cys Asp
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 290

Cys Cys Cys Cys Cys Arg Cys Arg Cys Arg Cys Asp Cys Asp Cys Asp
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 291

Cys Cys Cys Cys Cys His Cys Asp Cys His Cys Asp Cys His Cys Asp
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 292

Cys Cys Cys Cys Cys His Cys His Cys His Cys His Cys His Cys His
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 293

Cys Cys Cys Cys Cys His Cys Asp Cys Asp Cys His Cys Asp Cys Asp
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 294

Cys Cys Cys Cys Cys His Cys Glu Cys Glu Cys His Cys Glu Cys Glu
1               5                   10                  15

<210> SEQ ID NO 295
<211> LENGTH: 16
<212> TYPE: PRT
<213> ORGANISM: Artificial Sequence
<220> FEATURE:
<223> OTHER INFORMATION: Synthetic peptide with hydrophobic tail -continued

<400> SEQUENCE: 295

Tyr Tyr Tyr Tyr Tyr Arg Tyr Asp Tyr Arg Tyr Asp Tyr Arg Tyr Asp
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 296

Tyr Tyr Tyr Tyr Tyr Arg Tyr Arg Tyr Asp Tyr Asp Tyr Arg Tyr Arg
1               5                   10                  15

<210> SEQ ID NO 297
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 297

Tyr Tyr Tyr Tyr Tyr Glu Tyr Lys Tyr Glu Tyr Lys Tyr Glu Tyr Lys
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 298

Tyr Tyr Tyr Tyr Tyr Glu Tyr Glu Tyr Lys Tyr Lys Tyr Glu Tyr Glu
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 299

Tyr Tyr Tyr Tyr Tyr Arg Tyr Glu Tyr Arg Tyr Glu Tyr Arg Tyr Glu
1               5                   10                  15

<210> SEQ ID NO 300
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 300

Tyr Tyr Tyr Tyr Tyr Arg Tyr Arg Tyr Glu Tyr Glu Tyr Arg Tyr Glu
1               5                   10                  15

<210> SEQ ID NO 301
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 301

Tyr Tyr Tyr Tyr Tyr Lys Tyr Asp Tyr Lys Tyr Asp Tyr Lys Tyr Asp
1               5                   10                  15

<210> SEQ ID NO 302
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 302

Tyr Tyr Tyr Tyr Tyr Glu Tyr His Tyr Glu Tyr His Tyr Glu Tyr His
1               5                   10                  15

<210> SEQ ID NO 303
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 303

Tyr Tyr Tyr Tyr Tyr Glu Tyr Glu Tyr His Tyr His Tyr Glu Tyr Glu
1               5                   10                  15

<210> SEQ ID NO 304
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 304

Tyr Tyr Tyr Tyr Tyr Arg Tyr Arg Tyr Arg Tyr Arg Tyr Arg Tyr Arg
1               5                   10                  15

<210> SEQ ID NO 305
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 305

Tyr Tyr Tyr Tyr Tyr Arg Tyr Arg Tyr Arg Tyr Arg Tyr Asp Tyr Asp
1               5                   10                  15

<210> SEQ ID NO 306
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 306

Tyr Tyr Tyr Tyr Tyr Arg Tyr Arg Tyr Arg Tyr Asp Tyr Asp Tyr Asp
1               5                   10                  15

<210> SEQ ID NO 307
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 307

Tyr Tyr Tyr Tyr Tyr His Tyr Asp Tyr His Tyr Asp Tyr His Tyr Asp
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 308

Tyr Tyr Tyr Tyr Tyr His Tyr His Tyr His Tyr His Tyr His Tyr His
1               5                   10                  15

<210> SEQ ID NO 309
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 309

Tyr Tyr Tyr Tyr Tyr His Tyr Asp Tyr Asp Tyr His Tyr Asp Tyr Asp
1               5                   10                  15

<210> SEQ ID NO 310
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 310

Tyr Tyr Tyr Tyr Tyr His Tyr Glu Tyr Glu Tyr His Tyr Glu Tyr Glu
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 311

Asn Asn Asn Asn Asn Arg Asn Asp Asn Arg Asn Asp Asn Arg Asn Asp
1               5                   10                  15

<210> SEQ ID NO 312
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 312

Asn Asn Asn Asn Asn Arg Asn Arg Asn Asp Asn Asp Asn Arg Asn Arg
1               5                   10                  15

<210> SEQ ID NO 313
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 313

Asn Asn Asn Asn Asn Glu Asn Lys Asn Glu Asn Lys Asn Glu Asn Lys

<210> SEQ ID NO 314
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 314

Asn Asn Asn Asn Asn Glu Asn Glu Asn Lys Asn Lys Asn Glu Asn Glu
1               5                   10                  15

<210> SEQ ID NO 315
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 315

Asn Asn Asn Asn Asn Arg Asn Glu Asn Arg Asn Glu Asn Arg Asn Glu
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 316

Asn Asn Asn Asn Asn Arg Asn Arg Asn Glu Asn Glu Asn Arg Asn Glu
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 317

Asn Asn Asn Asn Asn Lys Asn Asp Asn Lys Asn Asp Asn Lys Asn Asp
1               5                   10                  15

<210> SEQ ID NO 318
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 318

Asn Asn Asn Asn Asn Glu Asn His Asn Glu Asn His Asn Glu Asn His
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 319

Asn Asn Asn Asn Asn Glu Asn Glu Asn His Asn His Asn Glu Asn Glu
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 320

Asn Asn Asn Asn Asn Arg Asn Arg Asn Arg Asn Arg Asn Arg Asn Arg
1               5                   10                  15

<210> SEQ ID NO 321
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 321

Asn Asn Asn Asn Asn Arg Asn Arg Asn Arg Asn Arg Asn Asp Asn Asp
1               5                   10                  15

<210> SEQ ID NO 322
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 322

Asn Asn Asn Asn Asn Arg Asn Arg Asn Arg Asn Asp Asn Asp Asn Asp
1               5                   10                  15

<210> SEQ ID NO 323
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 323

Asn Asn Asn Asn Asn His Asn Asp Asn His Asn Asp Asn His Asn Asp
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 324

Asn Asn Asn Asn Asn His Asn His Asn His Asn His Asn His Asn His
1               5                   10                  15

<210> SEQ ID NO 325
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 325

Asn Asn Asn Asn Asn His Asn Asp Asn Asp Asn His Asn Asp Asn Asp
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 326

Asn Asn Asn Asn Asn His Asn Glu Asn Glu Asn His Asn Glu Asn Glu
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 327

Gln Gln Gln Gln Gln Arg Gln Asp Gln Arg Gln Asp Gln Arg Gln Asp
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 328

Gln Gln Gln Gln Gln Arg Gln Arg Gln Asp Gln Asp Gln Arg Gln Arg
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 329

Gln Gln Gln Gln Gln Glu Gln Lys Gln Glu Gln Lys Gln Glu Gln Lys
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 330

Gln Gln Gln Gln Gln Glu Gln Glu Gln Lys Gln Lys Gln Glu Gln Glu
1               5                   10                  15

<210> SEQ ID NO 331
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 331

Gln Gln Gln Gln Gln Arg Gln Glu Gln Arg Gln Glu Gln Arg Gln Glu
1               5                   10                  15

-continued

```
<210> SEQ ID NO 332
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 332

Gln Gln Gln Gln Gln Arg Gln Arg Gln Glu Gln Glu Gln Arg Gln Glu
1               5                   10                  15

<210> SEQ ID NO 333
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 333

Gln Gln Gln Gln Gln Lys Gln Asp Gln Lys Gln Asp Gln Lys Gln Asp
1               5                   10                  15

<210> SEQ ID NO 334
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 334

Gln Gln Gln Gln Gln Glu Gln His Gln Glu Gln His Gln Glu Gln His
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 335

Gln Gln Gln Gln Gln Glu Gln Glu Gln His Gln His Gln Glu Gln Glu
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 336

Gln Gln Gln Gln Gln Arg Gln Arg Gln Arg Gln Arg Gln Arg Gln Arg
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 337

Gln Gln Gln Gln Gln Arg Gln Arg Gln Arg Gln Arg Gln Asp Gln Asp
1               5                   10                  15

<210> SEQ ID NO 338
```

```
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 338

Gln Gln Gln Gln Gln Arg Gln Arg Gln Arg Gln Asp Gln Asp Gln Asp
1               5                   10                  15

<210> SEQ ID NO 339
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 339

Gln Gln Gln Gln Gln His Gln Asp Gln His Gln Asp Gln His Gln Asp
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 340

Gln Gln Gln Gln Gln His Gln His Gln His Gln His Gln His Gln His
1               5                   10                  15

<210> SEQ ID NO 341
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 341

Gln Gln Gln Gln Gln His Gln Asp Gln Asp Gln His Gln Asp Gln Asp
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Synthetic peptide with hydrophobic tail

<400> SEQUENCE: 342

Gln Gln Gln Gln Gln His Gln Glu Gln Glu Gln His Gln Glu Gln Glu
1               5                   10                  15
```